US005834302A

United States Patent [19]
Racaniello et al.

[11] Patent Number: 5,834,302
[45] Date of Patent: Nov. 10, 1998

[54] METHOD FOR PRODUCING RNA VIRUSES FROM CDNA

[75] Inventors: Vincent Racaniello, New York, N.Y.; Joanne Marie Tatem, Lincoln Park, N.J.; Carolyn L. Weeks-Levy, Valvilla, N.Y.

[73] Assignee: The Trustees of Columbia University in the City of New York, New York, N.Y.

[21] Appl. No.: 461,503

[22] Filed: Jun. 5, 1995

Related U.S. Application Data

[63] Continuation of Ser. No. 852,260, continuation of PCT/US95/05890, Aug. 20, 1991, Pat. No. 5,525,715, which is a continuation-in-part of Ser. No. 569,916, Aug. 20, 1990, abandoned, and Ser. No. 570,000, Aug. 20, 1990, abandoned.

[51] Int. Cl.$^6$ ..................................................... C12N 15/43
[52] U.S. Cl. ...................... 435/252.3; 435/5; 435/172.3; 435/320.1; 435/235.1; 435/252.33; 435/254.11; 435/325; 435/348; 435/365; 435/367; 536/23.72; 424/217.1; 424/216.1
[58] Field of Search ................................. 435/5, 6, 235.1, 435/91.51, 172.1, 172.3, 252.3, 243, 325, 348–354, 363, 362, 365, 366, 367, 255.1, 252.33, 320.1, 254.11; 536/23.72, 23.1; 424/217.1, 216.1; 935/77

[56] References Cited

U.S. PATENT DOCUMENTS 4,719,177  1/1988  Baltimore et al. ........................ 435/91

OTHER PUBLICATIONS

Auld V.J. et al., "A Neutral Amino Acid Change In Segment IIS4 Dramatically Alters The Gating Properties Of The Voltage–Dependent Sodium Channel", Proc. Natl. Acad. Sc. (USA) Jan. 1990, vol. 87, pp. 323–327.

Boslego J.W., "Gonorrhea Vaccines", Vaccine and Immunotherapy S.J. Cryz Edt., 1990, Pergamon Press, pp. 211–223.

Bowie J.U. et al., "Deciphering The Message In Protein Sequences: Tolerance to Amino Acid Substitutions", Science, 1990, vol. 247, pp. 1306–1310.

Davis, et al., Microbiology, Third Edition, "Picornavirus" Chapter 57, 1980, pp. 1096–1108, Harper & Row, Publishers, PA.

DeBorde D.C., et al., "Resolution of a Common RNA Sequencing Ambiguity by Terminal Deoxynucleotidyl Transferase", Analytical Biochemistry, 1986, vol. 157, pp. 275–282.

Ellis R.W., "New Technology for Making Vaccines", Vaccines, Plotkin & Mortimer Edt., W.B. Saunders Co., 1988.

Kohara M., et al., "An Infectious cDNA Clone of the Poliovirus Sabin Strain Could be used as a Stable Repository and Inoculum for the oral Polio Live Vaccine", Virology, 1986, vol. 151

FIG. 3
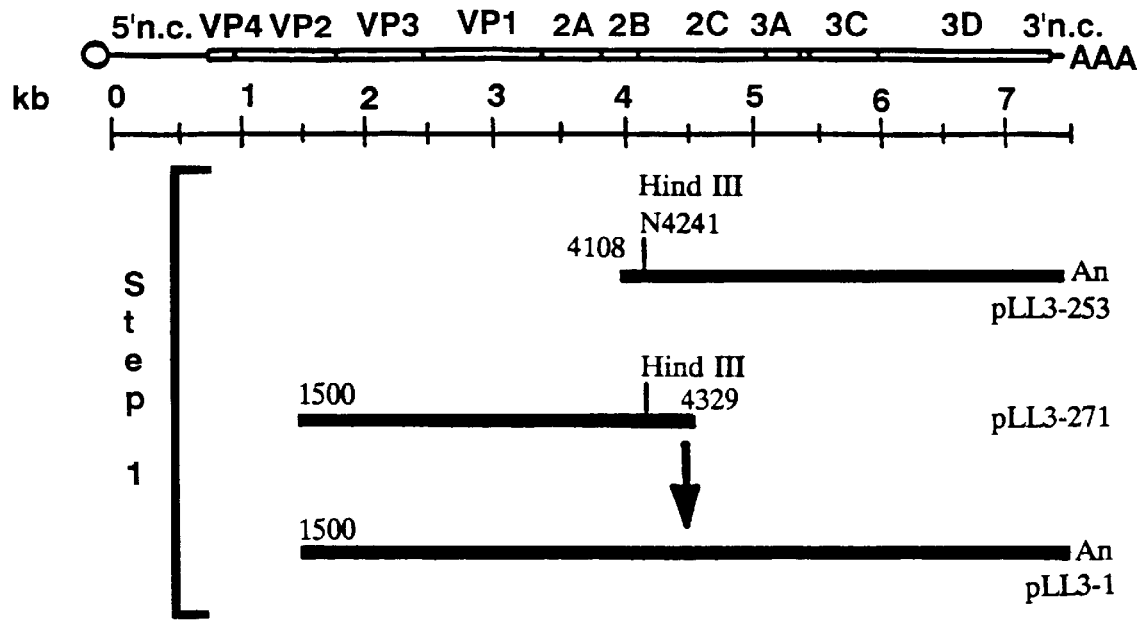
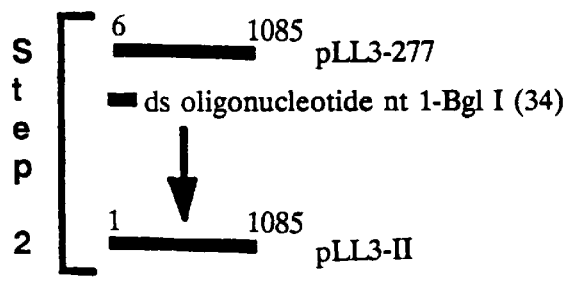
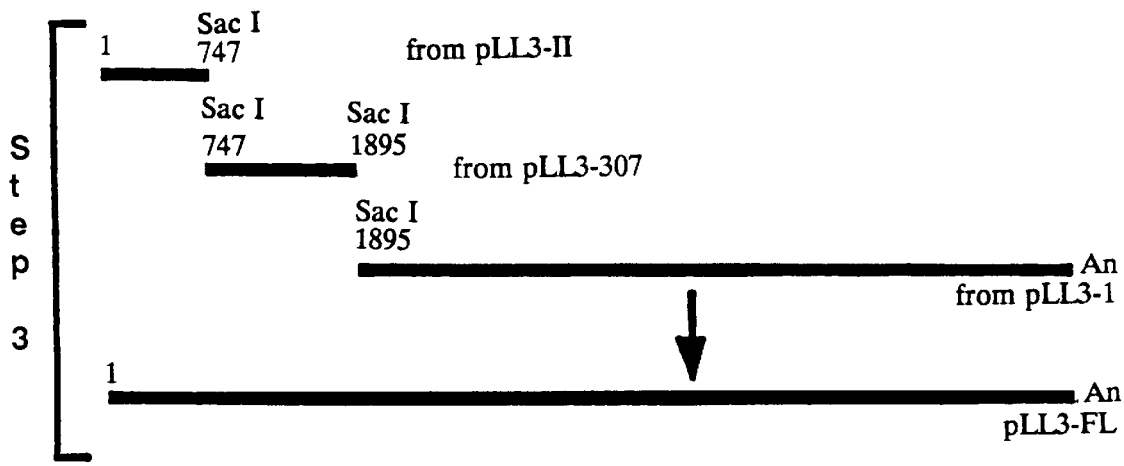

FIG. 6A

```
          10        20        30        40        50        60
TTAAAACAGCTCTGGGGTTGTTCCCACCCCAGAGGCCCACGTGGCGGCTAGTACACTGGT 70        80        90       100       110       120
ATCACGGTACCTTTGTACGCCTGTTTTATACTCCCTCCCCCGCAACTTAGAAGCATACAA 130       140       150       160       170       180
TTCAAGCTCAATAGGAGGGGGTGCAAGCCAGCGCCTCCGTGGGCAAGCACTACTGTTTCC 190       200       210       220       230       240
CCGGTGAGGCCGCATAGACTGTTCCCACGGTTGAAAGTGTCCGATCCGTTATCCGCTCAT 250       260       270       280       290       300
GTACTTCGAGAAGCCTAGTATCGCTCTGGAATCTTCGACGCGTTGCGCTCAGCACTCAAC 310       320       330       340       350       360
CCCGGAGTGTAGCTTGGGCCGATGAGTCTGGACAGTCCCCACTGGCGACAGTGGTCCAGG 370       380       390       400       410       420
CTGCGCTGGCGGCCCACCTGTGGCCCAAAGCCACGGGACGCTAGTTGTGAACAGGGTGTG 430       440       450       460       470       480
AAGAGCCTATTGAGCTACATGAGAGTCCTCCGGCCCCTGAATGCGGCTAATTCTAACCAT 490       500       510       520       530       540
GGAGCAGGCAGCTGCAACCCAGCAGCCAGCCTGTCGTAACGCGCAAGTCCGTGGCGGAAC 550       560       570       580       590       600
CGACTACTTTGGGTGTCCGTGTTTCCTTTTATTCTTGAATGGCTGCTTATGGTGACAATC 610       620       630       640       650       660
ATAGATTGTTATCATAAAGCGAGTTGGATTGGCCATCCAGTGTGAATCAGATTAATTACT 670       680       690       700       710       720
CCCTTGTTTGTTGGATCCACTCCCGAAACGTTTTACTCCTTAACTTATTGAAATTGTTTG 730       740       750       760       770       780
AAGACAGGATTTCAGTGTCACAATGGGAGCTCAAGTATCATCCCAAAAAGTAGGCGCTCA
                                M   G   A   Q   V   S   S   Q   K   V   G   A   H 790       800       810       820       830       840
CGAGAATTCTAACCGAGCCTACGGTGGTTCTACGATCAACTACACCACAATTAATTATTA
 E   N   S   N   R   A   Y   G   G   S   T   I   N   Y   T   T   I   N   Y   Y
```

FIG. 6B

```
         850       860       870       880       890       900
TAAAGATTCCGCAAGTAATGCGGCGTCCAAACAAGATTACTCACAGGATCCATCAAAATT
  K  D  S  A  S  N  A  A  S  K  Q  D  Y  S  Q  D  P  S  K  F 910       920       930       940       950       960
CACCGAGCCACTAAAGGACGTGCTCATAAAAACAGCTCCAGCACTCAATTCACCAAATGT
  T  E  P  L  K  D  V  L  I  K  T  A  P  A  L  N  S  P  N  V 970       980       990      1000      1010      1020
GGAAGCGTGTGGGTATAGTGATAGAGTGTTGCAACTCACTTTAGGCAATTCCACTATTAC
  E  A  C  G  Y  S  D  R  V  L  Q  L  T  L  G  N  S  T  I  T 1030      1040      1050      1060      1070      1080
TACACAGGAGGCAGCAAATTCAGTAGTGGCTTACGGACGTTGGCCTGAGTTTATTAGAGA
  T  Q  E  A  A  N  S  V  V  A  Y  G  R  W  P  E  F  I  R  D 1090      1100      1110      1120      1130      1140
TGACGAAGCAAACCCGGTGGACCAACCAACTGAACCAGATGTGGCTACATGCAGATTCTA
  D  E  A  N  P  V  D  Q  P  T  E  P  D  V  A  T  C  R  F  Y 1150      1160      1170      1180      1190      1200
CACACTAGACACTGTAATGTGGGGTAAGGAGTCGAAAGGCTGGTGGTGGAAGTTACCTGA
  T  L  D  T  V  M  W  G  K  E  S  K  G  W  W  W  K  L  P  D 1210      1220      1230      1240      1250      1260
CGCACTGAGAGACATGGGTCTGTTTGGACAAAACATGTATTACCACTACCTAGGAAGATC
  A  L  R  D  M  G  L  F  G  Q  N  M  Y  Y  H  Y  L  G  R  S 1270      1280      1290      1300      1310      1320
CGGGTACACTGTGCACGTGCAGTGTAATGCATCCAAATTTCACCAAGGTGCACTCGGGGT
  G  Y  T  V  H  V  Q  C  N  A  S  K  F  H  Q  G  A  L  G  V 1330      1340      1350      1360      1370      1380
GTTTGCGATTCCTGAGTATTGTCTGGCGGGTGACAGTGACAAGCAAAGGTACACTAGTTA
  F  A  I  P  E  Y  C  L  A  G  D  S  D  K  Q  R  Y  T  S  Y 1390      1400      1410      1420      1430      1440
TGCAAATGCGAATCCAGGTGAAAGAGGGGGAAAATTTTACTCCCAATTCAACAAGGATAA
  A  N  A  N  P  G  E  R  G  G  K  F  Y  S  Q  F  N  K  D  N 1450      1460      1470      1480      1490      1500
CGCAGTAACATCCCCAAAAAGAGAGTTCTGCCCAGTGGATTATCTCCTGGGATGTGGGGT
  A  V  T  S  P  K  R  E  F  C  P  V  D  Y  L  L  G  C  G  V 1510      1520      1530      1540      1550      1560
GTTACTGGGAAATGCCTTTGTATACCCACATCAAATCATTAATCTGAGGACCAACAACAG
  L  L  G  N  A  F  V  Y  P  H  Q  I  I  N  L  R  T  N  N  S
```

FIG. 6C

```
      1570       1580       1590       1600       1610       1620
CGCAACTATTGTCCTACCATATGTGAATGCTTTGGCCATTGATTCAATGGTTAAACACAA
  A  T  I  V  L  P  Y  V  N  A  L  A  I  D  S  M  V  K  H  N 1630       1640       1650       1660       1670       1680
CAACTGGGGCATTGCCATTCTGCCCTTATCACCGCTGGATTTTGCTCAAGATTCATCAGT
  N  W  G  I  A  I  L  P  L  S  P  L  D  F  A  Q  D  S  S  V 1690       1700       1710       1720       1730       1740
TGAAATTCCAATTACTGTGACAATTGCCCCAATGTGTAGCGAGTTCAACGGCCTTCGCAA
  E  I  P  I  T  V  T  I  A  P  M  C  S  E  F  N  G  L  R  N 1750       1760       1770       1780       1790       1800
CGTGACTGCACCTAAATTTCAAGGACTACCAGTGTTGAACACTCCTGGTAGTAACCAGTA
  V  T  A  P  K  F  Q  G  L  P  V  L  N  T  P  G  S  N  Q  Y 1810       1820       1830       1840       1850       1860
CCTGACGTCAGACAACCACCAATCACCATGCGCAATCCCAGAATTTGATGTCACTCCGCC
  L  T  S  D  N  H  Q  S  P  C  A  I  P  E  F  D  V  T  P  P 1870       1880       1890       1900       1910       1920
TATTGATATCCCAGGTGAGGTTAAAAACATGATGGAGCTCGCCGAGATAGACACCATGAT
  I  D  I  P  G  E  V  K  N  M  M  E  L  A  E  I  D  T  M  I 1930       1940       1950       1960       1970       1980
TCCTCTCAATTTGGAGAGCACCAAGAGAAACACAATGGACATGTACAGAGTTACTCTGAG
  P  L  N  L  E  S  T  K  R  N  T  M  D  M  Y  R  V  T  L  S 1990       2000       2010       2020       2030       2040
CGACAGTGCCGATCTATCGCAACCAATTTTGTGCTTGTCACTATCCCCAGCATTTGATCC
  D  S  A  D  L  S  Q  P  I  L  C  L  S  L  P  A  F  D  P 2050       2060       2070       2080       2090       2100
GCGCTTGTCACACACCATGCTTGGGGAAGTACTGAACTATTATACTCATTGGGCCGGGTC
  R  L  S  H  T  M  L  G  E  V  L  N  Y  Y  T  H  W  A  G  S 2110       2120       2130       2140       2150       2160
CTTGAAATTTACCTTCCTGTTCTGTGGTTCAATGATGGCTACGGGGAAAATCCTAGTGGC
  L  K  F  T  F  L  F  C  G  S  M  M  A  T  G  K  I  L  V  A 2170       2180       2190       2200       2210       2220
CTATGCACCACCAGGTGCACAACCCCCCACCAGCCGTAAGGAGGCTATGTTGGGCACACA
  Y  A  P  P  G  A  Q  P  P  T  S  R  K  E  A  M  L  G  T  H
```

FIG. 6D

```
       2230      2240      2250      2260      2270      2280
TGTCATTTGGGATCTTGGCCTGCAATCATCTTGTACTATGGTGGTGCCGTGGATTAGTAA
  V  I  W  D  L  G  L  Q  S  S  C  T  M  V  V  P  W  I  S  N 2290      2300      2310      2320      2330      2340
TGTGACATACAGACAGACTACACAAGATAGTTTCACTGAGGGCGGATATATCAGCATGTT
  V  T  Y  R  Q  T  T  Q  D  S  F  T  E  G  G  Y  I  S  M  F 2350      2360      2370      2380      2390      2400
CTACCAAACAAGAATTGTGGTGCCACTGTCCACCCCTAAGAGTATGAGCATGCTGGGGTT
  Y  Q  T  R  I  V  V  P  L  S  T  P  K  S  M  S  M  L  G  F 2410      2420      2430      2440      2450      2460
TGTGTCAGCCTGTAATGATTTCAGTGTGCGATTGCTGCGAGACACCACTCACATTTCACA
  V  S  A  C  N  D  F  S  V  R  L  L  R  D  T  T  H  I  S  Q 2470      2480      2490      2500      2510      2520
ATCTGCGCTTCCACAGGGTATTGAAGATTTGACTTCTGAAGTTGCACAGGGCGCCCTAAC
  S  A  L  P  Q  G  I  E  D  L  T  S  E  V  A  Q  G  A  L  T 2530      2540      2550      2560      2570      2580
TTTGTCACTCCCGAAGCAACAGGATAGCTTACCTGATACTAAGGCCAGTGGCCCGGCGCA
  L  S  L  P  K  Q  Q  D  S  L  P  D  T  K  A  S  G  P  A  H 2590      2600      2610      2620      2630      2640
TTCCAAGGAGGTACCTGCACTCACTGCAGTCGAGACTGGAGCCACCAATCCTCTGGCACC
  S  K  E  V  P  A  L  T  A  V  E  T  G  A  T  N  P  L  A  P 2650      2660      2670      2680      2690      2700
ATCCGACACAGTTCAAACGCGCCACGTAGTCCAACGACGCAGCAGGTCAGAGTCCACAAT
  S  D  T  V  Q  T  R  H  V  V  Q  R  R  S  R  S  E  S  T  I 2710      2720      2730      2740      2750      2760
AGAATCATTCTTCGCACGCGGGGCGTGCGTCGCTATTATTGAGGTGGACAATGAACAACC
  E  S  F  F  A  R  G  A  C  V  A  I  I  E  V  D  N  E  Q  P 2770      2780      2790      2800      2810      2820
AACCACCCGGGCACAGAAACTATTTGCCATGTGGCGCATTACATACAAAGATACAGTGCA
  T  T  R  A  Q  K  L  F  A  M  W  R  I  T  Y  K  D  T  V  Q 2830      2840      2850      2860      2870      2880
GTTGCGCCGTAAGTTGGAGTTTTTTCACATACTCTCGTTTTGACATGGAATTCACCTTCGT
  L  R  R  K  L  E  F  F  T  Y  S  R  F  D  M  E  F  T  F  V
```

FIG. 6E

```
          2890       2900       2910       2920       2930       2940
       GGTAACCGCCAACTTCACCAACGCTAATAATGGGCATGCACTCAACCAGGTGTACCAGAT
        V  T  A  N  F  T  N  A  N  N  G  H  A  L  N  Q  V  Y  Q  I 2950       2960       2970       2980       2990       3000
       AATGTACATCCCCCCAGGGGCACCCACACCAAAGTCATGGGACGACTACACTTGGCAAAC
        M  Y  I  P  P  G  A  P  T  P  K  S  W  D  D  Y  T  W  Q  T 3010       3020       3030       3040       3050       3060
       ATCTTCCAACCCGTCCATATTTTACACCTATGGGGCTGCCCCGGCGCGAATCTCAGTGCC
        S  S  N  P  S  I  F  Y  T  Y  G  A  A  P  A  R  I  S  V  P 3070       3080       3090       3100       3110       3120
       ATACGTGGGGTTAGCCAATGCTTACTCGCACTTTTACGACGGCTTCGCCAAGGTGCCATT
        Y  V  G  L  A  N  A  Y  S  H  F  Y  D  G  F  A  K  V  P  L 3130       3140       3150       3160       3170       3180
       GAAGACAGATGCCAATGACCAGATTGGTGATTCCTTGTACAGCGCCATGACAGTTGATGA
        K  T  D  A  N  D  Q  I  G  D  S  L  Y  S  A  M  T  V  D  D 3190       3200       3210       3220       3230       3240
       CTTTGGTGTATTGGCAGTTCGTGTTGTCAATGATCACAACCCCACTAAAGTAACCTCCAA
        F  G  V  L  A  V  R  V  V  N  D  H  N  P  T  K  V  T  S  K 3250       3260       3270       3280       3290       3300
       AGTCCGCATTTACATGAAACCCAAACACGTACGTGTCTGGTGCCCTAGACCGCCGCGCGC
        V  R  I  Y  M  K  P  K  H  V  R  V  W  C  P  R  P  P  R  A 3310       3320       3330       3340       3350       3360
       GGTACCTTATTATGGACCAGGGGTGGACTATAGGAACAACTTGGACCCCTTATCTGAGAA
        V  P  Y  Y  G  P  G  V  D  Y  R  N  N  L  D  P  L  S  E  K 3370       3380       3390       3400       3410       3420
       AGGTTTGACCACATATGGCTTTGGGCATCAGAATAAAGCTGTGTACACTGCTGGTTACAA
        G  L  T  T  Y  G  F  G  H  Q  N  K  A  V  Y  T  A  G  Y  K 3430       3440       3450       3460       3470       3480
       GATCTGCAACTACCATCTCGCCACTAAGGAGGATTTACAAAATGCTGTAAGCATCATGTG
        I  C  N  Y  H  L  A  T  K  E  D  L  Q  N  A  V  S  I  M  W 3490       3500       3510       3520       3530       3540
       GAATAGAGACCTCTTGGTTGTTGAATCAAAAGCTCAAGGTACCGACTCAATAGCAAGGTG
        N  R  D  L  L  V  V  E  S  K  A  Q  G  T  D  S  I  A  R  C
```

FIG. 6F

```
     3550      3560      3570      3580      3590      3600
CAATTGCAATGCAGGGGTGTACTATTGTGAGTCCAGAAGGAAATACTACCCTGTGTCGTT
  N  C  N  A  G  V  Y  Y  C  E  S  R  R  K  Y  Y  P  V  S  F 3610      3620      3630      3640      3650      3660
TGTGGGACCCACCTTCCAATACATGGAGGCTAATGACTACTACCCAGCTAGATACCAATC
  V  G  P  T  F  Q  Y  M  E  A  N  D  Y  Y  P  A  R  Y  Q  S 3670      3680      3690      3700      3710      3720
CCACATGTTAATCGGGCACGGCTTTGCCTCACCAGGTGACTGTGGTGGTATCCTTAGGTG
  H  M  L  I  G  H  G  F  A  S  P  G  D  C  G  G  I  L  R  C 3730      3740      3750      3760      3770      3780
TCAACATGGCGTCATCGGAATCGTGACAGCTGGTGGAGAGGGATTAGTCGCATTCTCTGA
  Q  H  G  V  I  G  I  V  T  A  G  G  E  G  L  V  A  F  S  D 3790      3800      3810      3820      3830      3840
CATAAGGGACTTGTATGCTTACGAGGAAGAGGCCATGGAGCAGGGCATTTCAAACTATAT
  I  R  D  L  Y  A  Y  E  E  E  A  M  E  Q  G  I  S  N  Y  I 3850      3860      3870      3880      3890      3900
TGAGTCACTCGGTGCTGCGTTCGGTAGTGGGTTCACTCAGCAAATAGGGGATAAGATATC
  E  S  L  G  A  A  F  G  S  G  F  T  Q  Q  I  G  D  K  I  S 3910      3920      3930      3940      3950      3960
AGAACTAACCAGCATGGTGACCAGCACGATTACAGAGAAGCTACTTAAAAACCTAATCAA
  E  L  T  S  M  V  T  S  T  I  T  E  K  L  L  K  N  L  I  K 3970      3980      3990      4000      4010      4020
AATTATTTCATCTCTGGTGATTATCACTAGAAATTACGAAGATACCACCACAGTGCTCGC
  I  I  S  S  L  V  I  I  T  R  N  Y  E  D  T  T  T  V  L  A 4030      4040      4050      4060      4070      4080
CACTCTAGCTCTTCTTGGGTGTGATGTTTCACCGTGGCAATGGCTGAAGAAGAAAGCATG
  T  L  A  L  L  G  C  D  V  S  P  W  Q  W  L  K  K  K  A  C 4090      4100      4110      4120      4130      4140
TGACACTTTGGAGATTCCCTATGTTATTAGACAGGGTGATAGTTGGTTGAAAAAATTTAC
  D  T  L  E  I  P  Y  V  I  R  Q  G  D  S  W  L  K  K  F  T 4150      4160      4170      4180      4190      4200
TGAGGCGTGCAACGCAGCTAAGGGGTTGGAATGGGTGTCCAACAAAATCTCAAAATTTAT
  E  A  C  N  A  A  K  G  L  E  W  V  S  N  K  I  S  K  F  I
```

FIG. 6G

```
           4210       4220       4230       4240       4250       4260
     TGACTGGTTGAGAGAAAGAATCATCCCACAAGCCAGGGACAAGCTTGAGTTTGTAACCAA
      D  W  L  R  E  R  I  I  P  Q  A  R  D  K  L  E  F  V  T  K 4270       4280       4290       4300       4310       4320
     ATTGAAACAGTTGGAAATGCTAGAGAATCAGATATCCACAATACACCAATCTTGTCCAAG
      L  K  Q  L  E  M  L  E  N  Q  I  S  T  I  H  Q  S  C  P  S 4330       4340       4350       4360       4370       4380
     TCAGGAACACCAGGAAATTTTGTTCAACAATGTACGCTGGTTGTCCATTCAATCCAAGAG
      Q  E  H  Q  E  I  L  F  N  N  V  R  W  L  S  I  Q  S  K  R 4390       4400       4410       4420       4430       4440
     ATTCGCTCCATTGTACGCACTTGAGGCCAAGAGAATACAAAAGTTGGAACACACCATTAA
      F  A  P  L  Y  A  L  E  A  K  R  I  Q  K  L  E  H  T  I  N 4450       4460       4470       4480       4490       4500
     TAATTACATACAGTTCAAGAGCAAACACCGTATTGAGCCAGTATGTTTGTTAGTGCATGG
      N  Y  I  Q  F  K  S  K  H  R  I  E  P  V  C  L  L  V  H  G 4510       4520       4530       4540       4550       4560
     GAGCCCAGGTACAGGAAAATCAGTTGCGACTAACCTAATTGCTAGAGCCATAGCTGAGAA
      S  P  G  T  G  K  S  V  A  T  N  L  I  A  R  A  I  A  E  K 4570       4580       4590       4600       4610       4620
     AGAGAACACCTCCACCTACTCGCTACCACCGGACCCGTCTCACTTTGATGGATACAAACA
      E  N  T  S  T  Y  S  L  P  P  D  P  S  H  F  D  G  Y  K  Q 4630       4640       4650       4660       4670       4680
     ACAAGGTGTGGTTATCATGGACGACCTAAACCAAAACCCGGATGGGGCAGATATGAAGCT
      Q  G  V  V  I  M  D  D  L  N  Q  N  P  D  G  A  D  M  K  L 4690       4700       4710       4720       4730       4740
     CTTTTGTCAAATGGTGTCCACTGTGGAGTTTATCCCACCTATGGCCTCGCTGGAAGAGAA
      F  C  Q  M  V  S  T  V  E  F  I  P  P  M  A  S  L  E  E  K 4750       4760       4770       4780       4790       4800
     AGGCATTCTGTTCACATCCAACTATGTTTTAGCCTCCACCAACTCCAGTCGCATCACACC
      G  I  L  F  T  S  N  Y  V  L  A  S  T  N  S  S  R  I  T  P 4810       4820       4830       4840       4850       4860
     ACCTACAGTAGCCCACAGTGACGCTCTGGCCAGGAGGTTCGCTTTCGATATGGATATTCA
      P  T  V  A  H  S  D  A  L  A  R  R  F  A  F  D  M  D  I  Q
```

FIG. 6H

```
         4870       4880       4890       4900       4910       4920
       AGTGATGGGCGAGTACTCCAGAGATGGTAAACTCAACATGGCAATGGCTACTGAGACGTG
         V  M  G  E  Y  S  R  D  G  K  L  N  M  A  M  A  T  E  T  C 4930       4940       4950       4960       4970       4980
       CAAGGACTGCCACCAACCAGCAAACTTCAAAAGATGCTGTCCTTTAGTGTGTGGTAAGGC
         K  D  C  H  Q  P  A  N  F  K  R  C  C  P  L  V  C  G  K  A 4990       5000       5010       5020       5030       5040
       AATTCAGTTAATGGACAAATCTTCCAGAGTTAGGTACAGTGTTGACCAGATTACTACAAT
         I  Q  L  M  D  K  S  S  R  V  R  Y  S  V  D  Q  I  T  T  M 5050       5060       5070       5080       5090       5100
       GATTATCAACGAGAGAAACAGAAGATCTAACATTGGCAATTGCATGGAGGCTTTGTTCCA
         I  I  N  E  R  N  R  R  S  N  I  G  N  C  M  E  A  L  F  Q 5110       5120       5130       5140       5150       5160
       AGGACCACTCCAGTACAAAGACCTGAAAATTGACATCAAGACGAGGCCCCCCCCTGAATG
         G  P  L  Q  Y  K  D  L  K  I  D  I  K  T  R  P  P  P  E  C 5170       5180       5190       5200       5210       5220
       CATCAATGATCTGCTTCAAGCAGTTGACTCCCAGGAAGTGAGGGATTATTGTGAAAAGAA
         I  N  D  L  L  Q  A  V  D  S  Q  E  V  R  D  Y  C  E  K  K 5230       5240       5250       5260       5270       5280
       AGGATGGATCGTCAACATCACTAGCCAAGTTCAAACAGAGAGAAACATTAACCGAGCAAT
         G  W  I  V  N  I  T  S  Q  V  Q  T  E  R  N  I  N  R  A  M 5290       5300       5310       5320       5330       5340
       GACCATTTTGCAGGCAGTGACAACTTTCGCCGCAGTGGCTGGTGTCGTGTACGTCATGTA
         T  I  L  Q  A  V  T  T  F  A  A  V  A  G  V  V  Y  V  M  Y 5350       5360       5370       5380       5390       5400
       CAAGTTATTCGCTGGACACCAGGGAGCATACACTGGTCTGCCAAACAAAAGACCCAATGT
         K  L  F  A  G  H  Q  G  A  Y  T  G  L  P  N  K  R  P  N  V 5410       5420       5430       5440       5450       5460
       GCCCACCATTAGAGCAGCAAAAGTGCAAGGGCCTGGGTTTGACTATGCAGTGGCTATGGC
         P  T  I  R  A  A  K  V  Q  G  P  G  F  D  Y  A  V  A  M  A 5470       5480       5490       5500       5510       5520
       TAAAAGAAACATTGTTACAGCAACTACTAGCAAAGGGGAGTTCACAATGCTAGGAGTCCA
         K  R  N  I  V  T  A  T  T  S  K  G  E  F  T  M  L  G  V  H
```

FIG. 6I

```
       5530      5540      5550      5560      5570      5580
CGACAACGTGGCCATTTTACCAACTCATGCCTCACCTGGTGAGAGTATTGTAATTGATGG
  D   N   V   A   I   L   P   T   H   A   S   P   G   E   S   I   V   I   D   G 5590      5600      5610      5620      5630      5640
CAAAGAGGTTGAAATCCTAGACGCTAAAGCCCTCGAAGATCAGGCAGGCACTAATCTGGA
  K   E   V   E   I   L   D   A   K   A   L   E   D   Q   A   G   T   N   L   E 5650      5660      5670      5680      5690      5700
AATCACCATAATAACCCTCAAAAGAAATGAAAAGTTCAGAGATATCAGACAACACATACC
  I   T   I   I   T   L   K   R   N   E   K   F   R   D   I   R   Q   H   I   P 5710      5720      5730      5740      5750      5760
CACTCAAATCACCGAGACGAATGATGGAGTTCTGATTGTGAACACTAGTAAGTACCCCAA
  T   Q   I   T   E   T   N   D   G   V   L   I   V   N   T   S   K   Y   P   N 5770      5780      5790      5800      5810      5820
CATGTATGTTCCTGTCGGTGCTGTGACTGAGCAGGGATACCTAAATCTCGGTGGGCGCCA
  M   Y   V   P   V   G   A   V   T   E   Q   G   Y   L   N   L   G   G   R   Q 5830      5840      5850      5860      5870      5880
GACTGCTCGTATTCTAATGTACAACTTTCCAACCAGAGCTGGTCAGTGTGGTGGAGTCAT
  T   A   R   I   L   M   Y   N   F   P   T   R   A   G   Q   C   G   G   V   I 5890      5900      5910      5920      5930      5940
CACATGCACTGGGAAAGTCATCGGGATGCACGTTGGTGGGAATGGTTCACATGGGTTTGC
  T   C   T   G   K   V   I   G   M   H   V   G   G   N   G   S   H   G   F   A 5950      5960      5970      5980      5990      6000
AGCGGCCCTGAAGCGGTCATACTTCACTCAGAGCCAAGGTGAAATCCAGTGGATGAGACC
  A   A   L   K   R   S   Y   F   T   Q   S   Q   G   E   I   Q   W   M   R   P 6010      6020      6030      6040      6050      6060
ATCAAAGGAGGCAGGGTATCCAATTATAAACGCCCCAACCAAGACCAAGCTCGAGCCCAG
  S   K   E   A   G   Y   P   I   I   N   A   P   T   K   T   K   L   E   P   S 6070      6080      6090      6100      6110      6120
TGCTTTCCACTATGTGTTTGAAGGAGTAAAGGAACCAGCAGTCCTCACAAAGAATGATCC
  A   F   H   Y   V   F   E   G   V   K   E   P   A   V   L   T   K   N   D   P 6130      6140      6150      6160      6170      6180
CAGACTCAAAACAGACTTTGAAGAAGCAATCTTCTCTAAGTATGTAGGGAACAAGATCAC
  R   L   K   T   D   F   E   E   A   I   F   S   K   Y   V   G   N   K   I   T
```

FIG. 6J

```
        6190       6200       6210       6220       6230       6240
TGAGGTGGATGAGTACATGAAAGAGGCAGTGGACCATTATGCTGGACAACTTATGTCGCT
  E  V  D  E  Y  M  K  E  A  V  D  H  Y  A  G  Q  L  M  S  L 6250       6260       6270       6280       6290       6300
GGATATCAGCACAGAGCAAATGTGTCTAGAAGACGCCATGTATGGTACTGATGGTCTGGA
  D  I  S  T  E  Q  M  C  L  E  D  A  M  Y  G  T  D  G  L  E 6310       6320       6330       6340       6350       6360
GGCGCTAGATCTGTCTACCAGTGCCGGGTACCCCTACGTGGCAATGGGGAAGAAGAAGAG
  A  L  D  L  S  T  S  A  G  Y  P  Y  V  A  M  G  K  K  K  R 6370       6380       6390       6400       6410       6420
AGATATCCTAAACAAGCAAACCAGAGACACCAAAGAAATGCAAAGACTTTTGGACGCTTA
  D  I  L  N  K  Q  T  R  D  T  K  E  M  Q  R  L  L  D  A  Y 6430       6440       6450       6460       6470       6480
CGGAATCAACCTACCATTAGTGACATATGTCAAGGACGAGCTGAGGTCCAAAACAAAAGT
  G  I  N  L  P  L  V  T  Y  V  K  D  E  L  R  S  K  T  K  V 6490       6500       6510       6520       6530       6540
GGAACAGGGAAAATCCAGACTGATTGAAGCTTCCAGTCTAAATGACTCAGTGGCCATGAG
  E  Q  G  K  S  R  L  I  E  A  S  S  L  N  D  S  V  A  M  R 6550       6560       6570       6580       6590       6600
AATGGCATTTGGAAACCTTTATGCAGCATTCCACAGGAATCCAGGGGTCGTCACTGGTAG
  M  A  F  G  N  L  Y  A  A  F  H  R  N  P  G  V  V  T  G  S 6610       6620       6630       6640       6650       6660
TGCAGTTGGATGCGATCCAGACCTATTCTGGAGCAAGATCCCAGTGTTGATGGAAGAAAA
  A  V  G  C  D  P  D  L  F  W  S  K  I  P  V  L  M  E  E  K 6670       6680       6690       6700       6710       6720
GCTATTTGCCTTTGATTACACAGGATACGACGCATCACTTAGCCCAGCTTGGTTTGAGGC
  L  F  A  F  D  Y  T  G  Y  D  A  S  L  S  P  A  W  F  E  A 6730       6740       6750       6760       6770       6780
ACTCAAGATGGTGTTAGAGAAAATTGGTTTTGGAGATAGAGTGGATTACATAGACTACCT
  L  K  M  V  L  E  K  I  G  F  G  D  R  V  D  Y  I  D  Y  L 6790       6800       6810       6820       6830       6840
TAACCATTCACACCACTTGTACAAAAACAAGATATATTGTGTTAAGGGCGGCATGCCATC
  N  H  S  H  H  L  Y  K  N  K  I  Y  C  V  K  G  G  M  P  S
```

FIG. 6K

```
           6850        6860        6870        6880        6890        6900
     TGGCTGCTCCGGCACTTCAATTTTTAATTCAATGATTAACAATTTGATCATTAGGACGCT
       G  C  S  G  T  S  I  F  N  S  M  I  N  N  L  I  I  R  T  L 6910        6920        6930        6940        6950        6960
     TTTACTGAAAACCTACAAGGGCATAGATTTGGACCACTTAAAAATGATTGCCTATGGTGA
       L  L  K  T  Y  K  G  I  D  L  D  H  L  K  M  I  A  Y  G  D 6970        6980        6990        7000        7010        7020
     CGATGTAATAGCTTCCTATCCCCATGAGGTTGACGCTAGTCTCCTAGCCCAATCAGGAAA
       D  V  I  A  S  Y  P  H  E  V  D  A  S  L  L  A  Q  S  G  K 7030        7040        7050        7060        7070        7080
     AGACTATGGACTAACCATGACTCCGGCAGATAAATCTGCCACTTTTGAGACAGTCACATG
       D  Y  G  L  T  M  T  P  A  D  K  S  A  T  F  E  T  V  T  W 7090        7100        7110        7120        7130        7140
     GGAGAATGTAACTTTCTTGAAAAGATTCTTCAGAGCAGATGAGAAATACCCCTTCCTCAT
       E  N  V  T  F  L  K  R  F  F  R  A  D  E  K  Y  P  F  L  I 7150        7160        7170        7180        7190        7200
     ACATCCAGTAATGCCAATGAAGGAAATTCATGAATCAATCAGATGGACAAAAGATCCTCG
       H  P  V  M  P  M  K  E  I  H  E  S  I  R  W  T  K  D  P  R 7210        7220        7230        7240        7250        7260
     GAATACGCAGGACCATGTACGCTCCTTGTGTCTATTGGCTTGGCACAACGGGGAAGAAGA
       N  T  Q  D  H  V  R  S  L  C  L  L  A  W  H  N  G  E  E  E 7270        7280        7290        7300        7310        7320
     ATACAACAAATTTTTAGCTAAAATTAGGAGTGTGCCAATCGGAAGAGCTTTGTTGCTCCC
       Y  N  K  F  L  A  K  I  R  S  V  P  I  G  R  A  L  L  P 7330        7340        7350        7360        7370        7380
     AGAGTACTCAACATTGTACCGCCGTTGGCTTGACTCATTTTAGTAACCCTACCTCAGTCG
       E  Y  S  T  L  Y  R  R  W  L  D  S  F  .  .

7390        7400        7410        7420        7430        7440
     AATTGGATTGGGTCATACTGTTGTAGGGGTAAATTTTTCTTTAATTCGGAGG
```

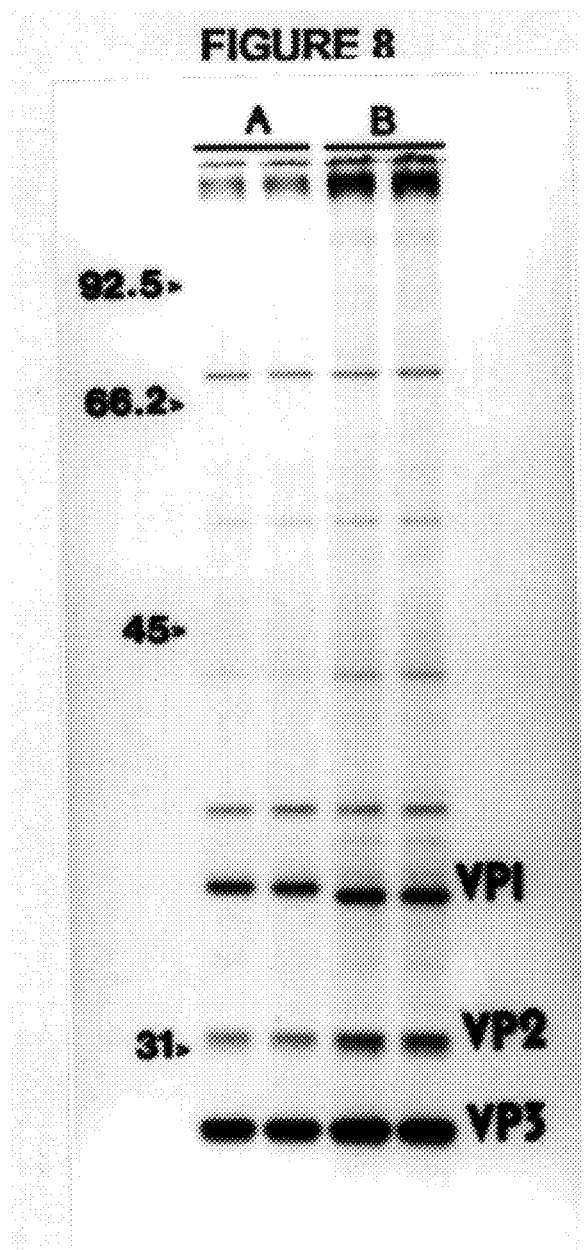

METHOD FOR PRODUCING RNA VIRUSES FROM CDNA

This application is a continuation of U.S. Ser. No. 07/852,260, filed Jun. 19, 1992, now U.S. Pat. No. 5,525, 715, which is a U.S. national stage application of PCT International Application No. PCT/US91/05890, filed Aug. 20, 1991, which is a continuation-in-part of U.S. Ser. No. 07/569,916, filed Aug. 20, 1990, now abandoned, and a continuation-in-part of U.S. Ser. No. 07/570,000, filed Aug. 20, 1990, now abandoned.

BACKGROUND OF THE INVENTION

Throughout this application various references are referred to within parentheses or with arabic numerals within parenthesis. Full bibliographic citations for these publications referred to by arabic numerals may be found at the end of the specification immediately preceding the claims. The disclosures of these publications in their entireties are hereby incorporated by reference into this application to more fully describe the state of the art to which this invention pertains.

Human enteroviruses belonging to the family Picornaviridae are characterized by a single-stranded positive RNA genome. Members of this viral family include poliovirus, echoviruses, coxsackieviruses and rhinoviruses. Among these viruses, poliovirus has been the most extensively studied.

Poliovirus is known to be the causative agent of poliomyelitis, a paralytic disease of the central nervous system. This virus is known to exist in three stable serotypes—1, 2 and 3. For over 25 years, this disease has been controlled by the use of both the Sabin oral live-attenuated vaccine and the Salk inactivated virus vaccine. The Sabin vaccine consists of attenuated virus of each serotype, none of which are capable of causing disease. The strains used to produce the vaccine were created by a combination of extensive in vivo and in vitro passage of each of the three wild-type strains through monkey tissue. Upon oral administration, the live virus contained in the Sabin vaccine replicates in the gut, thereby inducing both systemic and local immunity. The killed virus (Salk) vaccine, which is administered intramuscularly, is limited to inducing systemic immunity.

Although the Sabin vaccine is considered to be a safe and effective protection against poliomyelitis, a small number of recipients have developed vaccine-associated the disease.

In an effort to understand the molecular basis of attenuation and reversion, the nucleotide sequences of cDNAs corresponding to each of the 3 attenuated strains and their wild-type progenitors, were compared [A. Nomoto et al., "Complete Nucleotide Sequence of the Attenuated Sabin 1 Strain Genome", *Proc. Natl. Acad. Sci. USA,* 79, pp. 5793–97 (1982); G. Stanway et al., "Nucleic Acid Sequence of the Region of the Genome Encoding Capsid Protein VP1 of Neurovirulent and Attenuated Type 3 Polioviruses", *Eur. J. Biochem.,* 135, pp. 529–33 (1983); G. Stanway et al., "Comparison of the Complete Nucleotide Sequences of the Genomes of the Neurovirulent Poliovirus P3/Leon/37 and its Attenuated Sabin Vaccine Derivative P3/Leon 12ab", *Proc. Natl. Acad, Sci. USA,* 79, pp. 1539–43 (1984); and H. Toyoda et al., "Complete Nucleotide Sequences of All Three Poliovirus Serotype Genomes", *J. Mol. Biol.,* 174 pp. 561–585 (1984)]. The observed differences in nucleotide sequence between each wild-type progenitor and its resultant attenuated strain were then further analyzed to determine their relationship to the phenomenon of attenuation.

In serotype 3, for example, the attenuated strain differed from the wild-type strain by only 10 point mutations [G. Stanway et al., (1984), supra]. Of these differences, only the changes at nucleotide positions 472 and 2034 were thought to be strongly associated with attenuation [D. M. A. Evans et al., "Increased Neurovirulence Associated With A Single Nucleotide Change In A Noncoding Region of the Sabin Type 3 Poliovirus Genome", *Nature,* 314, pp. 548–50 (1985); G. D. Westrop et al., "Genetic Basis of Attenuation of the Sabin Type 3 Oral Poliovirus Vaccine", *J. Virol.,* 63, pp. 1338–44 (1989)].

Prior to the identification of the nucleotides which are linked to attenuation, it was demonstrated that cDNA synthesized from a viral RNA template ("RNA virus cDNA") could be utilized to produce viable poliovirus following transfection of mammalian cells [V. R. Racaniello et al., "Cloned Poliovirus Complementary DNA Is Infectious In Mammalian Cells", *Science,* 214, pp. 916–19 (1981)]. Such observations created the possibility of producing improved polio vaccines via genetic engineering techniques. This could be achieved by altering the cDNA around the crucial nucleotides so as to minimize reversion to the wild-type nucleotide, while maintaining structural and functional integrity of the virus.

Despite the discovery that RNA virus cDNA can be used to produce viable virus, it has never been demonstrated that these cDNA are accurate copies of the viral RNA present in wild-type or vaccine virus. Moreover, the use of cDNA sequences to determine which nucleotides are linked to attenuation, may have caused one or more critical sites to have been overlooked. This is because the process used to produce cDNA, namely reverse transcription, is known to be errorprone [I. M. Verma, "Reverse Transcriptase", In *The Enzymes,* Vol. 14, P. D, Boyer, ed., Academic Press, New York, pp. 87–104 (1981)].

Accordingly, a need still exists for the production of RNA virus cDNAs which are truly complementary to the vaccine virus RNA. Moreover, the use of inaccurate RNA virus cDNAs may result in reduced attenuation, if these cDNAs are ultimately to be used to produce vaccines, such as polio vaccines.

The genome of poliovirus is a single-stranded RNA molecule of plus-sense that is approximately 7500 nucleotides in length. The error frequency associated with replication of single-stranded RNA, as for poliovirus, is especially high compared to that of double-stranded DNA (3). Due to this inherent property, every preparation of poliovirus including the original Sabin (SO) strains must be considered genotypically heterogeneous.

Culture conditions (ie. temperature, cell substrate) as well as the homogeneity of the input virus are likely to influence which genotype predominates during amplication of a poliovirus sample. It is therefore not surprising that authorities who regulate the manufacture of OPVs (ie. FDA and WHO) dictate strict guidelines regarding the production of manufacturing seeds as well as the passage level of the seed represented in vaccine (22, 26). These regulations were put into action as an effort to minimize selection and amplification of less attenuated variant strains.

It has been well documented that the attenuated phenotype of the Sabin 3 strain is less genetically stable than the type 1 and 2 vaccine strains (4, 7, 11). In the past, a new manufacturing seed (RSO) was derived from the original Sabin 3 virus by selecting a plaque produced in Vervet monkey kidney cell monolayers from extracted infectious RNA (19). The isolate was chosen based on increased stability of its sensitivity to grow at 40.3° C. (rct marker) during serial passage as well as increased attenuation in monkeys. The sensitivity of growth at temperatures above 37° (rct marker) is still employed as an in vitro biological test to analyze the quality of vaccine strains (13).

A report by Kohara et al. (9) suggested that an infectious cDNA clone might be used to preserve the constancy and quality of the Sabin 1 seed. It is plausible that a similar approach could also benefit the attenuated type 3 strain. Until recently, the literature contained two cDNA sequences for Sabin 3 which differed at nucleotide positions (17, 21). The divergence between these sequences may be due to the fact that passage derivatives and clonal isolates of Sabin 3 rather than actual vaccine virus were used for making the cDNA clones.

SUMMARY OF THE INVENTION

This invention also provides a vaccine useful for immunizing a subject, for example a human, against infectious poliovirus, wherein the vaccine comprises an effective amount of an RNA virus, produced by transforming a suitable host cell with a recombinant nucleic acid sequence which encodes for the virus; and isolating the virus so produced, effective to immunize the subject.

Further provided by this invention is a method of immunizing a subject such as a human against infectious poliovirus, wherein the method comprises administering to the subject a suitable dose of the vaccine described hereinabove.

BRIEF DESCRIPTION OF THE DRAWINGS

FIG. 3 depicts the strategy for assembling partial cDNAs into a single, full-length P3/Sabin cDNA according to this invention.

In order to reconstruct pLED3 with the correct number of A's, the SacI/HindIII fragment from pLL3-271 used above was cloned into bacteriophage M13 for oligonucleotide-directed deletion mutagenesis. An oligonucleotide spanning nucleotides 4121–4150 was synthesized for this purpose. The oligonucleotide has the sequence: 5'-CGCCTCAGTAAATTTTTCAACCAACTATC-3' (SEQ ID NO. 3).

Mutagenesis was performed using a "T7-GEN In Vitro Mutagenesis Kit" (United States Biochemical, Cleveland, Ohio) and following the manufacturer's directions. The mutagenized insert was called CB2 and was demonstrated to possess six A's at positions 4133–4138 as well as C at 2493 by sequence analysis. The corrected full-length construct was made by ligating the SacI/HindIII fragment of CB2 to the SacI/HindIII partial digestion fragment of pVR318 which had been used in the original pLED3 construction. The product of this ligation was called pLED3.2. The entire cDNA sequence of pLED3.2 has been verified to match the sequence reported in FIGS. 6A–6J.

FIGS. 6A–6J, (SEQ ID NO. 1–2) depict the nucleotide sequence of a true type 3 poliovirus vaccine strain cDNA according to this invention.

Figure 7A:
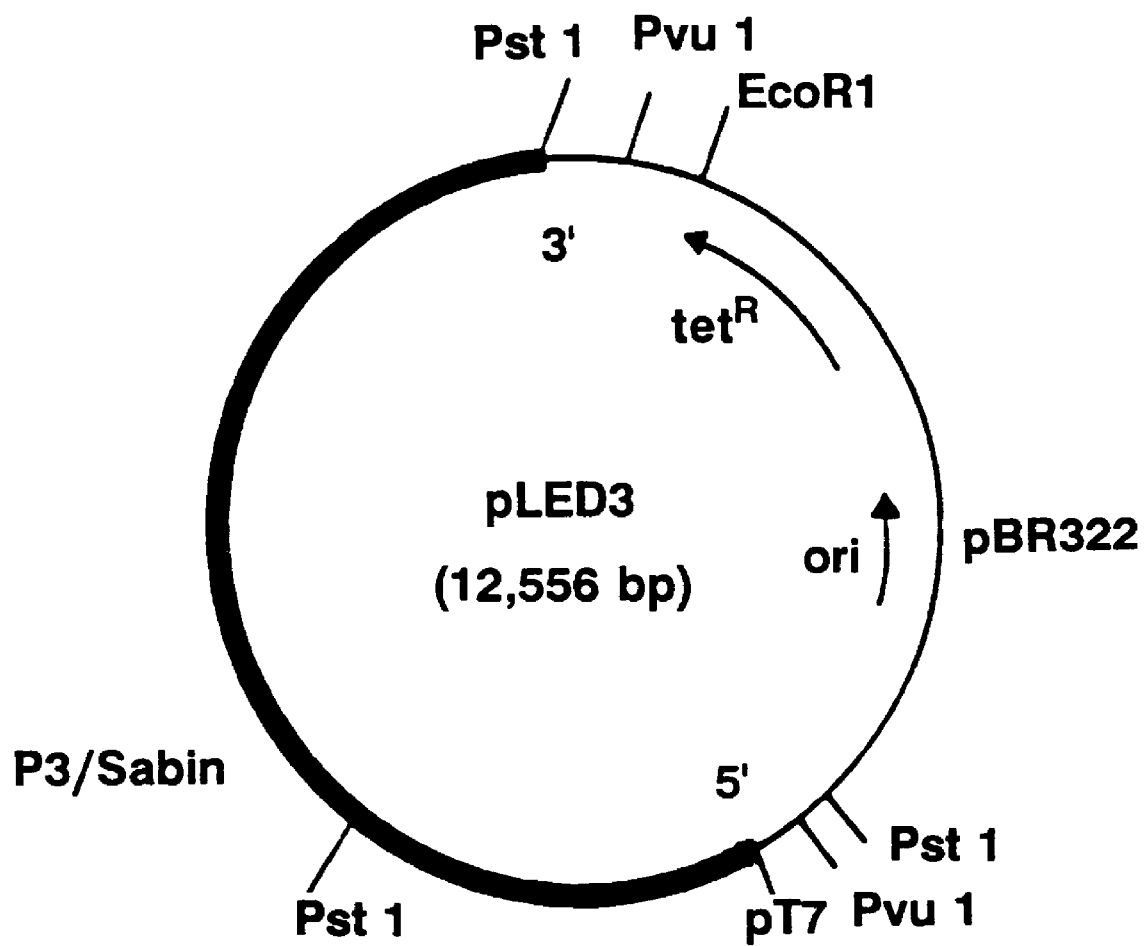
Figure 7B:
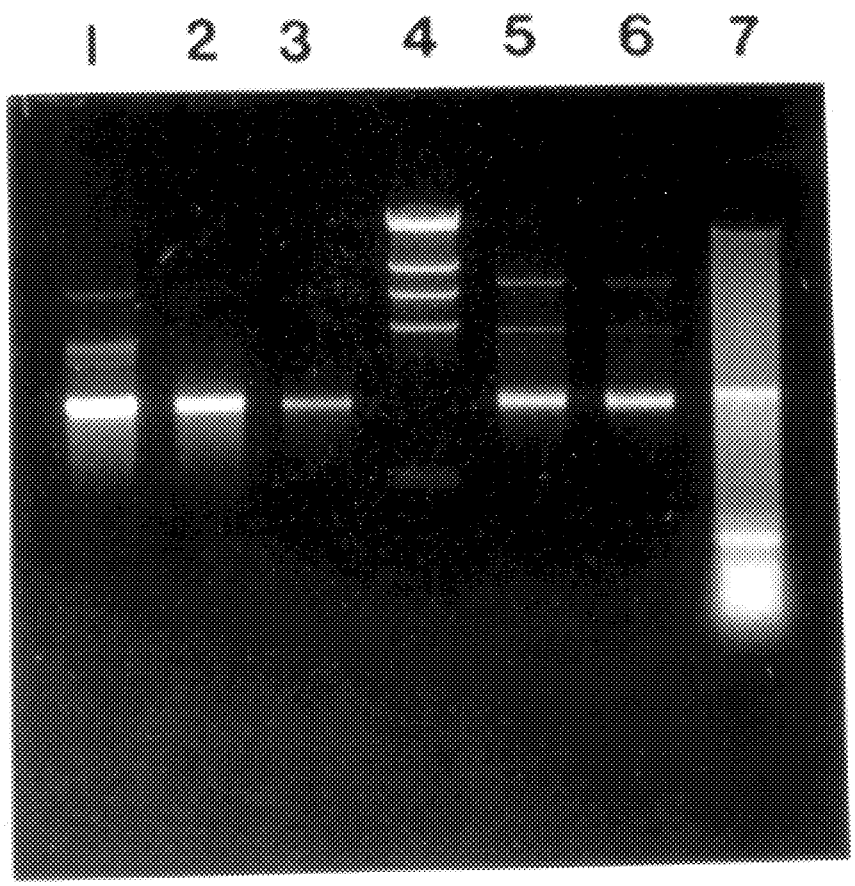

FIGS. 7A and 7B. FIG. 7A depicts the structure of the plasmid containing full-length LED3 cDNA and the T7 RNA polymerase promoter. The large shaded area represents the poliovirus cDNA. The small open area indicates the T7 promoter (pT7) and the start site for in vitro positive polarity transcripts of the cDNA. The plasmid is cut with PvuI (sites shown) before run-off transcripts are synthesized. FIG. 7B depicts RNAs transcribed from cDNA clones by purified T7 RNA polymerase. Portions of the transcription reaction mixture were analyzed by electrophoresis in a 0.6% agarose gel as described in Materials and Methods, Example 13. Lanes 1–3 represent 0.75 µg, 0.50 µg and 0.25 µg of 7.5 kb ssRNA marker, respectively. HindIII-digested phage lambda DNA is shown in lane 4. Lanes 5 & 6 demonstrate transcription reactions containing PvuI-digested pLED3 and pVR318 templates, respectively. RNA extracted from pelleted virions is shown in lane 7.

FIG. 8, depicts SDS-polyacrylamide gel electrophoresis of LED3 and VR318 cDNA-derived viruses. A [$^{35}$S] methionine-labeled sample was prepared and loaded in each lane and resolved by eletrophoresis as described hereafter. The gel was dried and the protein bands visualized by autoradiography. LED3 virus in lanes "A"; VR318 virus in lanes "B". The positions of prestained molecular mass markers (kilodaltons) are indicated on the left. Positions of viral capsid proteins are identified on the right.

Figure 9A:
Figure 9B:
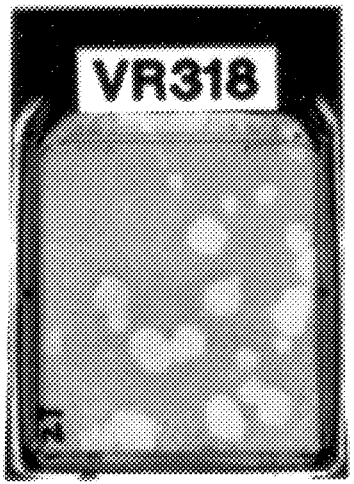
Figure 9C:
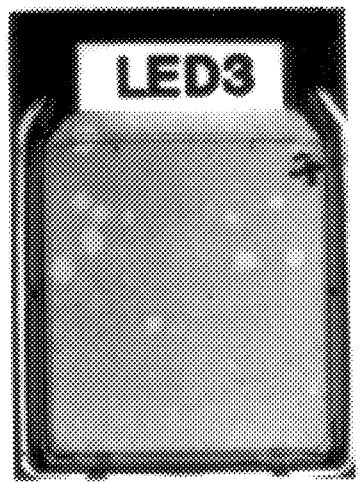

FIGS. 9A–9C, depict plaque phenotype of Leon (wild-type), VR318 and LED3 viruses on Vero cells. After incubation at 33.5° C. for 3 days under 1.0% nutrient agar, cells were stained with neutral red to visualize plaques.

Figure 10:
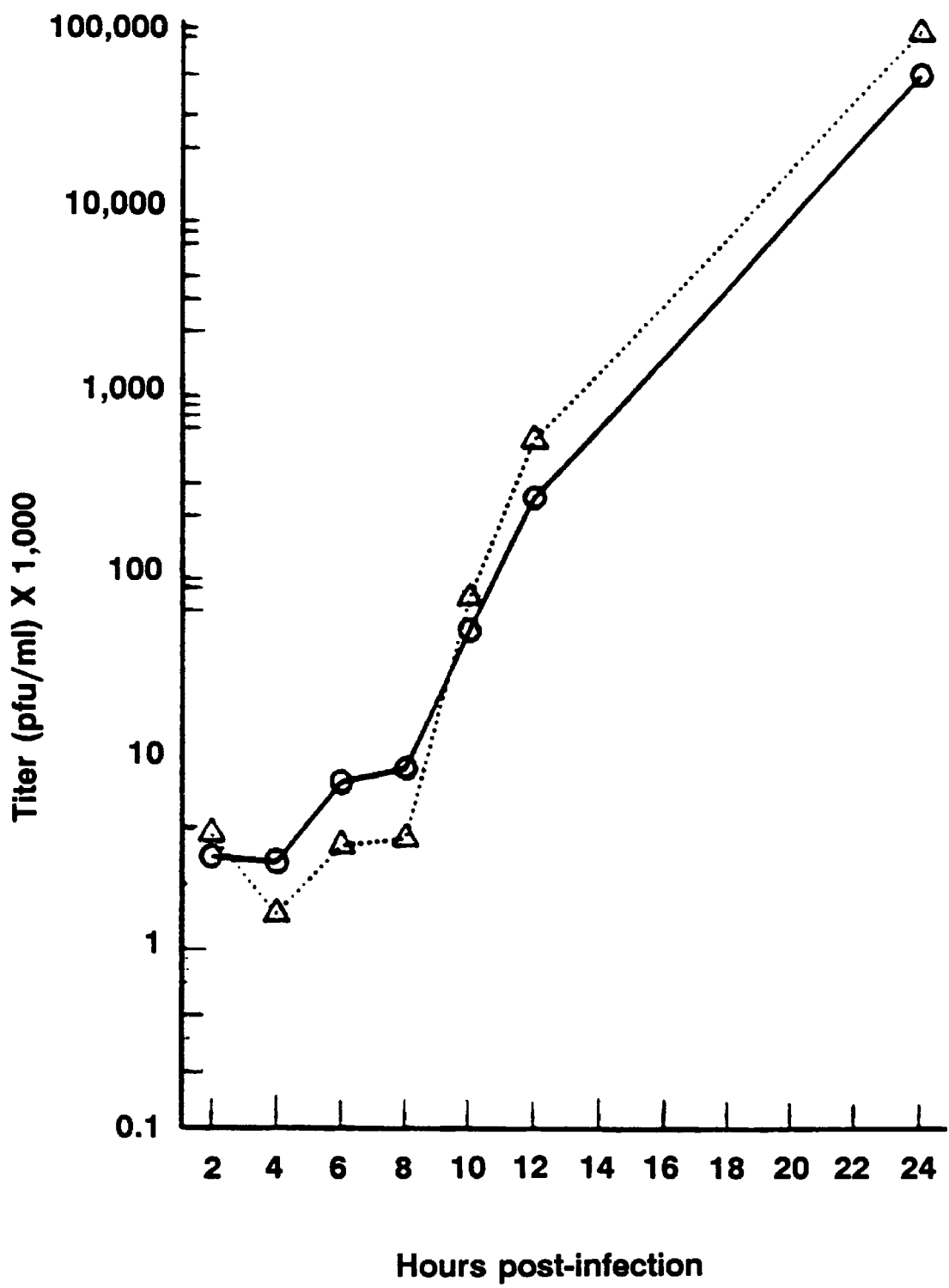

FIG. 10, depicts kinetics of virus growth at 33.5° C. Vero cell monolayers were infected at an MOI of 4, and the extracellular medium was harvested at the indicated times post-infection. Plaque assays were used to determine the titer of infectious particles per ml as described in Materials and Methods, Example 13.

o————————o, LED3; Δ — — — — — — — Δ, VR318.

Figure 11:
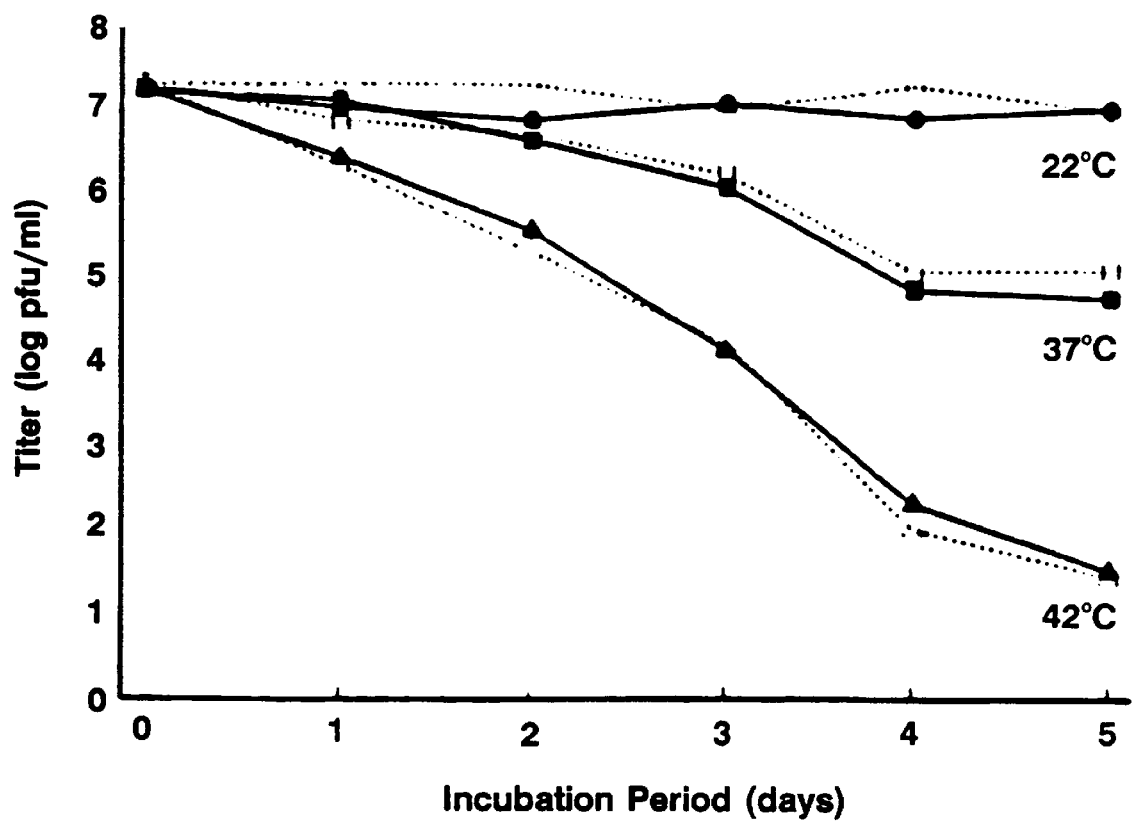

FIG. 11, depicts thermal stability of LED3 and VR318 virus at various temperatures. Virus samples containing approx. 10$^{7.3}$ pfu/ml were incubated at 22° C. (circle), 37° C. (square) and 42° C. (triangle). Samples were periodically removed and titer of infectious virus determined by plaque assays. Open markers, LED3; filled markers VR318.

DETAILED DESCRIPTION OF THE INVENTION

This invention provides a method for producing a true RNA virus cDNA comprising the steps of (a) isolating genomic RNA from an RNA source virus; (b) employing RNA sequencing means to determine the nucleotide sequence of a portion of the isolated genomic RNA; (c) employing cDNA synthesis means to produce a double-stranded cDNA from the isolated genomic RNA; (d)

employing DNA sequencing means to determine the nucleotide sequence of a portion of the cDNA, wherein the portion of the cDNA corresponds to the portion of the RNA sequenced in step (b); (e) comparing the sequenced cDNA with the sequenced RNA to determine substantive differences in nucleotide sequence; and (f) altering the substantive differences in the cDNA to produce a true RNA virus cDNA.

This invention also provides a method for producing an RNA virus cDNA comprising the steps of a) isolating genomic RNA from an RNA source virus, b) employing RNA sequencing means to determine the nucleotide sequence of a portion of said isolated genomic RNA, c) employing cDNA synthesis means to produce a double-stranded cDNA from said isolated genomic RNA, d) employing DNA sequencing means to determine the nucleotide sequence of a portion of said cDNA, wherein said portion of said cDNA corresponds to said portion of said RNA sequenced in step b), e) comparing said sequenced cDNA with said sequenced RNA to determine substantive differences in nucleotide sequence, and altering said substantive differences in said cDNA to produce an RNA virus cDNA.

This invention also provides the methods described hereinabove, wherein the RNA source virus is a Picornavirus, such as a vaccine strain 3 poliovirus. In one embodiment of the invention, the portion of RNA sequenced in step (b) comprises nucleotide 2493 of a vaccine strain 3 poliovirus. In a further aspect of this embodiment, the RNA consists of about 100 to 200 nucleotides. Alternatively, the nucleotide sequence of the entire isolated viral RNA is determined in step (b).

This invention further provides a true RNA virus cDNA or an RNA virus cDNA produced by the methods described hereinabove. For example, a true RNA virus cDNA or an RNA virus cDNA may be produced which is derived from a vaccine strain 3 poliovirus, the cDNA being selected from that contained in a novel plasmid designated pLED3.2 or pLED3, respectively or cDNAs which code on expression for the polypeptides coded on for expression by pLED3.2 or pLED3, respectively and the recombinant DNA molecule produced thereby.

The recombinant DNA molecule can be operatively linked to a promoter of RNA transcription. Suitable promoters include, but are not limited to the T7 promoter.

A host transformed with a recombinant DNA molecule described hereinabove is also provided by this invention, wherein the host is selected from the group consisting of bacteria, such as E. coli, yeast and other fungi, insect cells and animal cells. Suitable animal cells include, but are not limited to Vero cells, HeLa cells, COS cells, CV-1 cells and primary monkey kidney cells.

Further provided by this invention is a method for producing a viable RNA virus comprising the steps of: (a) culturing a host described hereinabove under conditions which permit the production of viable RNA virus; and (b) harvesting the viable RNA virus from the host cell culture.

This invention provides a method of producing a viable RNA virus comprising the steps of: (a) employing in vitro transcription means to produce RNA from a recombinant DNA molecule described hereinabove (b) isolating the RNA; (c) transfecting a host with the isolated RNA, wherein the host is an animal cell; (d) culturing the host under conditions which permit the production of viable RNA virus; and (e) harvesting the viable RNA virus from the host cell culture. For example, vaccine strain 3 poliovirus may be used and the host may be a primary monkey kidney cell.

This invention further provides a method of producing a viable RNA virus comprising the steps of: (a) transfecting a host with RNA virus cDNA, wherein the cDNA is selected from that contained in the plasmid pLED3 or pLED3.2 or cDNAs which code on expression for the polypeptides coded on for expression by pLED3 or pLED3.2, wherein said host is an animal cell; (b) culturing said host under conditions which permit the production of viable RNA virus from said host cell culture.

This invention further provides an RNA virus, produced by transforming a suitable host cell with a recombinant nucleic acid sequence which encodes for the virus; culturing the host cell under conditions which permit the production of virus; and isolating the virus so produced.

In one embodiment of this invention, the RNA virus may be a vaccine strain 3 poliovirus and the recombinant nucleic acid sequence is a recombinant infectious full length nucleic acid sequence which encodes for the virus; culturing the host cell under conditions which permit the production of virus; and isolating the virus so produced.

In one embodiment of this invention, the RNA virus may be a vaccine strain 3 poliovirus and the recombinant nucleic acid sequence is a recombinant infectious full length nucleic acid sequence which encodes for the vaccine strain 3 poliovirus.

A method of screening for variants of a strain 3 poliovirus is also provided which comprises the steps of: (a) isolating genomic RNA from the poliovirus; (b) employing RNA sequencing means to determine the nucleotide at position 2493.

This invention also provides a method for increasing the attenuation of a strain 3 poliovirus encoded by an RNA virus cDNA, wherein the cDNA comprises the nucleotide sequence ATT at positions 2492 to 2492, the method comprising the step of mutagenizing the cDNA at nucleotide 2493 to change the T to C. In one embodiment of the invention, the method can further comprise the step of mutagenizing the cDNA at nucleotide 2494 to change the T to a nucleotide selected from the group consisting of A, C and G.

This invention provides a vaccine useful for immunizing a subject, for example a human, against infectious poliovirus, wherein the vaccine comprises an effective amount of an RNA virus, produced by transforming a suitable host cell with a recombinant nucleic acid sequence which encodes for the virus; culturing the host cell under conditions which permit the production of virus; and isolating the virus so produced, effective to immunize the subject, and a suitable carrier. The RNA virus may be a vaccine strain 3 poliovirus and the recombinant nucleic acid sequence is a recombinant infectious full length nucleic acid sequence which encodes for the vaccine strain 3 poliovirus.

The recombinant nucleic acid sequence which encodes for the RNA virus may be a DNA sequence, or an RNA sequence or in the preferred embodiment of this invention, the recombinant nucleic acid sequence is a cDNA sequence. Suitable cDNAs are the plasmids designated pLED3.2 or pLED3, each of which contains a promoter linked cDNA nucleic acid sequence which encodes for the vaccine strain 3 poliovirus. The plasmid pLED3 was deposited with the American Type Culture Collection (ATCC), located at 12301 Parklawn Drive, Rockville Md., 20852, under the provisions of the Budapest Treaty on the International Recognition of the Deposit of Microorganisms for the Purposes of Patent Procedure. The plasmid pLED3 was assigned Accession No. 40789. The plasmid pLED3.2 also was deposited with the ATCC under the provisions of the Budapest Treaty and was assigned Accession No. 75062.

Suitable host cells include, but are not limited to bacteria, such as E. coli, yeast and other fungi, insect cells and animal cells.

Suitable animal cells include, but are not limited to Vero cells, HeLa cells, COS cells, CV-1 cells and primary monkey kidney cells.

The suitable carrier may be a physiologically balanced culture medium, such as aline containing stabilizing agents, for example, dextrose and lactose, or other nontoxic substances. These vaccines may also be formulated with a suitable adjuvant such as alum. For methods of vaccine preparation, see J. I. Duffy, Vaccine Preparation Techniques, Noyes Data Corporation (1980), and G. W. Warr, "Preparation of Antigens and Principles of Immunization", in J. J. Marchalonis and G. W. War. eds., Antibody As A Tool—The Applications of Immunochemistry, pp. 21–58, John Wiley & Sons (1982).

The RNA virus may also be desiccated, e.g., by freeze drying for storage or for subsequent formulation into liquid vaccines.

Further provided by this invention is a method of immunizing a subject such as a human against infectious poliovirus, wherein the method comprises administering to the subject a suitable dose of the vaccine described hereinabove. Suitable methods of administering vaccines are well known to those of ordinary skill in the art. However, by way of example, such methods may include but are not limited to intramuscular, intravenous, subcutaneous, intratracheal or intranasal administration.

Additionally, the effective immunizing amount is an amount which is necessary to invoke the production of antibodies by the subject thereby conferring protection on the subject against infectious poliovirus or poliomyelitis.

Throughout this application, references to specific nucleotides in cDNA molecules are to nucleotides present on the coding strand of the cDNA, i.e., the strand which has a sequence equivalent to the position RNA strand of an RNA virus. References to specific nucleotide position numbers in strain 3 poliovirus follow the nucleotide numbering system of G. Stanway et al., "Comparison of the Complete Nucleotide Sequences of the Genomes of the Neurovirulent Poliovirus P3/Leon/37 and its Attenuated Sabin Vaccine Derivative P3/Leon 12alb", Proc. Natl. Acad. Sci. U.S.A., 81, pp 1539–43 (1984). The following standard abbreviations are used throughout the specification and in the claims to indicate specific nucleotides:

C—cytosine
A—adenosine
T—thymidine
G—guanosine
U—uracil

The term "source virus" refers to the RNA virus from which RNA is isolated and used as a template for cDNA production. And the term "increased attenuation" is used throughout to indicate a lower rate of reversion to the neurovirulent phenotype than those of conventional vaccine virus strains.

The term "true RNA virus cDNA", as used herein, refers to a cDNA which directs the production of a viable RNA virus that is phenotypically similar to the source virus. Accordingly, the present invention encompasses cDNA molecules which, by virtue of the redundancy of the genetic code, are characterized by a nucleotide sequence that differs from that of the source virus RNA, but which encode polypeptides having the same amino acid sequences as those encoded by the source virus RNA. The invention also encompasses cDNAs which encode amino acid sequences which differ from those of the source virus polypeptides, but which do not produce phenotypic changes. Hereinafter, these altered, but phenotypically equivalent amino acid sequences are referred to as "equivalent amino acid sequences." And this invention encompasses cDNA molecules characterized by changes in non-coding regions that do not alter the phenotype of the RNA virus produced therefrom when compared to the source virus. Differences between the nucleotide sequence of an RNA virus cDNA and the source virus RNA which result in phenotypical differences in the virus produced therefrom are hereinafter referred to as "substantive differences".

This invention provides a method for producing an RNA virus cDNA comprising the steps of (a) isolating genomic RNA from an RNA source virus, (b) employing RNA sequencing means to determine the nucleotide sequence of a portion of the isolated genomic RNA, (c) employing cDNA synthesis means to produce a double-stranded cDNA from the isolated genomic RNA, (d) employing DNA sequencing means to determine the nucleotide sequence of a portion of the cDNA, wherein the portion of the cDNA corresponds to the portion of the RNA sequenced in step (b), (e) comparing the sequenced cDNA with the sequenced RNA to determine substantive differences in nucleotide sequence, and (f) altering the substantive differences in the cDNA to produce an RNA virus cDNA. In one embodiment of this invention, the RNA virus is a true RNA virus and in another embodiment of this invention the RNA virus is a "phenotypically equivalent" virus. In one embodiment of this invention, the RNA source virus is a Picornavirus, for example a vaccine strain 3 poliovirus.

This invention also provides a method as described hereinabove wherein the portion of RNA sequenced in step (b) comprises nucleotide 2493 of a vaccine strain 3 poliovirus, or preferably, wherein the RNA consists of about 100 to 200 nucleotides.

In another embodiment of this invention, the method described hereinabove wherein the nucleotide sequence of the entire isolated viral RNA is determined in step (b).

The method of this invention may also be used to produce an RNA virus cDNA by altering nucleotides in various regions of the poliovirus genome, for example, to correct mutations introduced into the region coding for the amino terminus of VP1 of the type 1 Mahoney poliovirus [K. Kirkegaard, "Mutations in VP1 of Poliovirus Specifically Affect Both Encapsulation and Release of Viral RNA", J. Virology, 64, pp. 195–206 (1990)].

Further provided by this invention is an RNA virus cDNA produced by any of the methods described hereinabove which may include, but is not limited to an RNA virus cDNA derived from a vaccine strain 3 poliovirus, the cDNA being selected from the group consisting of pLED3 or pLED3.2 and cDNAs which code an expression for the polypeptides coded on for expression by pLED3 or pLED3.2.

This invention also provides a recombinant DNA molecule comprising an RNA virus cDNA as described hereinabove, which may include, but is not limited to the recombinant DNA molecule wherein the RNA virus cDNA is operatively linked to a promoter of RNA transcription such as the T7 promoter.

A host transformed with a recombinant DNA molecule described hereinabove is also provided wherein the host is selected from the group consisting of bacteria, yeast and other fungi, insect cells and animal cells. In a preferred embodiment of this invention, the host is an animal cell and is selected from the group consisting of Vero cells, HeLa cells, COS cells, CV-1 cells and primary monkey kidney cells. In another embodiment of this invention, the host is $E.$ $coli$.

This invention further provides a method for producing a viable RNA virus comprising the steps of: culturing a host described hereinabove under conditions which permit the production of viable RNA virus and harvesting the viable RNA virus from the host cell culture. This invention also provides a method of producing a viable RNA virus comprising the steps of employing in vitro transcription means to produce RNA from a recombinant DNA molecule described hereinabove, isolating the RNA, transfecting a host with the isolated RNA, wherein the host is an animal cell, culturing the host under conditions which permit the production of viable RNA virus and harvesting the viable RNA virus from the host cell culture. In the preferred embodiment of this invention, the RNA virus is a vaccine strain 3 poliovirus and the host is a primary monkey kidney cell.

A method of screening for variants of a strain 3 poliovirus is provided by this invention which comprises the steps of isolating genomic RNA from the poliovirus, and employing RNA sequencing means to determine the nucleotide at position 2493.

This invention also provides a method for increasing the attenuation of a strain 3 poliovirus encoded by an RNA virus cDNA, wherein the cDNA comprises the nucleotide sequence ATT at positions 2492 to 2494, and the method comprising the step of mutagenizing the cDNA at nucleotide 2493 to change the T to C. This method may further comprise the step of mutagenizing the cDNA at nucleotide 2494 to change the T to a nucleotide selected from the group consisting of A, C and G.

The determination of phenotypic differences may be carried out by several methods which are well known in the art. Preferably, a true RNA virus cDNA of an attenuated strain 3 poliovirus encodes a virus which has the same degree of attenuation as the source virus. Several well characterized markers can be used to determine phenotypic changes in a strain of poliovirus. These are the "d" markers, which regulate the ability of the virus to grow under acid conditions [M. Vogt et al., "Mutants of Poliomyelitis Viruses with Reduced Efficiency of Plating in Acid Medium and Reduced Neuropathogenicity", $Virology$, 4, pp. 141–55 (1957)]; and the "$rct_{40}$" marker, which regulates the ability of the virus to grow at elevated temperatures [A. Lwoff, "Factors Influencing the Evolution of Viral Diseases at the Cellular Level and in the Organism", $Bact. Rev.$, 23, pp. 109–24 (1959)].

The most preferred method of determining phenotypic changes between an attenuated strain 3 source poliovirus and the virus produced from its true RNA virus cDNA is a comparison of neurovirulence. Several protocols for assessing neurovirulence are known in the art [Code of Federal Regulations, Title 21, Chapter 1, pp. 91–93 (Apr. 1, 1987 edition)].

Production of a True RNA Virus cDNA

According to one embodiment, the present invention relates to a method for producing true RNA virus cDNA. The production of a true RNA virus cDNA according to this invention may employ any RNA source virus—positive single-stranded, negative single-stranded, or double-stranded. Preferably, the source virus is a positive single-stranded virus. More preferably, the virus is a human enterovirus belonging to the family $Picornaviridae$. Most preferred is an attenuated type 3 vaccine strain poliovirus (also referred to herein as "P3/Sabin").

A. Proliferation and Isolation of Virus

The initial step in the production of true RNA virus cDNA involves the proliferation and purification of the source virus and the isolation of RNA therefrom. Techniques for proliferating and isolating virus are well known in the art [R. J. Kuchler, "Biochemical Methods in Cell Culture and Virology", Dowden, Hutchinson and Ross, Inc., Stroudsburg, Pa. (1977)]. It will be understood that the method of viral growth, including choice of host cell, selection of growth medium, and conditions of growth, will differ depending upon the particular source virus. In a preferred embodiment, attenuated strain 3 poliovirus is proliferated in primary monkey kidney cells according to known methods [A. Sabin et al., "Studies On Variants Of Poliomyelitis Virus", $J. Exp. Med.$, 99, pp. 551–76 (1954)]. The following procedures are applicable for any strain of poliovirus. However, the use of an alternate RNA source virus in these procedures may require certain virus-specific modifications which are known to those of skill in the art.

Viral proliferation of the RNA virus is allowed to proceed to a point where a sufficient quantity of virus can be harvested for RNA isolation. The culture media containing the source virus is then collected and cellular debris is removed, preferably by centrifugation at a speed which will not pellet the virus. This is typically about 2,500 rpm for about 20 minutes. The supernatant may then be further purified by ultrafiltration employing a filter having a pore size that is larger than the viral particles. Preferably, a filter of approximately 0.22 $\mu$M is used.

Following filtration, the viral particles are collected by polyethylene glycol precipitation followed by centrifugation or, more preferably, by high speed centrifugation at about 70,000 rpm. The viral particles are then resuspended in a small volume of buffer, preferably TNE (10 mM Tris-HCl, 100 mM NaCl, 1 mM EDTA, pH 7.4). A non-ionic detergent may optionally be added to the viral particle suspension to dissolve any contaminants. Although the high speed viral pellet is sufficiently pure to use as a source of viral RNA the viral suspension may optionally be further purified by sucrose density gradient centrifugation.

If density gradient centrifugation is employed, fractions are collected from the gradient and analyzed for the presence of source virus. Any conventional assay which detects source virus-specific proteins may be employed. Such assays include, for example, Western blots, ELISA, radioimmunoassay, or polyacrylamide gel electrophoresis and comparison to a source virus standard. The latter technique is most preferred because it is the most economical.

B. Isolation and Sequencing of Viral RNA

Once the virus is purified as described above, viral RNA may then be isolated. This is achieved by first dissociating the viral capsid proteins by treatment with detergent, preferably sodium dodecyl sulfate ("SDS") at a final concentration of 0.5%. The dissociated proteins are then extracted by treatment of the sample with organic solvents. Extraction is preferably achieved with a phenol:chloroform:isoamyl alcohol mixture. The RNA present in the aqueous phase may then be isolated by any method well known in the art [T. Maniatis, "The Molecular Guide To Cloning", Cold Spring Harbor Press (1983)]. Preferably, the viral RNA is precipitated with 0.5 volumes of 7.5 M ammonium acetate and 2.5 volumes of ethanol at −20° C. Quantitation and integrity of the viral RNA may be determined by agarose gel electrophoresis. It should be noted, as is well known in the molecular biology art, that great care must be taken in the preparation and handling of RNA samples due to the prevalence of RNases. Methods for inactivating RNases that may be present in reagents and in vessels used in RNA preparation are well known [T. Maniatis, supra].

Once the source virus RNA has been isolated, it is subjected to dideoxy nucleotide sequencing [F. Sanger et al., "DNA Sequencing With Chain-Terminating Inhibitors", *Proc. Natl. Acad. Sci. USA,* 74: 5463–67 (1977)] employing modifications for RNA [D. C. Deborde et al., "Resolution Of A Common RNA Sequencing Ambiguity By Terminal Deoxynucleotidyl Transferase", *Anal. Biochem.,* 157, pp. 275–82 (1986)]. According to a preferred embodiment of this invention, the entire RNA genome of the virus is sequenced and compared to the cDNA sequence by methods which are hereinafter described. In this embodiment of the invention the source virus is most preferably an attenuated type 3 vaccine strain poliovirus.

C. Synthesis and Screening of an RNA Virus cDNA Library

Following RNA sequencing, the source virus RNA is used as a template for the synthesis of a full-length, double-stranded cDNA. Any well-known method or commercially available cDNA synthesis kit is employed to synthesize cDNA. Preferably, cDNA is synthesized by the method of V. R. Racaniello et al., "Molecular Cloning Of Poliovirus cDNA And Determination Of The Complete Nucleotide Sequence Of The Viral Genome", *Proc. Natl. Acad. Sci. USA,* 78, pp. 4887–91 (1981). For ease of detection, the first strands of cDNA may optionally be radiolabeled by employing a radioactive nucleotide during cDNA synthesis. Once synthesized, the single-stranded cDNA are preferably size-fractionated either by agarose gel electrophoresis or, more preferably, by gel chromatography. The larger cDNAs are isolated and used as templates for second-strand synthesis. Double-stranded cDNA is then size-fractionated as described above and the largest molecules are used for the creation of a source virus cDNA library. The cDNA are then tailed, either by the olio dG/dC method or by the addition of restriction enzyme linkers, and cloned into an appropriate vector. The choice of vector will be based upon the technique that will be employed to screen the library. For example, the use of an immunoscreening technique requires that the cDNA be inserted into an expression vector, such as lambda gt11 (ATCC accession number 37194). If a hybridization screening method is employed, vectors such as bacterial plasmids are most convenient. Preferably, the cDNA are tailed by the olio dG/dC method and cloned into the PstI site of pBR322.

Once the RNA virus cDNA library is created, it is screened o for a full-length cDNA clone. This may be achieved by well-known screening methods, such as antibody screening or hybridization to a labeled probe. Most preferably, the library is screened by colony hybridization using virus-specific cDNA probes [M. Grunstein et al., "Colony Hybridization: A Method for the Isolation of Cloned DNAs That Contain A Specific Gene", *Proc. Natl. Acad. Sci. USA,* 72, pp. 3961–65 (1975)], based on known nucleotide sequences or amino acid sequences of the virus. Once a clone containing an RNA virus cDNA has been identified and isolated, it may be removed from the vector and analyzed to determine whether it represents a full-length RNA virus cDNA. In a preferred embodiment of the invention, the dC-tailed cDNA is removed from a Pst I cut, dG-tailed vector by digestion with PstI. Partial cDNAs may be used to reprobe the library and to locate longer, or full-length cDNAs. If no full-length cDNAs can be detected, several overlapping partial cDNAs representing the entire source virus genome may be ligated together at common restriction sites to produce a full-length cDNA [V. R. Racaniello et al., "Cloned Poliovirus cDNA Is Infections In Mammalian Cells", *Science,* 214, pp. 916–19 (1981)]. Any portion of the viral genome which is not represented by an isolated cDNA may be synthesized using standard oligonucleotide synthesizing techniques and subsequently ligated into its proper position to form a full-length cDNA.

D. Sequencing and Alteration of cDNA to Correspond to Source Virus RNA

Portions of the full-length cDNA corresponding to the sequenced portion of the source virus RNA are then sequenced by standard DNA sequencing methods. The sequenced regions of the viral RNA and the RNA virus cDNA are then compared. Theoretically, the cDNA should correspond exactly to the RNA which served as its template. However, it is known that reverse transcriptase can produce errors when transcribing cDNA from RNA [I. M. Verma, "Reverse Transcriptase", In *The Enzymes,* Vol. 14, P. D. Boyer, ed., Academic Press, New York, pp. 87–104 (1981)]. Therefore, according to the method of this invention, it is necessary to alter the nucleotide sequence of the cDNA so that it corresponds to the sequenced RNA.

The present invention contemplates altering the cDNA sequence at those sites which are responsible for phenotypic changes. Accordingly, portions of the cDNA which encode polypeptides having equivalent amino acid sequences as those encoded by the source virus RNA need not be altered.

Preferably, any cDNA nucleotide mutation which may potentially affect virus production or viral polypeptide synthesis should be altered to correspond to the source virus RNA.

Methods for altering the nucleotide sequence of a cDNA molecule are known in the art and include site-directed mutagenesis [C. A. Hutchinson, III et al., "Mutagenesis At A Specific Position In A DNA Sequence", *J. Bio. Chem.,* 253, pp. 6551–60 (1978); A. Razin et al., "Efficient Correction Of A Mutation By Use Of A Chemically Synthesized DNA", *Proc. Natl. Acad. Sci. USA,* 75, p. 4268 (1978)]. Alternatively, a partial cDNA clone containing the desired sequence may be isolated from the cDNA library and its DNA, or a portion thereof, substituted in the full-length clone for the sequences which are to be altered. Once the cDNA sequence has been altered, it is utilized in other embodiments of this invention.

According to another embodiment of the present invention, the true RNA virus cDNA may be inserted into an appropriate vector and used to transform an appropriate host. The choice of vector will depend upon the ultimate intended use of the cDNA. Similarly, the choice of host will depend upon both the vector selected and the ultimate goal of transformation.

For example, if it is desirable to simply store the cDNA and create and unlimited supply thereof, the cDNA will be inserted into a vector which is capable of transforming a unicellular organism, such as a bacteria, yeast or other fungi, an animal cell or an insect cell. According to one embodiment of this invention, the cDNA is inserted into the PstI site of pBR322 and the host to be transformed is *E. coli.*

According to another embodiment of the invention, the true RNA virus cDNA may be operatively linked to a promoter of transcription. As used herein, the term "operatively linked" means positioned in such a manner that the promoter will direct the transcription of RNA off of the true virus cDNA. Examples of such promoters are SP6, T4 and T7. The most preferred promoter is the T7 promoter [J. J. Dunn et al., "Complete Nucleotide Sequence of Bacteriophage T7 DNA and the Locations of T7 Genetic Elements", *J. Mol. Biol.*, 166, pp. 477–535 (1983)]. Vectors which contain both a promoter and a cloning site into which an inserted piece of DNA is operatively linked to that promoter are well known in the art. Preferably, these vectors are capable of transcribing RNA in vitro. Examples of such vectors are the pGEM series [Promega Biotec, Madison, Wis.].

According to a further embodiment, the present invention relates to methods for producing viable positive stranded RNA virus. This may be achieved by transfecting an appropriate host with a true RNA virus cDNA. Any standard method of transfecting animal cells with DNA may be employed [F. M. Ausubel et al., "Current Protocols in Molecular Biology", Greene Publishing Associates & Wiley Intersciences (1987)]. The host is then cultured under conditions conductive to the production of RNA virus. Such conditions are well known in the art and will vary depending upon the virus to be produced. Similarly, the choice of host cell should be one which is compatible with the virus, preferably primate cells in culture. In a preferred embodiment of the invention, wherein the true RNA virus cDNA encodes an attenuated strain 3 poliovirus, the host is selected from the group consisting of Vero cells, HeLa cells, COS cells, CV-1 cells, human diploid cell lines, such as WI-38 and MRC5, and primary monkey kidney cells. The most preferred hosts are monkey kidney cells. Once the cells have produced a desirable level of virus, the virus is harvested from the cell culture according to standard protocols.

According to an alternative embodiment of this invention, viral RNA, which is produced by in vitro transcription of a true RNA virus cDNA according to the invention, may be employed in methods for producing viable RNA virus. The in vitro transcribed RNA is isolated by standard methods and used to transfect an appropriate host. The use of RNA to transfect cells is known in the art [S. van der Werf et al., "Synthesis of Infectious Poliovirus RNA by Purified T7 RNA Polymerase", *Proc. Natl. Acad. Sci. USA*, 83, pp. 2330–34 (1986)]. Once the cells are transfected, they are grown and the virus harvested according to standard protocols.

According to another embodiment, this invention relates to a method of screening for variants of a strain 3 poliovirus. Through RNA sequencing, it was discovered that the presence of a C at nucleotide position 2493 of this virus is linked to the attenuated strain 3 genotype. Previous analyses of this strain failed to recognize the importance of this position in attenuation due to a combination of two factors: the sequences of wild-type and attenuated strain 3 poliovirus were compared on the cDNA level, rather than the genomic RNA level; and some of these cDNAs were made from plaque isolates of the original viral samples [Stanway et al., "Comparison of the Complete Nucleotide Sequences of the Genomes of the Neurovirulent Poliovirus P3/Leon/37 and its Attenuated Sabin Vaccine Derivative P3/Leon 12alb", *Proc. Natl. Acad. Sci. USA*, 81, pp. 1539–43 (1984); H. Toyoda et al., "Complete Nucleotide Sequences of All Three Poliovirus Serotype Genomes", *J. Mol. Biol.*, 174, pp. 561–85 (1984)]. As a result of either errors in reverse transcription or mutations resulting from virus passaging, the cDNAs previously produced contained a T at position 2493. Therefore, the RNA of type 3 vaccine strain of poliovirus was mistakenly believed to contain U at this position, the same nucleotide present in the wild-type strain [Stanway et al., supra; H. Toyoda et al., supra]. Accordingly, position 2493 was never thought to contribute to the attenuation of the poliovirus strain 3 genome.

Therefore, the method of screening for variants of a strain 3 poliovirus according to this invention comprises the steps of sequencing the RNA of the virus and determining the nucleotide at position 2493. Most preferably, the portion of RNA to be sequenced consists of about 100–200 nucleotides flanking nucleotide 2493. This method may be used during amplification of the source virus (e.g., in vaccine production) to ensure maintenance of C at position 2493 in the viral genome.

This invention also relates to a method for increasing the attenuation of a strain 3 poliovirus produced from a true RNA virus cDNA, wherein the cDNA comprises the sequence ATT at positions 2492–2494. The method comprises mutagenizing the nucleotide at position 2493 from a T to a C and subsequently using the mutagenized cDNA to produce viable virus. The presence of a C instead of a U at position 2493 of strain 3 poliovirus RNA would be expected to alter the sixth amino acid of the viral capsid protein, VP1, from isoleucine to threonine, based on the genetic code. The condon encoding this amino acid spans nucleotides 2492–2494. Therefore, the method for increasing the attenuation of strain 3 poliovirus according to this invention may also include mutagenizing nucleotide 2494 from a T to either A, C or G.

In order that the invention described herein may be more fully understood, the following examples are set forth. It should be understood that these examples are for illustrative purposes only and are not to be construed as limiting this invention in any manner.

EXAMPLE 1
Purification Of A Strain 3 Poliovirus

All glassware utilized in the methods described below is either sterilized or treated with diethyl pyrocarbonate (DEP) to destroy RNases. All reagents are made up with water that had been treated with DEP prior to use.

Primary monkey kidney cells are infected with an attenuated strain 3 poliovirus, isolated by plaque purification from the "ORIMUNE" vaccine (Lederle Laboratories, Pearl River, N.Y.), at a low multiplicity of infection ("MOI"). The infected cultures are maintained at 34° C. in modified Earle's lacteal maintenance medium, pH 7.3, until the cell monolayer is destroyed (+4 cytopathic effect ("CPE")). The culture media (120 ml) is collected and centrifuged at 2,500 rpm for 20 minutes to remove any cellular debris. The supernatant is then filtered through a 0.22 $\mu$M Millex GV disc filter. The filtrate is then placed in quick seal high speed centrifuge tubes and spun in a 70.1 Ti rotor at 70,000 rpm for one hour at 4° C.

The virus pellet is resuspended in 4 ml of RNase-free TNE (10 mM Tris-HCl, 100 mM NaCl, 1 mM EDTA, pH 7.4) and the suspension transferred to a 15 ml polypropylene tube. The viral capsid are then dissociated by the addition of RNase-free SDS to a final concentration of 0.5%.

EXAMPLE 2
Isolation And Sequencing Of Viral RNA

Viral RNA is then isolated by extracting the dissolved capsid as prepared in Example 1, with an equal volume of phenol:chloroform:isoamyl alcohol (25:24:1). The aqueous layer is removed and re-extracted with the same organic solution. One-half volume of 7.5M ammonium acetate and 2.5 volumes of 100% ethanol is added to the aqueous extract and the RNA is precipitated at −20° C. for at least 30 minutes. The RNA is then pelleted by centrifugation at 12,000 rpm for 30 minutes. The RNA pellet is washed twice with ice-cold 70% ethanol, dried under vacuum and resuspended in 20 μM of water. The integrity and concentration of the RNA is estimated by using agarose gel electrophoresis.

The viral RNA is then sequenced essentially by the method of DeBorde [D. C. Deborde et al., *Anal. Biochem.*, 157, pp. 275–82 (1986)], the disclosure of which is incorporated here by reference. The specific details of sequencing are described below.

Approximately 500 mg of purified viral RNA is heat denatured at 100° C. for 3 minutes in 200 mM Tris-HCl, pH 8.3, 200 mM KCl, 20 mM $MgCl_2$, 10 mM DTT and then quick-chilled by immersion into an ice bath. Primer, dATP and enzymes are then mixed in with the RNA, as described by DeBorde et al. Two and one-half μl of primer-RNA mix is then combined with an equal volume of various reaction mixes, in separate tubes, to give the following component concentrations:

Tube A: 50 mM Tris-HCl, pH 8.3, 50 mM KCl, 5 mM MgCl, 10 mM DTT, 100 μM each of dCTP, dGTP and dTTP, 5 μCi [$^{35}$S]-dATP, 1.25 μM ddATP, 100 ng RNA, 15 ng primer and 2.8 units reverse transcriptase;

Tube C: same as tube A, except 20 μM dCTP, 2.5 μM ddCTP and no ddATP;

Tube G: same as tube A, except 20 μM dGTP, 3.0 μM ddGTP and no ddATP;

Tube T: same as tube A, except 20 μM dTTP, 7.5μM ddTTP and no ddATP;

Tube N: same as tube A, except no ddATP.

Each tube is incubated at 42° C. for 20 minutes. Following this incubation, 1 μl of chase solution (1 mM each of dATP, dCTP, dGTP and dTTP and 2 units of terminal deoxynucleotidyl transferase) is added to each tube and the tubes incubated for another 30 minutes at 37° C. The reactions are stopped by freezing at −20° C. Prior to electrophoresis, 5 μl of formamide dye mixture is added to each tube. The samples are then heated to 100° C. for 3 minutes and 5 μl of each sample is loaded per gel lane.

The sequencing gels (35 cm×13 cm×0.1 mm) are 6% polyacrylamide (38:2; acrylamide:bis-acrylamide) containing 7M urea in TBE (89 mM Tris, 89 mM boric acid, 2 mM EDTA).

When the complete sequence of the attenuated strain 3 poliovirus RNA genome is compared to the published P3/Sabin cDNA sequence [Stanway et al., *Proc. Natl. Acad. Sci. USA,* 81, pp. 1539–43 (1984)], two nucleotide differences are observed, one of which causes an amino acid change. These are shown in the following table:

| Nucleotide Position | P3/Sabin Stanway | P3/Sabin RNA | Amino Acid Change |
|---|---|---|---|
| 2493 | T | C | Ile to Thr (VPI) |
| 6061 | C | U(T) | silent |

The difference observed at position 2493 is important for several reasons. First, it encodes a significant amino acid change in the viral capsid protein VP1. Moreover, because wild-type strain 3 poliovirus has a U at this position (T in the cDNA), the purported presence of a T at 2493 of the attenuated strain 3 poliovirus cDNA may have obscured a significant difference between the wild-type and attenuated genomes.

EXAMPLE 3

Synthesis Of A Full-Length Poliovirus cDNA

The viral RNA obtained in the previous Example is used as a template for the synthesis of a double-stranded cDNA using the method of V. R. Racaniello et al., "Molecular Cloning Of Poliovirus cDNA And Determination Of The Complete Nucleotide Sequence Of The Viral Genome", *Proc. Natl. Acad. Sci. USA,* 78, pp. 4887–91 (1981). Specifically, 2.5 $\mu$g of viral RNA is used to produce first strand cDNA in a 100 $\mu$l reaction containing 50 mM Tris-HCl, pH 8.3, 10 mM $MgCl_2$, 50 mM KCl, 0.5 mM each of dATP, dTTP, dGTP and dCTP, 0.4 mM DTE, 30 $\mu$g/ml olio dT (12–18 nucleotides in length), 4 mM sodium pyrophosphate, 10 $\mu$Ci/$\mu$l [α-$^{32}$P]-dATP, 1 unit/$\mu$l RNasin and 2 units/$\mu$l reverse transcriptase [Boehringer-Mannheim, Indianapolis, Ind.]. The reaction is incubated at 42° C. for 60 minutes. The reaction is stopped by the addition of EDTA to a final concentration of 50 $\mu$M. The solution is then phenol extracted and the aqueous layer applied to a 5×0.7 cm Sepharose CL-4B column. The column is developed with 0.3M NaCl, 10 mM Tris-HCl, pH 8.0, 1mM EDTA. The profile thus obtained is depicted in FIG. 1.

Fractions 5–13 are pooled from the column and 20 $\mu$g of glycogen is added thereto. The cDNA is then precipitated at −20° C. by the addition of 2.5 volumes of ethanol, pelleted by centrifugation and resuspended in 25 $\mu$l of 10 mM Tris-HCl, pH 8.0, 1 mM EDTA (TE) for use in second strand synthesis.

Second strand synthesis is performed in a 100 $\mu$l reaction containing the single-stranded cDNA, 20 mM Tris-HCl, pH 7.4, 7 mM $MgCl_2$, 0.1M KCl, 50 $\mu$g/ml bovine serum albumin (BSA), 0.1 mM of each dNTP, 150 $\mu$M β-NAD, 5 $\mu$g/ml *E. coli* DNA ligase, 250 units/ml *E. coli* DNA polymerase I and 90 units/ml RNase H. The mixture is incubated at 15° C. for 60 minutes followed by 90 minutes at room temperature. The cDNA is then phenol extracted and chromatographed over Sepharose CL-4B as described above. The void volume fractions are pooled, precipitated with ethanol and resuspended in 25 $\mu$l TE, as described previously.

The resulting double-stranded cDNA is tailed with deoxycytidine (dC) in a 100 $\mu$l reaction containing 140 mM K-cacodylate, pH 7.2, 30 mM Tris-HCl, 1 mM $CoCl_2$, 1 mM DTT, 50 $\mu$g/ml BSA, 150 $\mu$M dCTP and 800 units/ml terminal deoxynucleotidyl transferase. The reaction is incubated at 37° C. for 60 minutes and the solution is then phenol extracted. The aqueous layer is removed, ether extracted and the tailed cDNA is precipitated therefrom with ethanol containing 20 $\mu$g glycogen. The resulting pellet is suspended in 50 $\mu$l of 10 mM Tris-HCl, pH 7.5, 100 mM NaCl, 1 mM EDTA (NTE).

EXAMPLE 4

Production Of A Poliovirus cDNA Library

Increasing amounts (1, 2, 5, 10 $\mu$l) of dc-tailed, double-stranded cDNA, produced as in Example 3, are annealed to 10 ng of PstI-cleaved, dG-tailed pUC9 (Pharmacia, Piscataway, N.J.) in NTE by heating the mixture to 68° C. in a water bath for 5 minutes, cooling the mixture in a 42° C. water bath and then slowly decreasing the temperature to room temperature overnight by shutting off the water bath. This allows for optimal hybridization between the dC tails on the cDNA and the dG tails on pUC9. The annealed mixtures are then used to transform *E. coli* DH5α cells (Bethesda Research Labs, Gaithersburg, Md.) using standard procedures. Ampicillin-resistant colonies are selected for screening.

EXAMPLE 5
Isolation Of Poliovirus Clones

Bacterial colonies are picked onto gridded plates and screened by colony hybridization, using linearized plasmid pOLIO (Sabin) as a probe [J. W. Almond et al., "Attenuation and Reversion to Neurovirulence of the Sabin Poliovirus Type-3 Vaccine", In *Vaccines*, 85, Cold Spring Harbor Laboratory, Cold Spring Harbor, N.Y., pp. 271–77 (1985)]. Plasmid pOLIO (Sabin) is a plasmid containing a full-length cDNA derived from P3/Leon 12a$_1$b [G. Stanway et al., *Proc. Natl. Acad. Sci. USA*, 81, pp. 1539–43 (1984)]. Of the 600 colonies screened by hybridization, 140 give positive hybridization signals. Small cultures (5 ml; LB media+ ampicillin) of each of these positive clones are prepared and the plasmid DNA is isolated by the rapid boiling method [T. Maniatis et al., *Molecular Cloning: A Laboratory Manual*, Cold Spring Harbor Laboratory (1982)]. The isolated plasmids are cleaved with PstI, which is predicted to excise the cloned insert. Of the 140 clones which are analyzed in this way, the vast majority contain either small inserts (<1 kb) or do not release inserts upon cleavage with Pst1. We are, however, able to identify and map three cDNA clones to the P3/Sabin genome (pLL3-51, 69 and 82; see FIG. 2). Eight hundred colonies are screened by colony hybridization using anEcoRI fragment of pOLIO(Sabin) cDNA, which contains the 5'-most 747 nucleotides, as a probe. Of the thirty-three colonies that hybridize to the probe, five of the cDNAs represent nucleotides 85–779 of P2/Sabin. The origin of these cDNA clones is not known.

Subsequently, additional cDNA is annealed to pUC9 and transformed into DH5α cells. Eight hundred colonies are screened by colony hybridization using full-length pOLIO (Sabin) cDNA as a probe. Twenty-nine positive clones are analyzed by restriction enzyme cleavage. Eight of the positive clones that contain cDNA inserts are subjected to nucleotide sequencing from either end of the inserted DNA. Five of these clones (pLL3-239, 251, 253, 254 and 255) contains a cDNA that maps to the 3'-end of the P3/Sabin genome (FIG. 2).

Figure 1:
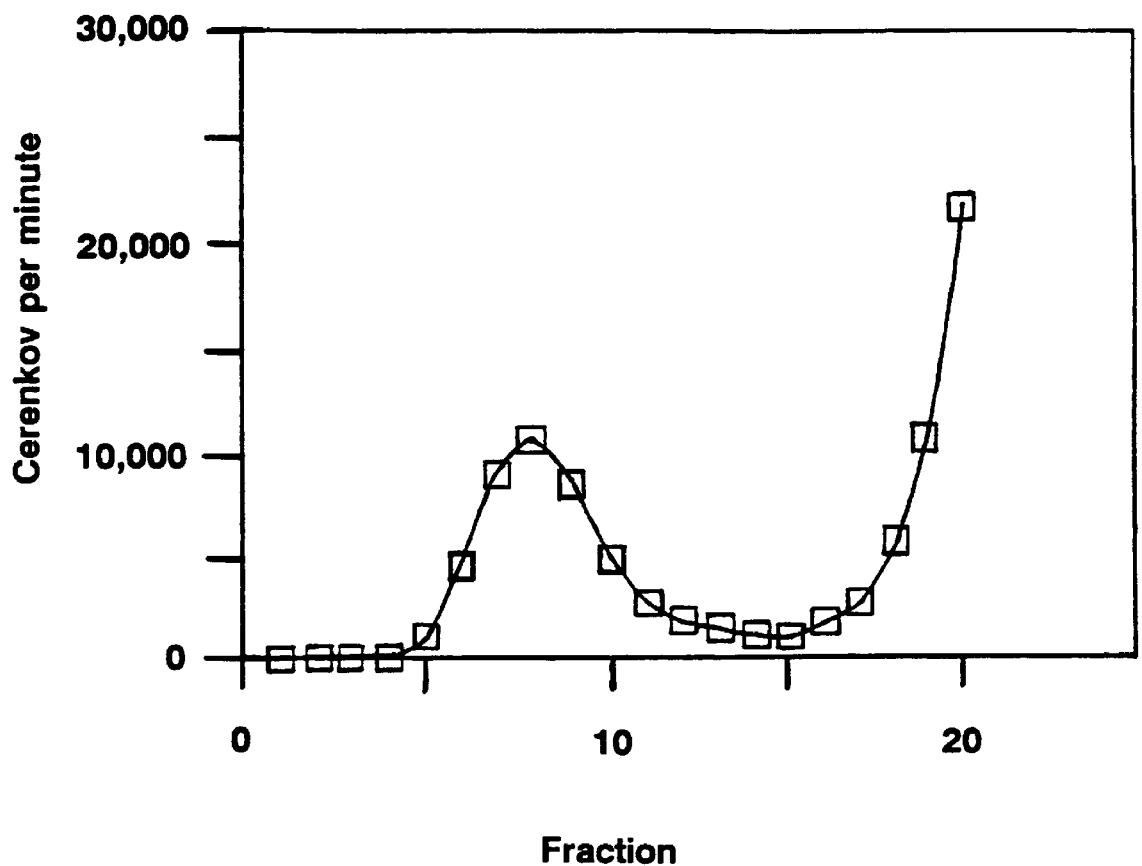
FIG. 1 depicts a chromatographic profile of first-strand cDNA synthesized from poliovirus strain 3 RNA off a Sepharose CL-4B column.
Figure 2:
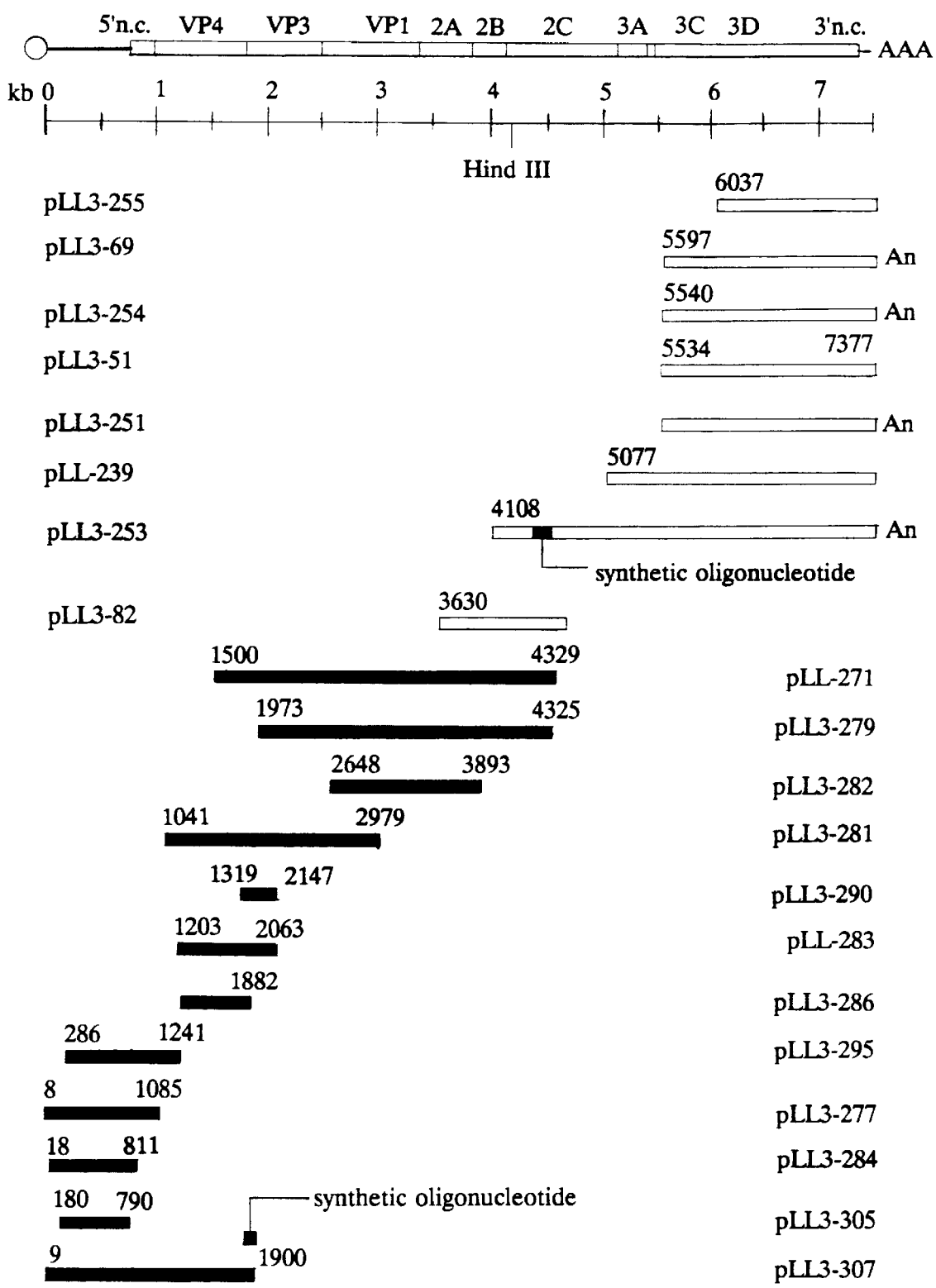
FIG. 2 depicts the cDNA clones which mapped to the P3/Sabin genome.

As depicted in FIG. 2 (open bars), the 8 isolated and analyzed cDNA clones represent nucleotidase 3630 through the 3'-end of the P3/Sabin viral RNA genome.

To obtain additional 5'-cDNA clones, an oligonucleotide complementary to a stretch of bases from nucleotide 4317–4334 (see black shading in FIG. 2, pLL3-253) is synthesized. This oligonucleotide is used to prime cDNA synthesis on P3/Sabin viral RNA isolated according to Example 2 using cDNA synthesis methods described in Example 3. The resulting cDNAs are dc-tailed and cloned into PstI-cut, dG-tailed pUC9. The resulting plasmids are then used to transform DH5α cells. Transformants are screened by hybridization to pOLIO (Sabin 3). Eleven positive cDNA clones are isolated, analyzed by restriction enzyme digestion and sequenced (FIG. 2, black boxes). The eleven clones correspond to nucleotides 6 through 4329 of the P3/Sabin viral RNA.

Although cDNA clones representing all but the first 5 nucleotides of the P3/Sabin genome are identified, attempts to ligate together several of the 5'-cDNAs into a single cDNA proved difficult, due to the lack of convenient restriction sites. Therefore, one final round of cDNA cloning is undertaken in an attempt to obtain a single cDNA clone that represented approximately nucleotides 1 through 1900.

An oligonucleotide complementary to bases 1904–1922 is synthesized and used to prime cDNA synthesis on P3/Sabin RNA. The cDNA is then dc-tailed, inserted into dG-tailed, PstI-cut pUC9 and the resulting plasmid is used to transform DH5α cells. The transformants are again screened with pOLIO (Sabin 3). One of the resulting cDNA clones is identified as containing nucleotides 9–1900 of the viral RNA (FIG. 2, pLL3-307). This completes the cDNA cloning of the P3/Sabin genome.

EXAMPLE 6
Construction Of A Full-Length Poliovirus cDNA

The strategy for assembling the P3/Sabin cDNAs into a single full length cDNA is depicted in FIG. 3. First, clones pLL3-253 and pLL3-271 are assembled into a single clone by using a common HindIII site at nucleotide 4241. The resulting cDNA clone, which represents nucleotides 1500 through the 3' poly(A) of the genome, is called pLL3-I.

Next, the first 5 nucleotides of the P3/Sabin viral genome, which are missing from cDNA pLL3-277, are synthesized. This is achieved by synthesizing two complementary oligonucleotides using an automated oligonucleotide synthesizer and then annealing the oligonucleotides to one another. The resulting double-stranded oligonucleotide comprising from 5' to 3', a PstI site, nucleotides 1 through 34 of P3/Sabin cDNA and a BgeI sticky end, is then used to replace the 5'-most PstI/BglI fragment of pLL3-277. This results in a cDNA clone that represents nucleotides 1–1085. This clone is called pLL3-II.

The final step is the ligation of three SacI fragments representing nucleotides 1–747, 747–1895 and 1895 through the 3'-end, to form a full length P3/Sabin cDNA (termed pLL3-FL). This construction is performed in several separate steps using appropriate cDNA inserts from pLL3-II, pLL3-307 and pLL3-I.

EXAMPLE 7
Sequence Analysis Of The P3/Sabin cDNA

Sequence analysis of P3/Sabin cDNAs used to construct the full length cDNA is performed using three approaches. In the first approach, cDNAs are subcloned into M13 vectors. Nested deletions of the subcloned cDNA, using exonuclease III and mung bean nuclease [E. Ozkaynak et al., "A Unidirectional Deletion Technique for the Generation of Clones for Sequencing, *Biotechniques*, 5, pp. 770–73 (1987)], are then isolated and their nucleotide sequences determined.

In the second approach, cDNAs are isolated and digested with the RsaI. The resulting fragments are then "shotgunned" into M13 for sequence analysis. The last approach utilizes cDNA fragments that are isolated from clones and subcloned into M13 for sequence analysis.

Upon nucleotide sequencing of the entire P3/Sabin cDNA clone, 3 differences are found when the cDNA sequence is compared to the RNA sequence. These differences are summarized in the following table:

| Nucleotide Position | P3/Sabin cDNA | P3/Sabin RNA | Amino Acid Change |
|---|---|---|---|
| 198 | G | A | 5' untranslated |
| 4466 | T | C | His to Tyr (2C) |
| 6334 | T | C | silent |

The nucleotide error at position 198 in the cDNA is situated in the 5' untranslated region of the genome. The function of that region remains unknown. The presence of a T, not a C, in the cDNA at position 4466 would create a change in residue 118 of the 2C protein from histidine to tyrosine. Although the function of the 2C protein remains undefined, the predicted amino acid change appears to be significant. The nucleotide change at position 6334 is in the polymerase gene, but is silent with respect to amino acid change.

Figure 4A:
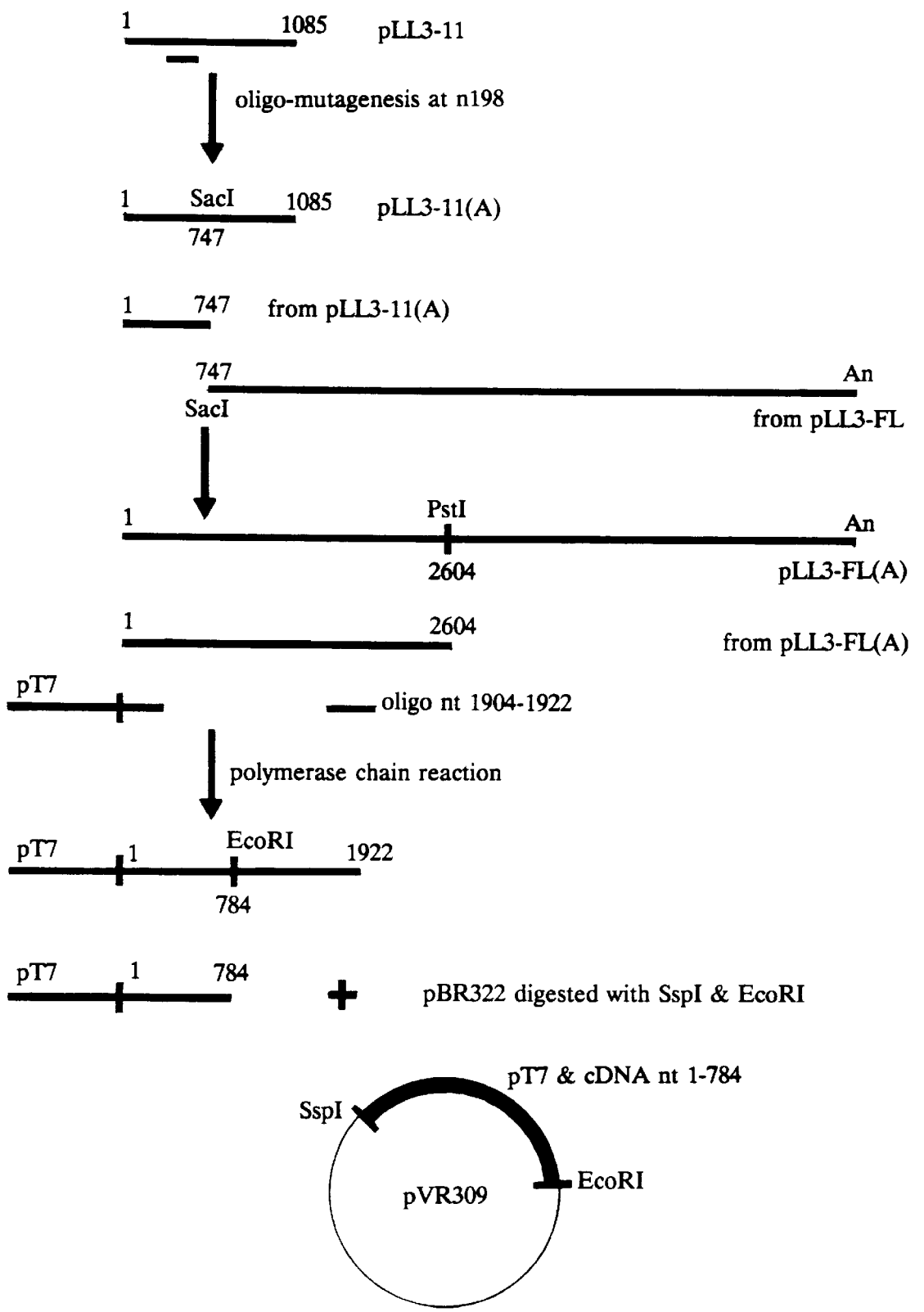
FIGS. 4A and 4B depict the strategy for mutagenizing P3/Sabin cDNA and constructing a true, full-length P3/Sabin cDNA according to this invention. Depiction of the strategy continues in FIG. 5.
Figure 4B:
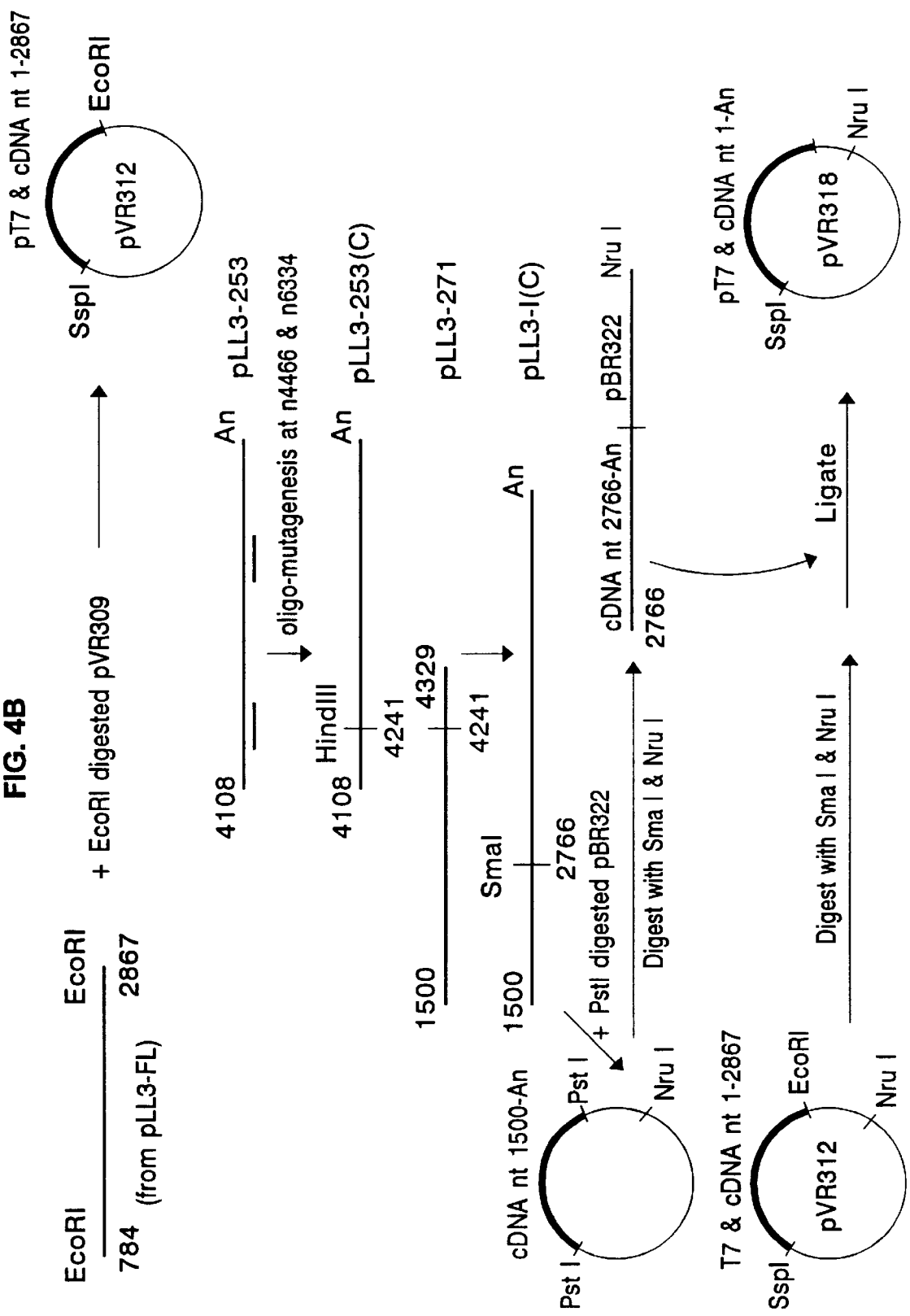
Figure 4C:
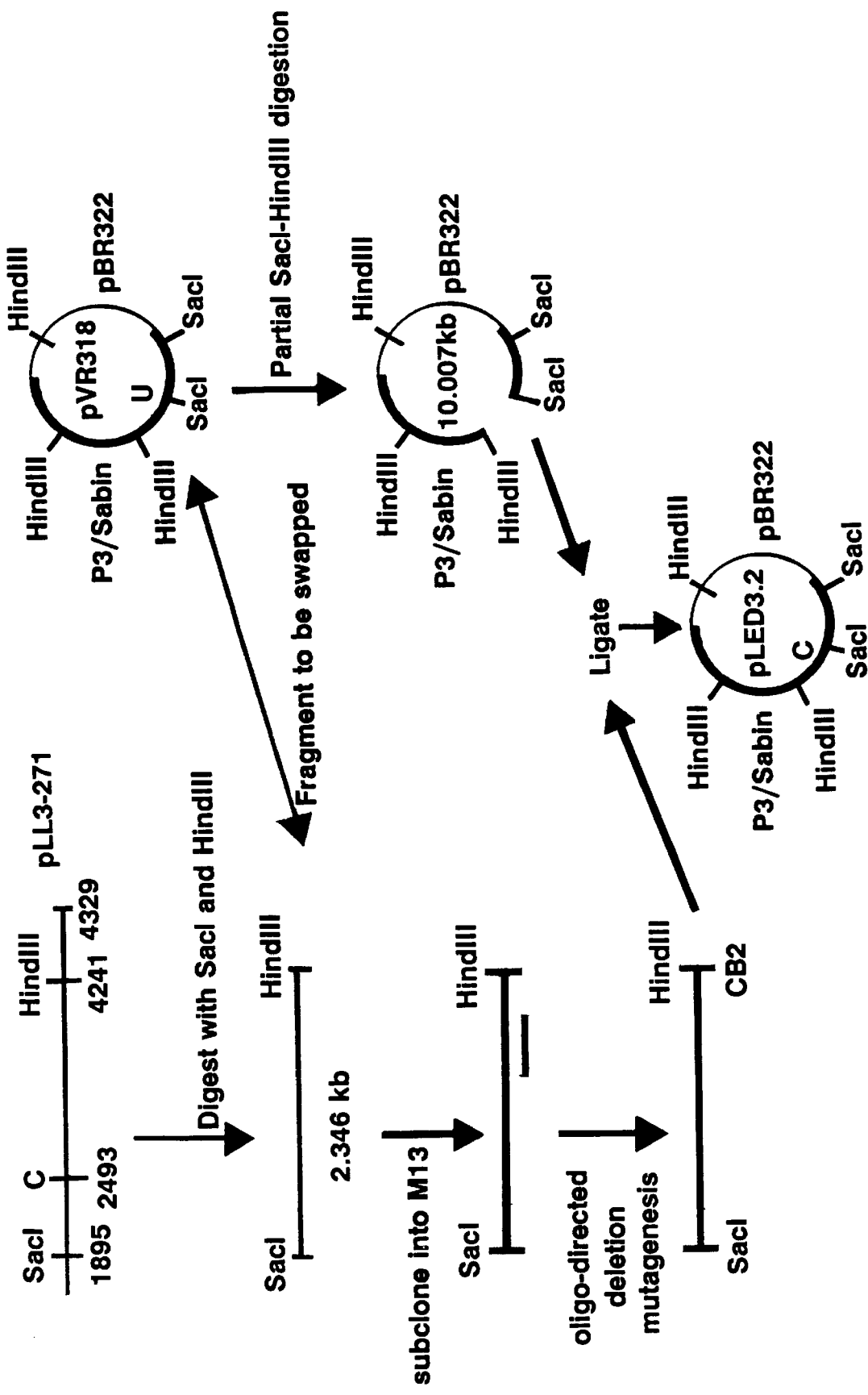
FIG. 4C depicts the following. The sequence of pLED3 depicted in FIGS. 6A–6J (SEQ ID NO. 1–2) was deduced from the complete analysis of pVR318 which was then altered at position 2493 by exchanging a SacI/HindIII fragment from the same subclone (pLL3-271) used to construct pVR318. However, confirmatory sequencing of the entire cDNA sequence in plasmid pLED3 revealed an additional "A" (adenosine) in a region where a run of six A's is normally found in the viral genome (position 4133–4138). The erroneous "A" was also found in subclone pLL3-271. The pLL3-271 and pBr318 were manipulated to make pLED3.2 which contains the correct number of A's at this site.
Figure 5:
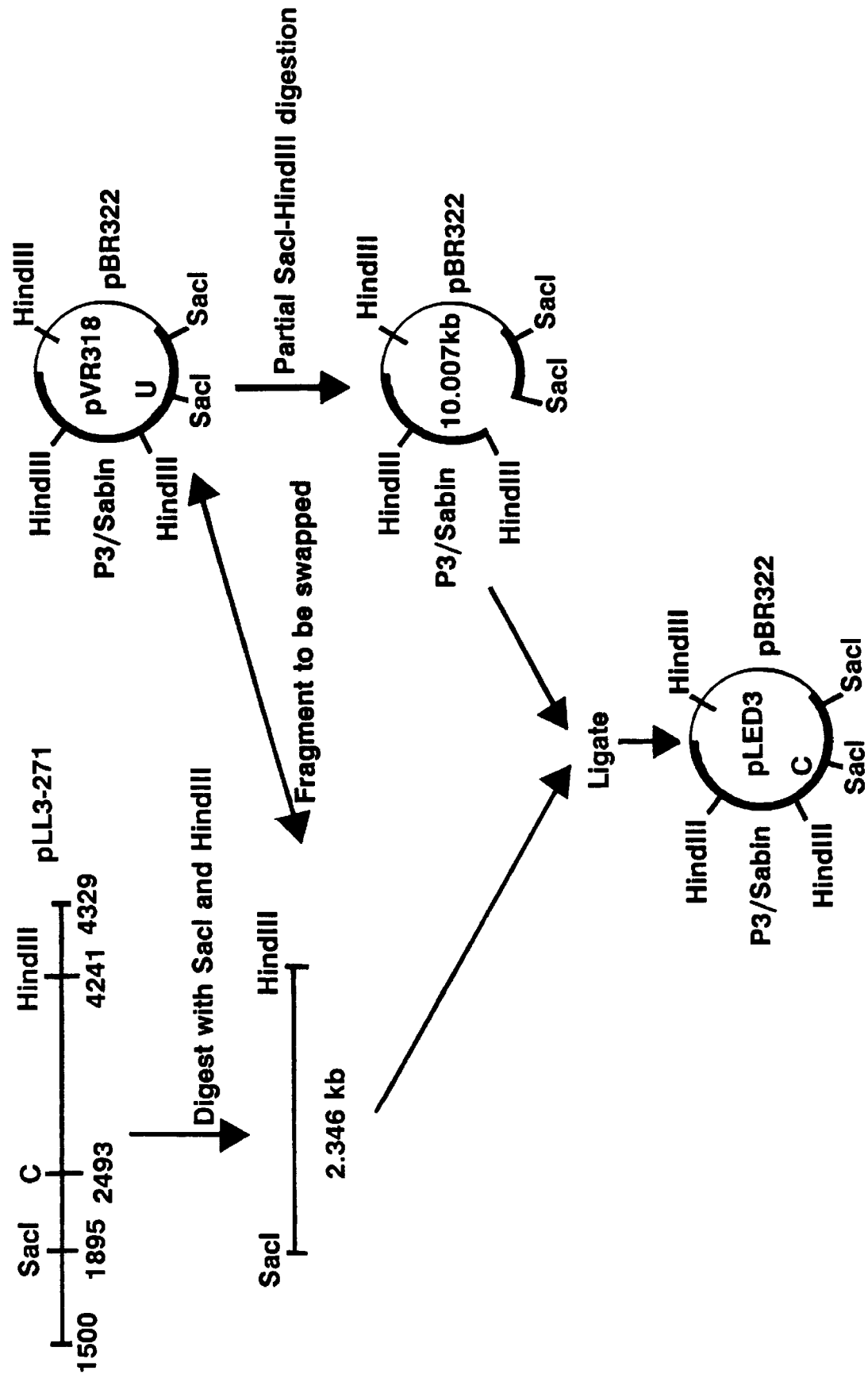

In order to obtain a full-length cDNA clone which corresponds exactly to the poliovirus RNA sequence, the protocol depicted in FIG. 4, panels A and B is followed. Specifically, the P3/Sabin cDNA insert pLL3-II is subcloned into the PstI site of bacteriophage M13 for oligonucleotide-directed mutagenesis of nucleotide 198 from G to A as described below. An oligonucleotide spanning nucleotides 190–206 and containing an A at position 198 is synthesized for this purpose. The oligonucleotide has the sequence: 3'-GGCGTATCTGACAAGGG-5'.

Mutagenesis is performed using a "T7-GEN In Vitro Mutagenesis Kit" (United States Biochemical, Cleveland, Ohio) and following the manufacturer's directions. The mutagenized insert is called pLL3-II(A). Following mutagenesis, pLL3-II(A) is sequenced to confirm the presence of an A at position 198. pLL3-II(A) is then removed from M13 with PstI and subsequently digested with SacI, which cuts at nucleotide 747. The fragment spanning nucleotides 1–747 is used to replace the corresponding fragment in pLL3-FL. The resulting full-length cDNA containing the mutagenized nucleotide at position 198 is referred to as pLL3-FL(A).

Next, pLL3-FL(A) is digested with PstI and the fragment spanning nucleotide 1 to 2604 is isolated. A portion of the isolated PstI fragment of pLL3-FL(A)—nucleotides 1 to 1922—is then subjected to polymerase chain reaction (PCR) using the following two oligonucleotides as primers:

1) 5'-CTGCAGTAATACGACTCACTATAGGTTA-AAACAGCTCTGGGGTTG-3'; and
2) 5'-GAATCATGGTGTCTATCTC-3'.

Oligonucleotide 1 represents, in a 5'-to-3' orientation, a PstI site, the T7 promoter and nucleotides 1–20 of the positive strand of P3/Sabin cDNA. Oligonucleotide 2 represents nucleotides 1904–1922 of the negative strand of P3/Sabin cDNA. PCR is performed using the GeneAMp kit from Perkin-Elmer Cetus.

The double-stranded DNA produced by PCR is then cleaved with EcoRI, which cuts at nucleotide 784 of P3/Sabin cDNA. The resulting 0.8 kb fragment representing the T7 promoter and the 5' end of P3/Sabin cDNA is isolated and subcloned into the SspI/EcoRI-cut pBR322. The resulting plasmid, termed pVR309, is confirmed to contain the T7 promoter and nucleotides 1–784 of P3/Sabin cDNA.

Next, pLL3-FL is cut with EcoRI, which cuts at nucleotides 784 and 2867. The fragment spanning these nucleotides is isolated and ligated to EcoRI cut PVR309. The resulting plasmid, pVR312, contains the first 2867 nucleotides of P3/Sabin cDNA.

In order to change the nucleotides at 4466 and 6334 to correspond to the viral RNA sequence, oligonucleotide-directed mutagenesis is performed as described above. The insert pLL3-253 is subcloned into the PstI site of M13. Oligonucleotide 3'-CTCGTTTGTGGCATAAC-5' is used to change nucleotide 4466 from a T to a C. Oligonucleotide 3'-CCCATGGGGATGCACCG-5' is used to change nucleotide 6334 from a T to a C. The mutagenized nucleotides are confirmed by nucleotide sequencing. The resulting corrected cDNA fragment termed pLL3-253(C).

Next, pLL3-253(C) and pLL3-271 are assembled into a single clone by cleaving each with HindIII and subsequently ligating the resulting large fragments together. The resulting DNA, referred to as pLL3-I(C), represents nucleotides 1500 through the 3-poly(A) end of P3/Sabin. The complete cDNA insert of pLL3-I(C) is then isolated by partial PstI digestion. A partial digest is necessitated because of the presence of a PstI site at nucleotide 2604. pLL3-I(C) is then ligated to PstI cut pBR322. A portion of that insert is then removed from pBR322 by a SmaI/NruI digest. The excised piece spans nucleotide 2766 through the 3'-end of the cDNA and into pBR322. A SmaI/ NruI fragment is also excised from pVR312. This DNA represents sequences from the NruI site in pBR322 through the T7 promoter and the 5'-end of P3/Sabin cDNA and up to the SmaI site at nucleotide 2766. These two SmaI/NruI fragments are then ligated together to form a true P3/Sabin cDNA. The resulting plasmid is called pVR318. The presence of a full-length insert in pVR318 is confirmed by restriction enzyme analysis. However, upon sequencing of pVR318 it was determined that position 2493 was found to have a T, rather than a C.

In order to convert nucleotide 2493 to a C, a SacI/HindIII restriction fragment spanning nucleotides 1895 through 4241 from PVR318 is removed and replaced with a corresponding fragment from subclone pLL3-271. This scheme is depicted in FIG. 5. Specifically, pLL3-271 is digested with SacI and Hind III and the 2.346 kb fragment spanning nucleotides 1895 through 4241 is isolated by agarose gel electrophoresis. Plasmid PVR318 is partially digested with SacI and HindIII to remove the 2.346 kb fragment between nucleotides 1895 and 4241. The remaining 10.007 kb fragment is isolated by agarose gel electrophoresis and then ligated to the SacI/HindIII fragment from pLL3-271. The resulting ligation product, pLED3, represents a true full-length type 3 poliovirus vaccine strain cDNA. The sequence of pLED3 is depicted in FIG. 6, panels A–J.

EXAMPLE 8

Transfection Of Cells With Poliovirus P3/Sabin cDNA

Primary monkey kidney cells are grown to 80% confluency in duplicate 25 $cm^2$ flasks in Eagle's basal medium (BME) containing Hank's balanced salt solution, 0.35% bicarbonate and 10% calf serum. The cultures are maintained at 37° C. The medium is then removed and the cells transfected with pLED3 (prepared as in Example 7), added as a calcium phosphate precipitate in HEPES-buffered saline. After 20 minutes at room temperature, the cells are covered with Earle's lacteal maintenance medium and incubated for 4 hours at 37° C. The medium is then removed and the cells are washed once with fresh, warm medium. Two milliliters of 15% glycerol in HEPES-buffered saline are then added to the cells and incubation is continued for 3.5 minutes at 37° C. The glycerol is then removed and the cells are washed once again with fresh medium. One of the duplicate cultures is then covered with warm medium containing 1% Noble agar (Difco, Detroit, Mich.), while the other is covered with agar-free medium. The cultures are incubated at 34° C. for 1–5 days. Plaques are visualized by staining cells with 0.01% neutral red. Medium from the liquid culture is assayed for infectious poliovirus by plaque titration on Vero cells.

EXAMPLE 9

In Vitro Transcription Of P3/Sabin cDNA

In vitro transcription is performed by the method of van der Werf et al., *Proc. Natl. Acad. Sci. USA,* 83, pp. 2330–34 (1986). pLED3, containing the T7 promoter-P3/Sabin construct, is linearized at an appropriate restriction site outside of the poliovirus sequences and purified by phenol extraction and ethanol precipitation. This template DNA is then added to a mixture containing 20 mM sodium phosphate, pH 7.7, 8 mM $MgCl_2$, 10 mM DTT, 1 mM spermidine-HCl, 50 mM NaCl and 1 mM each of dATP, dCTP, dGTP and dUTP. RNA synthesis is initiated by the addition of 10–15 units of T7 RNA polymerase/µg linearized template and allowed to continue for 30 minutes at 37° C.

Following RNA synthesis, the DNA template is digested away with Dnase I. The remaining RNA is purified by phenol extraction and ethanol precipitation in the presence of 2.5 M ammonium acetate. The purified RNA is quantified by UV spectrophotometry.

EXAMPLE 10

Transfection Of Cells With In Vitro Transcribed P3/Sabin RNA

Semi-confluent monolayers of primary monkey kidney cell are prepared as described in Example 8. The cells are transfected with the RNA prepared in Example 9 using the method of A. Vaheri et al., "Infectious Poliovirus RNA: A Sensitive Method of Assay", *Virology*, 27, pp. 434–36 (1965). Specifically, the cell monolayers are washed with isotonic phosphate-buffered saline (PBS). After 15 minutes, the PBS is completely removed by aspiration. The monolayer is then coated with 0.25 ml of inoculum containing RNA and 500 µg/ml DEAE-dextran (Sigma, St. Louis, Mo.; 500,000 MW) in PBS. The infected monolayers are kept undisturbed at room temperature for 15 minutes, washed once with Earle's lacteal maintenance medium and then overlaid with either fresh medium or medium containing 1% agar, as described in Example 8. After 4–5 days at 34° C., virus is detected by plaque formation (in cultures containing agar) or by cytopathic effect.

Virus is then isolated and purified. Viral RNA is isolated by the techniques described previously. The isolated RNA is sequenced and the nucleotide at position 2493 is confirmed as cytosine, the same as the original source virus.

EXAMPLE 11

Evaluation Of The Effect Of Nucleotide 2493 On The Attenuation Of A Strain 3 Poliovirus A derivative of an attenuated strain 3 poliovirus cDNA which contains a T instead of a C at nucleotide 2493 is constructed, such as pVR318. Viruses are produced from cDNAs with either T or C at 2493 as in Examples 8 and 10. The resulting viruses are then tested for neurovirulence in monkeys according to standard protocols.

EXAMPLE 12

Increasing The Attenuation Of A Strain 3 Poliovirus

A strain 3 poliovirus cDNA which contains a T at position 2493 is subjected to site-directed mutagenesis to convert the T to a C. For example, pLED3 is digested with PstI to remove the poliovirus coding sequence. The poliovirus cDNA contains a single, internal PstI site at nucleotide 2604. Therefore, a PstI digestion yields a 5', 2.6 kilobase viral cDNA fragment and a 3', 4.8 kb viral cDNA fragment. The 2.6 kb fragment is isolated by standard techniques and subcloned into the unique PstI site of vector M13mp18. Nucleotide 2493 is then converted from a T to a C by site-directed mutagenesis using a "T7-GEN In Vitro Mutagenesis Kit" (United States Biochemical, Cleveland, Ohio) and following the manufacturer's directions. Following mutagenesis, the 2.6 kb piece of cDNA is removed from the vector, relegated to the 3' piece of viral cDNA and the intact cDNA is cloned into pBR322. Both the mutagenized cDNA and the original cDNA are used to produce viable poliovirus as in Example 8. The resulting viruses are assayed for attenuation according to standard protocols. The mutagenized virus produced by the cDNA containing a C at nucleotide 2493 is expected to be more attenuated than the original virus.

Confirmatory sequencing of the entire cDNA sequence in plasmid pLED3 revealed an additional A (adenosine) in a region where a run of six A's is normally found in the viral genome (positions 4133–4138). The following steps describe a method to derive pLED3.2 from pLED3:

Isolation and mutagenesis of erroneous pLED3 sequence

Starting with purified pLED3 plasmid DNA, digest the DNA to completion with restriction enzymes SacI and HindIII. By a method of choice (i.e., gel electrophoresis, HPLC) purify the 2,346 base pair SacI/HindIII fragment representing cDNA nucleotides 1895–4241.

Subclone the purified restriction fragment into bacteriophage M13 to enable oligo-directed deletion mutagenesis. An DNA oligonucleotide spanning nucleotides 4121–4150 is synthesized for this purpose. The sequence of this oligomer is: 5'-CGCCTCAGTAAATTTTTTCAACCAACTATC-3'.

Mutagenesis is performed using a "T7-GEN In Vitro Mutagenesis Kit" (United States Biochemical, Cleveland, Ohio) and following the manufacture's directions. The mutagenized insert is confirmed to possess 6 instead of 7 A's at positions 4133–4138 by sequence analysis. As above, the altered SacI/HindIII fragment is gel purified in preparation for ligation into the plasmid body lacking this restriction fragment.

Preparation of pLED3.2 from pLED3 plasmid

Starting with purified pLED3 plasmid DNA, partially digest the DNA with restriction enzymes SacI and HindIII. Purify the 10,007 base pair SacI/HindIII fragment corresponding the plasmid minus the 2,346 base pair SacI/HindIII fragment discussed above.

Construction of pLED3.2:

The purified plasmid body and mutagenized 2,346 base pair fragment are ligated together. Competent *E. coli* DH5α cells are transformed with the ligation products and tetracycline resistant colonies are selected. Identity of pLED3.2 is based on the confirmation of 6 A's at 4133–4138.

LED3 and VR318 viruses used in monkey NV test

The full-length cDNA in pLED3 (uncorrected) was infectious even though the additional A discussed above predicts a shift in the reading frame for viral proteins 2C, 3A, 3B, 3C and 3D. In vitro transcription of pLED3 cDNA using T7 RNA polymerase produced RNAs which possessed the erroneous seven A's as determined by direct sequence analysis. When these transcripts were used to transfect monkey kidney cells, virus was recovered which possessed the correct number of A's at this site.

Although the cDNAs in pLED3 and pVR318 differ by nucleotide composition at 2493 and by the number of A's between 4130–4136, the 2493 mutation was the only difference found to distinguish the viruses generated using these cDNAs. These cDNA-derived viruses were used to carry out the studies to assess the significance of 2493 mutation (described in the manuscript currently under review).

Polymerases are known to have problems copying from regions in which a single nucleotide is repeated several times. We proposed that T7 RNA polymerase may have generated by error some RNAs which contained six instead of seven A's while transcribing the run of seven A's from pLED3. Only those transcripts possessing six A's could produce virus upon transfection of cells. This proposed explanation seemed highly probable to a scientist who works on T-phage polymerase.

Recombinant DNA prepared by the processes of this invention is exemplified by a sample deposited with the American Type Culture Collection located at 12301 Parklawn Drive, Rockville Md. 20852 under the provisions of the Budapest Treaty on the International Recognition of the Deposit of Microorganisms for the Purposes of Patent Procedures. This sample was deposited on Apr. 17, 1990, identified as a plasmid containing the infectious full length copy of vaccine strain Sabin 3, and designated pLED3. This deposit was assigned ATCC accession number 40789.

EXAMPLE 13

Experimental Methods
Sabin 3-Specific Mutation Within the N-Terminal Region of VP1 is Attenuating
Preparation of cDNA clones Viral RNA was extracted from Sabin 3 vaccine virus (Lederle-Praxis Biologicals, N.Y.) after pelleting and SDS disruption as described before (20). A cDNA library was made from the viral RNA template using reverse transcriptase and a procedure described elsewhere (12). Oligonucleotide-directed mutagenesis was performed on DNAs subcloned in M13 grown in E. coli CJ236, to change the cDNA sequence at single base positions (16). For this purpose, antisense oligonucleotides (17-mers) were synthesized with the target nucleotide positioned in the center of the sequence. Common restriction enzyme cleavage sites EcoRI, HindIII, SacI, SmaI) were used to construct full-length cDNA clones. The full-length cDNAs (7,459 bp) were constructed in vector pBR322, selected and amplified using E. coli DH5α (Bethesda Research Laboratories).
Cells Vero cells were propagated as monolayers in Eagle's MEM with Earle's salts supplemented with 0.11% bicarbonate and 10% fetal bovine serum. Primary African green monkey kidney cells (PCMK) were initiated in BME with Hank's salts containing 0.035% bicarbonate and 10% serum. At 70% confluence, the cells were refed with BME (Earle's salts) containing 5% serum. During poliovirus infection, all cultures were maintained in modified Earle's lactalbumin hydrolyzate maintenance medium (LMM; pH 7.34 without serum.
Viruses The Sabin 3 vaccine virus (RSO+2; Lederle-Praxis Biologicals, Pearl River, N.Y.) was prepared by a single passage of the rederived (RSO+1) manufacturing seed in PCMK cells. For experimental purposes, the same seed was used to produce RSO+2 vaccine virus in Vero cells. Virus NCl represents vaccine (SO+2) produced in PCMK cells from the original (SO+1) manufacturing seed. The cDNA-derived viruses recovered from Vero cells transfected with T7 RNA polymerase transcripts of pLED3 or pVR318 were designated LED3+1 and VR318+1. These "seed" viruses were amplified once more in Vero cells at a multiplicity of infection (MOI) of 0.1 at 33.5°±0.5° to create virus stocks LED3+2 and VR318+2. Particular attention was paid to preparing the LED3+2 and VR318+2 virus samples in a manner as similar as possible to actual vaccine (ie. passage level and culture conditions). The characterization studies were carried out using these final virus stocks.
Determination of Virus Titer The titer of infectious virus in samples was determined most often by microtitration on HEp-2 cells and expressed as tissue culture infectious dose $(TCID)_{50}$ per ml (1). In some cases, infectious titer was measured by plaque titration on Vero cell monolayers and therefore expressed as plaque-forming units (pfu) per ml. Serial ten-fold dilutions of virus prepared in LMM were used to inoculate 25 cm$^2$ confluent monolayers and allowed to absorb at 22° C. The cells were overlaid with 1.0% Noble agar (Difco Laboratories) in MEM (Hank's) plus 2% fetal calf serum then incubated at 33.5°±0.5° C. After 3 days, plaques were visualized and counted after staining the cells with neutral red (0.01% solution). For a given sample, there is routinely a 0.6 log difference in absolute numbers determined using the two methods described above; the $TCID_{50}$ value is always greater.
Nucleotide Sequence Determination RNA sequence was determined using synthetic oligonucleotides and the dideoxynucleotide chain termination method as described before (20). Sequencing of cloned cDNAs was performed using Sequenase DNA Sequencing Kit (U.S. Biochemical).
In Vitro RNA Synthesis and Transfection DNA templates were prepared by digesting the plasmid DNA completely with PvuI restriction enzyme followed by extraction with phenol and ethanol precipitation. Transcription reaction mixtures containing 1 μg of DNA template were prepared as described by Moss et al. (12). RNA synthesis was initiated by addition of 30 units purified T7 RNA polymerase (Pharmacia) and the reactions were incubated at 37° C. for 90 mins. The DNA template and full-length transcription product were quantitated by comparing the intensity of appropriately-sized bands to known amounts of a standard after electrophoresis in agarose gels stained with ethidium bromide. The 9.0 kb HindIII fragment of bacteriophage lambda DNA was used as the standard for template; a 7.5 kb single-stranded RNA marker (Bethesda Research Laboratories) was used for transcript. Numerical values were obtained by performing densitometry on a photographic negative taken of the gel. Aliquots of the transcription reaction mixture containing 25 μg of full-length transcript were used to transfect Vero cell monolayers (25 cm2) according to the procedure described by van der Werf et al. (23). The cDNA-derived viruses were harvested when the cell monolayer was completely destroyed (+4 CPE).
Isotopic Labeling of Virus and PAGE Vero cells ($6.5 \times 10^6$) were infected at an MOI of 16 pfu/cell. The virus was allowed to absorb for 1 hour, the cells were then washed twice and covered with LMM before incubation at 33.5° C. Four and a half hours later, the medium was changed to methionine-free MEM (Select Amine Kit, GIBCO). After one hour, the cells were replenished with fresh medium supplemented with [$^{35}$S] methionine (specific activity, >1000 Ci/mmol; Amersham) to a final concentration of 60 μCi/ml and incubation continued. At+4 CPE (within 24 hr), the medium containing virus was clarified, first by low-speed centrifugation (2500 rpm, 20 mins, 4° C.) and then by microfiltration (0.22 μm Millex-GV; Millipore). Virus was pelleted by ultracentrifugation using a Beckman 70.1Ti rotor (70K, 1 h, 4° C.), and then resuspended and boiled in Laemmli sample buffer (10). The samples were subjected to SDS-polyacrylamide gel electrophoresis and the proteins visualized by autoradiography.
Virus Thermostabiltiy Curves Multiple 3.0 ml samples of virus (approx. $10^{7.3}$ pfu/ml in LMM) were incubated at room temperature (22° C.) or in water baths at 37° C. or 42° C. At 24 hour intervals over the course of 5 days, one sample from each incubation set was removed and frozen at −20° C. Once all the sample incubations were completed, the virus titer in each sample was measured by plaque titration on Vero monolayers.
Virus Growth Curves Vero cell monolayers ($10^7$ cells/25 cm$^2$ flask) were infected with 4 pfu/cell and maintained as described above. At the indicated times post-infection, the medium from individual cultures was harvested then stored at 70° C.
Neurovirulence Test Virus samples were tested for neurovirulence in Macca mulatto monkeys using two accepted procedures. As described in the United States Code of Federal Regulations (22), 0.2 ml or 0.5 ml of virus sample containing at least $10^{7.6}$ TCID$_{50}$/ml is injected into the spinal cord (IS) or the thalamic region of each brain hemisphere (IT) of a monkey, for each test respectively. The WHO test (26) involves intraspinal injection of monkeys with 0.1 ml of virus (titer of $10^{6.5}$–$10^{7.5}$ TCID$_{50}$/ml). After injection, the test animals are observed for 17–21 days for clinical signs of poliomyelitis. The animals are then sacrificed to allow histological examination of the brain and spinal cord for poliovirus lesions. The nervous tissue from each monkey is evaluated using a scoring method from 1 (low) to 4 (high) to reflect the severity of neuronal damage observed. The mean lesion score is an average of the scores recorded for monkeys within a group.

Statistical Analysis

Differences in mean lesion scores were analyzed by Analysis of Variance (ANOVA) model with Least Squares determinations employed for mean range testing. Frequencies of reactivity in the monkeys injected intrathalamically were tested for significance using Chi-square test.

Results

Construction of an authentic LED3 cDNA

Screening of the cDNA library through restriction analysis and nucleotide sequencing, identified four cDNA clones which represented all but the 5' six nucleotides of the Sabin 3 genome. The 5'-most cDNA clone was modified so that first six nucleotides of Sabin 3 cDNA were reconstructed and positioned under the control of bacteriophage T7 promoter by incorporation of a synthetic DNA oligonucleotide [5'-CTGCAGTAATACGACTCACTATAGGTTAAAAC-AGCTCTGGGGTTTG-3'] using the polymerase chain reaction. The orientation of the promoter ensures the synthesis of positive-sense RNA transcripts of the cloned cDNA. When the complete nucleotide sequence of the four cDNA subclones was compared to the LED3 RNA sequence (24) four nucleotide differences were identified. It is unclear whether the nucleotide differences represent errors made during reverse transcription or sequence divergence of a minor population within the vaccine virus sample. However, the full-length uncorrected cDNA was not infectious since virus nor CPE resulted from transfection of cells with T7-derived transcripts made of the cDNA. The sequence was corrected using oligonucleotide-directed mutagenesis (see Materials and Methods, Example 13) at three of these positions: 198 (G to A), 4466 (T to C) and 6334 (T to C). The last error, U instead of C at position 2493, fortuitously represented the Leon-like nucleotide at this position and was left untouched in the full-length cDNA in pVR318. This clone differs from LED3 RNA sequence only at n2493. The final step in the production of an authentic LED3 cDNA (pLED3.2) was accomplished by cDNA fragment exchange (SacI at n1895 to HindIII at n4241) between pVR318 and a vaccine cDNA subclone found to possess C at position 2493.

The full-length LED3 cDNA construct in cloning vector pBR322 is diagrammed in FIG. 7, panel A. Nucleotide sequence analysis across the junction between the 3' terminus of the Sabin 3 cDNA and plasmid pBR322 indicated a poly-A tail consisting of 27 A's. A string of 15 C's derived from cDNA cloning steps immediately follows the poly-A tail.

In vitro transcription of the cDNAs in pLED3 and pVR318

The plasmid DNAs were digested with PvuI to 1) generate a linear DNA template containing the entire poliovirus cDNA for transcription by T7 RNA polymerase and to 2) create a template with the shortest span of extraneous vector sequence after the 3' end of the cDNA. PvuI corresponds to the first restriction site after the 3' end of the cDNA (exactly 126 bp) which is not present within the cDNA. Two PvuI fragments (4.4 kb and 8.1 kb) are produced from pLED3 and pVR318, but only the 8.1 kb fragment contains the T7 promoter based on sequence analysis. (refer to FIG. 7, A). Panel B of FIG. 7 demonstrates that RNAs are efficiently synthesized by T7 RNA polymerase from the PvuI-restricted pLED3 and pVR318 and their size matches that predicted for runoff transcripts from the 8.1 kb fragment. In lanes 5 and 6, the two upper bands (low intensity) correspond to the 8.1 kb and 4.4 fragments produced by digestion of the plasmid DNAs with PvuI. Lane 4 contains HindIII/lambda DNA for a ds DNA size reference. The transcription product (most intense band in lanes 5 & 6) comigrates neatly with the 7.5 kb ssRNA marker (lanes 1–3) which is consistent for full-length (7585 nucleotides) RNAs. In comparison to virion RNA (lane 7), the in vitro transcripts of the poliovirus cDNA migrate slightly faster, perhaps due to the absence of covalently attached VPg protein. A transcription reaction containing 1 µl of template reproducibly produced 20–25 µg of full-length transcript. As shown here, the band corresponding to in 1 µg of a 50 µl reaction mixture (lane 5 or 6) is approximately the same intensity as the band representing 500 ng of 7.5 kb ssRNA (lane 2). Direct sequence analysis of these transcripts determined that there are two extra guanines at the 5' end immediately before the first poliovirus nucleotide and confirmed the presence of 126 bp of extraneous pBR322 sequence at the 3' end after the poly-A, poly-C tail.

When Vero cells were transfected with the RNAs described above, cytopathic effects consistent with poliovirus infection were observed in 24 hours and virus were harvested (+4 CPE) within 48–72 hours. The specific infectivity of the transcripts was found to be $1-2 \times 10^2$ pfu/µg, about 3% that of vaccine RNA. As determined by sequencing, the RNA from the recovered viruses lacks the extraneous pBR322 sequence at the 3' end. In addition, the genomes of these viruses were verified to possess the attenuated nucleotides at positions 472(U), 2034(U), and 6061(U); nucleotide 2493 was the only known difference between LED3 (2493-C) and VR318 (2493-U).

Mutation at n2493 correlates with altered VP1 mobility

The mutation identified at position 2493 in the consensus genome of Sabin 3 vaccine virus predicts a Ile-6→Thr substitution in VP1 (24). To determine if the biochemical properties of VP1 would be altered by this amino acid substitution, the UPI proteins of LED3 altered by this amino acid substitution, the VP1 proteins of LED3 and VR318 were compared. The VP1 from LED3 contains threonine at residue 6, whereas VR318 has isoleucine at this site. The difference in molecular weights between these amino acids is minimal and yet the VP1 proteins from these viruses are distinguishable by SDS-PAGE (FIG. 8). A possible explanation for this observed difference in VP1 migration derives from the fact that the Thr side chain has a hydroxyl group that can form a hydrogen bond, whereas the Ile side chain is hydrophobic. As a result, the VP1 of VR318 virus with Ile-6 may bind more SDS and therefore migrate faster than the VP1 of LED3. These data associate at least one biophysical change with the 2493 mutation. Whether this alteration in VP1 impacts the 3D structure of the virion is under evaluation.

Thermostability of LED3 and VR318 viruses

In the three-dimensional structure of poliovirus, the N-terminal region of VP1 is buried on the inside of native virions in close association with terminal regions of the other capsid proteins (6). In attempt to assess whether the 2493 mutation alters virion stability, LED3 and VR318 viruses were compared for susceptibility to thermal inactivation at several temperatures. As illustrated in FIG. 9, there was no loss in titer observed for either virus sample over a five day period at room temperature (22° C.). At 37° and 42° C., the titers of both virus samples decreased similarly. Despite heat treatment, the difference in plaque morphology between LED3 and VR318 viruses were preserved (see below).

Effect of n2493 on phenotypic markers

Small plaque size is often used to differentiate attenuated vaccine strains from virulent strains (13). In conducting a simple plaque titration of the cDNA-derived virus samples on Vero cells monolayers, it became apparent that the VR318 virus produces plaques that are obviously larger than those of LED3 virus. When the comparison included the pathogenic parent Leon strain, it was clear that VR318 plaques are of intermediate size (see FIG. 10). These data suggest that the single nucleotide difference at position 2493 between LED3 (C) and VR318 (U) is responsible for the increase in plaque size displayed by VR318 compared to LED3.

The traditional temperature-sensitivity (rct/40° C.) and "d" marker phenotypes of LED3 and VR318 viruses were also evaluated. Although these viruses were not distinguishable by either of these tests, both exhibited the attenuated phenotype compared to Leon virus (data not shown).

Growth curves of LED3 and VR318

To compare LED3 and VR318 replication, the growth kinetics of these viruses were compared in Vero cells under conditions known to be permissive for attenuated poliovirus (i.e, low temperature, high pH). FIG. 11 demonstrates there is no dramatic difference between the kinetics of virus release from Vero cells infected with LED3 and VR318. The titers achieved at 24 hours post-infection ($10^8$ pfu/ml) indicated that neither of these viruses is severely debilitated under these conditions. A consistent, although subtle, difference was observed in the fold increase in titer between 8 and 12 hours post-infection suggesting that VR318 may have the ability to replicate faster than LED3. During this time period, the titer of VR318 increased 200-fold compared to only a 30-fold increase for LED3. Whether modification of culture conditions (i.e., lower pH) exaggerates the observed difference between LED3 and VR318 growth kinetics is under evaluation.

Neurovirulence of LED3 and VR318 in monkeys

Through the construction and neurovirulence testing of recombinant viruses derived from full-length Sabin 3 and Leon cDNAs, Westrop et a. (25) have correlated the attenuated phenotype of Sabin 3 with the point mutations at positions 472 and 2034. Applicants' identification of the Sabin 3-specific point mutation at 2493 (24), raised the question of whether this mutation might also be a determinant of attenuation.

The cDNA-derived viruses, LED3 and VR318, were compared to appropriate controls for neurovirulence as tested in monkeys by procedures contained in either the WHO or United States CFR requirements for the acceptance of vaccine lots (see Materials and Methods, Example 13). Differences between these procedures include the route of inoculation (intrathalamic & intraspinal versus only intraspinal) as well as amount (volume and titer) of the sample injected.

Table 1A lists the neurovirulence data from the CFR intraspinal (IS) test in which LED3 and VR318 were tested concurrently and compared to test results of actual vaccine (RSO+2) produced on primary monkey kidney cells (PCMK). Testing of RSO+2 (Vero) vaccine demonstrated that the use of Vero cells to produce vaccine virus as described had no effect on attenuation. The mean lesion scores produced by RSO+2 (PCMK), RSO+2 (Vero) and LED3+2 (Vero) were 0.52, 0.36 and 0.34, respectively. These data demonstrate that LED3 is no more neurovirulent than current vaccine virus. Interestingly, the mean lesion score of monkeys receiving VR318 was 1.31 which was significantly higher (p<0.01) than the scores produced by the other viruses. These data indicate that VR318 virus is not equivalent to current RSO+2 vaccine and that presence of C (LEd3 and RSO+2) instead of U (VR318) at nucleotide position 2493 is attenuating.

As above, the neurovirulence of LED3 and VR318 after intrathalamic route of injection into monkeys was compared to data obtained from four complete tests of current RSO+2 vaccine (Table 1B). Since brain tissue is less susceptible than spinal tissue to poliovirus infection, neurovirulence using this procedure is based essentially on whether any lesions are visible and in what percentage of the monkeys rather than a lesion score. As demonstrated by actual RSO+2 vaccine, a low level of reactivity in a group of monkeys (4.0%) is typical and desirable. Of the 10 monkeys receiving LED3, none exhibited lesions. VR318, however, produced lesions in 2 of 10 (20%) test animals. Although a group of 30 monkeys are required for a complete IT test, the increased percentage of positive monkeys in the VR318 group is highly unusual and predicts that VR318 would fail CFR IT data indicate that when compared to current RSO+2 vaccine, LED3 virus is equivalent and VR318 is more neurovirulent.

Using the WHO test procedure, LED3 and VR318 were evaluated concurrently with virus NCl, which is equivalent to the attenuated type 3 WHO test reference. As listed in Table 2, the mean lesion scores for LED3 and VR318 were 0.21 and 1.51, respectively. Confirmed by three different methods, the demonstration that LED3 is more attenuated than VR318 is unequivocal. The interpretation of the WHO test data is made somewhat difficult however by the performance of the attenuated reference, NCl. In this test, NCl produced a mean lesion score of 1.08, which falls between the values calculated for LED3 and VR318. Although a mean score of 1.08 is high for this test reference, the comparison of reactivity between NCl, LED3 and VR318 is valid since they were tested concurrently. A statistical comparison of the resultant scores points to the fact that by this test procedure, VR318 cannot be distinguished from the attenuated reference. Based on this preliminary data, it is unclear whether VR318 would fail in a full WHO test involving 24 monkeys per group. On the other hand, the lesion score associated with LED3 was shown to be significantly lower than either VR318 or the NCl reference (p<0.01).

Interestingly, the NCl reference virus represents vaccine material manufactured using Sabin original (SO), not the rederived Sabin original (RSO) seed. Nucleotide sequence determination at position 2493 of SO+2 vaccine (Lederle; same as NCl) revealed a 1:1 mixture of C and the variant U. Similar evaluation of current RSO+2 vaccine (Lederle) demonstrated only C at this position supporting the fact that the RSO seed is a purified derivative of the SO strain (24). Since test samples LED3, VR318 and NCl did not differ in nucleotide composition at position 472 based on RNA sequence determination, the increased level of neurovirulence exhibited by NCl compared to LED3 using the WHO procedure likely derives from the subpopulation of 2493-U variants in the NCl pool of virus.

The identification of a new Sabin 3-specific mutation at position 2493 which encodes an isoleucine to threonine change at the sixth amino acid of VP1 (24) is shown here to be a determinant of attenuation. The attenuation of Sabin 3 poliovirus has been correlated to point mutations at positions 472 and 2034 by others previously (25). To assess the contribution of the 2493 mutation, a virus was produced using a completely verified vaccine cDNA (LED3) and compared it to a derivative, VR318, which was the same except that it possessed the Leon-like nucleotide (U) instead of C at this position. The additional mutation in LED3 correlated to smaller plaque size as well as decreased neurovirulence in monkeys.

The data presented herein demonstrate that the biological properties associated with attenuation of the Sabin 3 vaccine strain were preserved in LED3. There are many benefits associated with the use of a Sabin 3 cDNA-derived seed strain. The stock volumes of both the original and rederived Sabin seeds, SO and RSO respectively, are limited due to the fact that they are virus plaque isolates. When seeds are stored in the form of a cloned, genetically defined cDNA, the limitations on seed supply are removed; in addition, such seeds can be preserved indefinitely. Without restriction on seed supply there is increased flexibility in the multiplicity of infection (MOI) that can be used to produce vaccine. Weeks-Levy et al. (24) showed that virus samples produced using accepted manufacturing seeds at higher MOI's are genetically more homogeneous. Since RNA viruses by their nature generate variants at height frequency than DNA viruses, an RNA virus seed established in the form of a cloned, genetically defined DNA should be the most homogeneous. By this approach, the amount of undesirable variants that could be selectively amplified during passage have been minimized which translates to increased genetic stability. Passage studies to assess whether LED3 constitutes a more genetically stable see as compared to other manufacturing seeds for Sabin 3 vaccine is currently under evaluation.

Based on nucleotide sequence determination, Sabin 3 variants possessing U at 2493 during passage in vitro were shown to accumulate more rapidly than variants possessing C at 472 (24). In the same study, the Sabin 3 component of different OPVs was found to vary greatly in the proportion of C and U at 2493. Although the data presented here do not address how the proportion of 2493-U variant affects the acceptability of vaccine lots, data comparing viruses LED3 (2493-C) and VR318 (2493-U) suggest that the result will depend on neurovirulence test method used for the evaluation. Of particular interest was the ability of the CFR intrathalamic test method to distinguish LED3 and VR318. The unusually high reactivity of VR318 in the brain compared to LED3 or RSO+2 vaccine suggests that the interaction between virus and brain tissue is enhanced when virus possesses U at 2493. Since the WhO test method does not evaluate vaccine by intrathalamic route of injection, our data suggest that this test would be less likely to detect 2493-U virus subpopulation in vaccine lots.

A detection method incorporating the polymerase chain reaction was used recently by Chumakov et al. (2) to determine that vaccine lots containing 472-C variants comprising greater than 1.17% of total virus failed the WHO neurovirulence test. The determination of equivalence at position 472 for LED3 and VR318 was based on sequence analysis of the viral RNA. It was determined that a 10% variant subpopulation is the limit of detection using this method (20). It is possible that the more sensitive PCR method would detect 472-C subpopulation in both LED3 and VR318 virus preparations. It is however unlikely that these virus samples would differ in proportion of 472-C variant because LED3 and VR318 are equivalent passage levels from the cloned cDNA and were generated under identical conditions. A preliminary evaluation of LED3 and VR318 using a PCR method to detect 472-C variants shows that these samples cannot be distinguished.

There are several lines of data supporting the selective advantage for Sabin 3 variants possessing U at 2493 in vivo, as well as in vitro. Stool isolate KW4, recovered 5 days post-vaccination, was shown previously to differ from the administered vaccine strain at three positions: 472=C, 2493= U, and 6061=U/C (20). Based on the data presented here, the intermediate level of neurovirulence observed for KW4 in that study can now be attributed to the mutation at 2493 as well as 472. Weeks-Levy et al. (24) found that two of three virus isolates recovered from nervous tissue (brain or spinal cord) of monkeys that had been injected intraspinally with NCl, the attenuated reference virus, possessed U at 2493. That isolate NCl-679B had U at 2493 without loss of the attenuated U at 472 may specifically relate to how this virus spread and replicated in the brain. The data are consistent with observations of increased neurovirulence for VR318 compared to LED3 as tested by CFR intrathalamic method.

The mechanism by which the change from U to C at 2493 attenuates LED3 compared VR318 is unclear. This mutation alters the sixth amino acid capsid protein VP1. In the three-dimensional structure of poliovirus, Hogle et al. (6) show that this region of VP1 is buried on the inside of the native virion. More recently, Fricks and Hogle (5) demonstrated that upon attachment to susceptible cells, the virion undergoes conformational changes resulting in release of capsid protein VP4 and externalization of the amino terminus of VP1. These authors demonstrated further that exposure of the amino terminus of VP1 was required for attachment to liposomes and proposed that these events play a role in the mechanism of cell entry. Consistent with these observations, Kirkegaard (8) described two poliovirus mutants with different small deletions in the amino terminal region of VP1 which flank either side of residue six as defective in the physical release of viral RNA from the capsid during normal infection. Both of these deletion mutants exhibited small plaque phenotype. From these data, it is easy to speculate that the mutation is Sabin 3 at position 2493 also affects viral uncoating.

In addition to the mutation in VP3 (2034) of Sabin 3, attenuation determinants have been mapped to the capsid proteins in Sabin 1 (14) and a type 2 strain (P2/712) which is closely related to Sabin 2 (16). Although these other mutations occur within capsid protein VP1, the structural mutation described in this study is the first one to be mapped to the amino terminal region of VP1.

While a number of embodiments of this invention have been described hereinabove, it is apparent that the basic constructions can be altered to provide other embodiments which utilize the processes, recombinant DNA molecules, cDNA molecules and transformed hosts of this invention. Therefore, it will be appreciated that the scope of this invention is to be defined by the claims appended hereto rather than by specific embodiments which have been presented hereinbefore by way of example.

TABLE 1

NEUROVIRULENCE OF LED3 AND VR318 STRAINS USING CFR NV TEST PROCEDURE

| GROUP | VIRUS | CELL SUBSTRATE | NUCLEOTIDE AT 472 | NUCLEOTIDE AT 2493 | NO. OF MONKEYS | MEAN LESION SCORE |
|---|---|---|---|---|---|---|
| A) INTRASPINAL[a] | | | | | | |
| 1 | RSO+2 | PCMK | U | C | 24 | 0.52 |
| 2 | RSO+2 | VERO | U | C | 12 | 0.36 |
| 3 | LED3+2 | VERO | U | C | 16 | 0.34 |
| 4 | VR318+2 | VERO | U | U | 16 | 1.31[b] |

| GROUP | VIRUS | CELL SUBSTRATE | NUCLEOTIDE AT 472 | NUCLEOTIDE AT 2493 | NO. OF MONKEYS | PERCENT POSITIVE |
|---|---|---|---|---|---|---|
| B) INTRATHALAMIC[c] | | | | | | |
| 5 | RSO+2 | PCMK | U | C | 120 | 4 |
| 6 | LED3+2 | VERO | U | C | 10 | 0 |
| 7 | VR318+2 | VERO | U | U | 10 | 20[d] |

[a] 0.2 ml of virus (titer $\geq$ 7.6 log $TCID_{50}$/ml) administered intraspinally.
[b] Group 4 > 1,2,3 ($p < 0.01$) by ANOVA and mean range testing.
[c] 0.5 ml of virus (titer $\geq$ 7.6 log $TCID_{50}$/ml) administered intracerebrally into the thalamic region of each hemisphere.
[d] Group 7 > 5,6 ($p < 0.05$) by Chi-square test.

TABLE 2

NEUROVIRULENCE OF LED3 AND VR318 STRAINS USING WHO NV TEST PROCEDURE[a]

| GROUP | VIRUS | CELL SUBSTRATE | NUCLEOTIDE AT 472 | NUCLEOTIDE AT 2493 | NO. OF MONKEYS | MEAN LESION SCORE |
|---|---|---|---|---|---|---|
| 1 | LED3+2 | VERO | U | C | 6 | 0.21[b] |
| 2 | NC1[c] | PCMK | U | U/C | 6 | 1.08 |
| 3 | VR318+2 | VERO | U | U | 6 | 1.51 |

[a] 0.1 ml of virus (titer 6.5 to 7.5 log $TCID_{50}$/ml) adminstered intraspinally.
[b] Group 2 < 1,3 ($p < 0.1$) by ANOVA and mean range testing.
[c] NC1 (SO+2) is an attenuated type 3 reference for the WHO NV test.

REFERENCES

1. Albrecht, P., J. C. Enterline, E. J. Boone, and M. J. Klutch. 1983. Polioviurs and polio anitbody assay in HEp-2 and Vero cell cultures. J. Biol. Stand. 11:91–97.
2. Chumakov, K. M., L. B. Powers, K. E. Noonan, I. B. Ronison and I. S. Levenbook. 1991. Correlation between amount of virus with altered nucleotide sequence and the monkey test for acceptability of oral poliovirus vaccine. Proc. Natl. Acad. Sci. U.S.A. 88:199–203.
3. Domingo, E. 1989. RNA virus evolution and the control of viral disease. Prog. Drug Res. 33;93–133.
4. Dunn, G., N. T. Begg, N. Cammack, and P. D. Minor. 1990. Virus exretion and mutation by infants following primary vaccination with live oral poliovaccine from two sources. J. Med. Virol. 32:92–95.
5. Fricks, C. E. and J. M. Hogle. 1990 Cell-induced conformational change in poliovirus: Externalization of the amino terminus of VP1 is responsible for liposome binding. J. Virol. 64:1934–1945.
6. Hogle, J. M., M. Chow, and D. J. Filman. 1985. Three-dimensional structure of poliovirus at 2.9A resolution. Science 229:1358–1365.
7. Kew, O. M., B. K. Nottay, M. H. Hatch, J. H. Nakano and J. F. Obijeski. 1981. Multiple changes can occur in the oral polio vaccines upon relication in humans. J. Gen. Virol. 56:337–347.
8. Kirkegaard, K. 1990. Mutations in VP1 of poliovirus specifically affect both encapsidation and release of viral RNA. J. Virol. 64:195–206.
9. Kohara, M., A. Shinobu, S. Kuge, B. L. Semler, T. Komatsu, M. Arita, H. Itoh and A. Nomoto. 1985. An infectious cDNA clone of the poliovirus Sabin strain could be used as a stable repository and inoculum for the oral polio live vaccine. Virology 151:21–30.
10. Laemmli, U. K. 1970. Cleavage of structural proteins during the assembly of the head of bacteriophage T4. Nature (London) 227:680–685.
11. Melnick, J. L., M. Benyesh-Melnick, and J. C. Brennan. 1959. Studies on live poliovirus vaccine. JAMA. 171:63–70.
12. Moss, E. G., R. E. O'Neill, and V. R. Racaniello. 1989. Mapping of attenuating sequences of an avirulent poliovirus type 2 strain. J. Virol. 63:1884–1890.
13. Nakano, J. H., M. H. Hatch, M. L. Thieme and B. Nottay. 1978. Parameters for differentiating vaccine-derived and wild poliovirus strains. Prog. Med. Virol. 24:178–206.
14. Nomoto, A. and E. Wimmer. 1987. Genetic studies of the antigenicity and the attenuation phenotype of poliovirus, p. 107–134. In W. C. Russell and J. W. Almond (ed.), Molecular basis of virus disease. Cambridge University Press, Cambridge.
15. Racaniello, V. R. 1988. Poliovirus neurovirulence. Adv. Virus Res. 34:217–246.
16. Ren, R., E. G. Moss, and V. R. Racaniello. 1991. Indentification of two determinants that attenuate vaccine-related type 2 poliovirus. J. Virol. 65:1377–1382.
17. Stanway, G., A. J. Cann, R. Hauptmann, P. Hughes, L. D. Clarke, R. C. Mountford, P. D. Minor, G. C. Schild, and J. W. Almond. 1983. The nucleotide sequence of poliovirus type 3 leon 12 $a_1$b: comparison with poliovirus type 1. Nucleic Acids Res. 11:5629–5643.
18. Stanway, G., P. J. Hughes, R. C. Mountford, P. Reeve, P. D. Minor, G. C. Schild, and J. W. Almond. 1984. Comparison of complete nucleotide sequences of the genomes of the neurovirulent poliovirus P3/Leon/37 and its attenuated Sabin vaccine derivative P3/Leon12$a_1$b. Proc. Natl. Acad. Sci. U.S.A. 81:1539–1543.
19. Stones, P. B., C. R. Macdonald, J. K. McDougall and P. F. Ramsbottom. 1964. Preparation and properties of a derivative of Sabin's type 3 poliovirus strain Leon 12$a_1$b. 10th Symposium of the European Association against Poliomyelitis, Warsaw, pp. 390–397.
20. Tatem, J. M., C. Weeks-Levy, S. J. Mento, S. J. MiMichele, A. Georgiu, W. F. Waterfiled, B. Sheip, C. Costalas, T. Davies, M. B. Ritchey and F. R. Cano. J. Med. Virol., in press.
21. Toyoda, H., Kohara, M., Kataoka, Y., Suganuma, T., Omata, T., Imura, N., and Nomoto, A. 1984. Complete nucleotide sequences of all three poliovirus serotype genomes: Implication for gentic relationship, gene function and antigenic determinants. J. Mol. Biol. 174:561:585.
22. United States Code of Federal Regulations. 1990. Poliouvirus vaccine live oral. Title 21, Sec. 630.10–17.
23. van der Werf, S., J. Bradley, E. Wimmer, F. W. Studier and J. J. Dunn. 1986. Sythesis of infectious poliovirus RNA by purified T7 RNA polymerase. Proc. Natl. Acad. Sci. U.S.A. 83:2330–2334.
24. Weeks-Levy, C., J. M. Tatem, S. J. DiMichele, W. Waterfield, A. F. Georigu and S. J. Mento. Submitted for publication.
25. Westrop, G. D., K. A. Wareham, D. M. A. Evans, G. Dunn, P. D. Minor, D. I. Magrath, F. Taffs, S. Marsden, M. A. Skinner, G. C. Schild and J. W. Almond. 1989. Genetic basis of attenuation of the Sabin type 3 oral poliovirus vaccine. J. Virol. 63:1338–1344.
26. World Health Organization. 1990. Requirements for poliomyelitis vaccine (oral). W. H. O. Tech. Rep. Ser. 800:30–36.

What is claimed is:

1. A full-length and infectious recombinant DNA molecule comprising a true RNA virus cDNA derived from a vaccine strain 3 poliovirus, said cDNA being selected from the group consisting of:
   (a) pLED3.2; and
   (b) cDNAs which code for the polypeptides encoded by pLED3.2.

2. A full-length and infectious recombinant DNA molecule comprising an RNA virus cDNA derived from a vaccine strain 3 poliovirus, said cDNA being selected from the group consisting of:
   (a) pLED3; and
   (b) cDNAs which code for the polypeptides encoded by pLED3.

3. The recombinant DNA molecule according to any of claims 1, or 2, wherein said RNA virus cDNA is operatively linked to a promoter of RNA transcription.

4. The recombinant DNA molecule according to claim 3, wherein said promoter is the T7 promoter.

5. The host according to claim 4, wherein said host is *E. coli*.

6. A host transformed with a recombinant DNA molecule according to any one of claims 1, or 2, said host being selected from the group consisting of bacteria, yeast and other fungi, insect cells and animal cells.

7. The host according to claim 6, wherein said host is an animal cell selected from the group consisting of Vero cells, HeLa cells, COS cells, CV-1 cells and primary monkey kidney cells.

8. A host transformed with a recombinant DNA molecule according to claim 3 said host being selected from the group consisting of bacteria, yeast and other fungi, insect cells and animal cells.

9. The host according to claim 8, wherein said host is an animal cell selected from the group consisting of Vero cells, HeLa cells, COS cells, CV-1 cells and primary monkey kidney cells.

* * * * *

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 7432 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: CDS
        ( B ) LOCATION: 743..7361

( x i ) SEQUENCE DESCRIPTION: SEQ ID NO:1:

```
TTAAAACAGC   TCTGGGGTTG   TTCCCACCCC   AGAGGCCCAC   GTGGCGGCTA   GTACACTGGT        60

ATCACGGTAC   CTTTGTACGC   CTGTTTTATA   CTCCCTCCCC   CGCAACTTAG   AAGCATACAA       120

TTCAAGCTCA   ATAGGAGGGG   GTGCAAGCCA   GCGCCTCCGT   GGGCAAGCAC   TACTGTTTCC       180

CCGGTGAGGC   CGCATAGACT   GTTCCCACGG   TTGAAAGTGT   CCGATCCGTT   ATCCGCTCAT       240

GTACTTCGAG   AAGCCTAGTA   TCGCTCTGGA   ATCTTGACG   CGTTGCGCTC   AGCACTCAAC       300

CCCGGAGTGT   AGCTTGGGCC   GATGAGTCTG   GACAGTCCCC   ACTGGCGACA   GTGGTCCAGG       360

CTGCGCTGGC   GGCCCACCTG   TGGCCCAAAG   CCACGGGACG   CTAGTTGTGA   ACAGGGTGTG       420

AAGAGCCTAT   TGAGCTACAT   GAGAGTCCTC   CGGCCCCTGA   ATGCGGCTAA   TTCTAACCAT       480

GGAGCAGGCA   GCTGCAACCC   AGCAGCCAGC   CTGTCGTAAC   GCGCAAGTCC   GTGGCGGAAC       540

CGACTACTTT   GGGTGTCCGT   GTTTCCTTTT   ATTCTTGAAT   GGCTGCTTAT   GGTGACAATC       600
```

| | | |
|---|---|---|
| ATAGATTGTT ATCATAAAGC GAGTTGGATT GGCCATCCAG TGTGAATCAG ATTAATTACT | | 660 |
| CCCTTGTTTG TTGGATCCAC TCCCGAAACG TTTTACTCCT TAACTTATTG AAATTGTTTG | | 720 |
| AAGACAGGAT TTCAGTGTCA CA ATG GGA GCT CAA GTA TCA TCC CAA AAA GTA | | 772 |
| | Met Gly Ala Gln Val Ser Ser Gln Lys Val | |
| | 1 5 10 | |
| GGC GCT CAC GAG AAT TCT AAC CGA GCC TAC GGT GGT TCT ACG ATC AAC | | 820 |
| Gly Ala His Glu Asn Ser Asn Arg Ala Tyr Gly Gly Ser Thr Ile Asn | | |
| 15 20 25 | | |
| TAC ACC ACA ATT AAT TAT TAT AAA GAT TCC GCA AGT AAT GCG GCG TCC | | 868 |
| Tyr Thr Thr Ile Asn Tyr Tyr Lys Asp Ser Ala Ser Asn Ala Ala Ser | | |
| 30 35 40 | | |
| AAA CAA GAT TAC TCA CAG GAT CCA TCA AAA TTC ACC GAG CCA CTA AAG | | 916 |
| Lys Gln Asp Tyr Ser Gln Asp Pro Ser Lys Phe Thr Glu Pro Leu Lys | | |
| 45 50 55 | | |
| GAC GTG CTC ATA AAA ACA GCT CCA GCA CTC AAT TCA CCA AAT GTG GAA | | 964 |
| Asp Val Leu Ile Lys Thr Ala Pro Ala Leu Asn Ser Pro Asn Val Glu | | |
| 60 65 70 | | |
| GCG TGT GGG TAT AGT GAT AGA GTG TTG CAA CTC ACT TTA GGC AAT TCC | | 1012 |
| Ala Cys Gly Tyr Ser Asp Arg Val Leu Gln Leu Thr Leu Gly Asn Ser | | |
| 75 80 85 90 | | |
| ACT ATT ACT ACA CAG GAG GCA GCA AAT TCA GTA GTG GCT TAC GGA CGT | | 1060 |
| Thr Ile Thr Thr Gln Glu Ala Ala Asn Ser Val Val Ala Tyr Gly Arg | | |
| 95 100 105 | | |
| TGG CCT GAG TTT ATT AGA GAT GAC GAA GCA AAC CCG GTG GAC CAA CCA | | 1108 |
| Trp Pro Glu Phe Ile Arg Asp Asp Glu Ala Asn Pro Val Asp Gln Pro | | |
| 110 115 120 | | |
| ACT GAA CCA GAT GTG GCT ACA TGC AGA TTC TAC ACA CTA GAC ACT GTA | | 1156 |
| Thr Glu Pro Asp Val Ala Thr Cys Arg Phe Tyr Thr Leu Asp Thr Val | | |
| 125 130 135 | | |
| ATG TGG GGT AAG GAG TCG AAA GGC TGG TGG TGG AAG TTA CCT GAC GCA | | 1204 |
| Met Trp Gly Lys Glu Ser Lys Gly Trp Trp Trp Lys Leu Pro Asp Ala | | |
| 140 145 150 | | |
| CTG AGA GAC ATG GGT CTG TTT GGA CAA AAC ATG TAT TAC CAC TAC CTA | | 1252 |
| Leu Arg Asp Met Gly Leu Phe Gly Gln Asn Met Tyr Tyr His Tyr Leu | | |
| 155 160 165 170 | | |
| GGA AGA TCC GGG TAC ACT GTG CAC GTG CAG TGT AAT GCA TCC AAA TTT | | 1300 |
| Gly Arg Ser Gly Tyr Thr Val His Val Gln Cys Asn Ala Ser Lys Phe | | |
| 175 180 185 | | |
| CAC CAA GGT GCA CTC GGG GTG TTT GCG ATT CCT GAG TAT TGT CTG GCG | | 1348 |
| His Gln Gly Ala Leu Gly Val Phe Ala Ile Pro Glu Tyr Cys Leu Ala | | |
| 190 195 200 | | |
| GGT GAC AGT GAC AAG CAA AGG TAC ACT AGT TAT GCA AAT GCG AAT CCA | | 1396 |
| Gly Asp Ser Asp Lys Gln Arg Tyr Thr Ser Tyr Ala Asn Ala Asn Pro | | |
| 205 210 215 | | |
| GGT GAA AGA GGG GGA AAA TTT TAC TCC CAA TTC AAC AAG GAT AAC GCA | | 1444 |
| Gly Glu Arg Gly Gly Lys Phe Tyr Ser Gln Phe Asn Lys Asp Asn Ala | | |
| 220 225 230 | | |
| GTA ACA TCC CCA AAA AGA GAG TTC TGC CCA GTG GAT TAT CTC CTG GGA | | 1492 |
| Val Thr Ser Pro Lys Arg Glu Phe Cys Pro Val Asp Tyr Leu Leu Gly | | |
| 235 240 245 250 | | |
| TGT GGG GTG TTA CTG GGA AAT GCC TTT GTA TAC CCA CAT CAA ATC ATT | | 1540 |
| Cys Gly Val Leu Leu Gly Asn Ala Phe Val Tyr Pro His Gln Ile Ile | | |
| 255 260 265 | | |
| AAT CTG AGG ACC AAC AAC AGC GCA ACT ATT GTC CTA CCA TAT GTG AAT | | 1588 |
| Asn Leu Arg Thr Asn Asn Ser Ala Thr Ile Val Leu Pro Tyr Val Asn | | |
| 270 275 280 | | |
| GCT TTG GCC ATT GAT TCA ATG GTT AAA CAC AAC AAC TGG GGC ATT GCC | | 1636 |
| Ala Leu Ala Ile Asp Ser Met Val Lys His Asn Asn Trp Gly Ile Ala | | |
| 285 290 295 | | |

| | | | | | | | | | | | | | | | | |
|---|---|---|---|---|---|---|---|---|---|---|---|---|---|---|---|---|
| ATT | CTG | CCC | TTA | TCA | CCG | CTG | GAT | TTT | GCT | CAA | GAT | TCA | TCA | GTT | GAA | 1684 |
| Ile | Leu | Pro | Leu | Ser | Pro | Leu | Asp | Phe | Ala | Gln | Asp | Ser | Ser | Val | Glu | |
| | 300 | | | | 305 | | | | | 310 | | | | | | |
| ATT | CCA | ATT | ACT | GTG | ACA | ATT | GCC | CCA | ATG | TGT | AGC | GAG | TTC | AAC | GGC | 1732 |
| Ile | Pro | Ile | Thr | Val | Thr | Ile | Ala | Pro | Met | Cys | Ser | Glu | Phe | Asn | Gly | |
| 315 | | | | | 320 | | | | | 325 | | | | | 330 | |
| CTT | CGC | AAC | GTG | ACT | GCA | CCT | AAA | TTT | CAA | GGA | CTA | CCA | GTG | TTG | AAC | 1780 |
| Leu | Arg | Asn | Val | Thr | Ala | Pro | Lys | Phe | Gln | Gly | Leu | Pro | Val | Leu | Asn | |
| | | | | 335 | | | | | 340 | | | | | 345 | | |
| ACT | CCT | GGT | AGT | AAC | CAG | TAC | CTG | ACG | TCA | GAC | AAC | CAC | CAA | TCA | CCA | 1828 |
| Thr | Pro | Gly | Ser | Asn | Gln | Tyr | Leu | Thr | Ser | Asp | Asn | His | Gln | Ser | Pro | |
| | | | 350 | | | | 355 | | | | | 360 | | | | |
| TGC | GCA | ATC | CCA | GAA | TTT | GAT | GTC | ACT | CCG | CCT | ATT | GAT | ATC | CCA | GGT | 1876 |
| Cys | Ala | Ile | Pro | Glu | Phe | Asp | Val | Thr | Pro | Pro | Ile | Asp | Ile | Pro | Gly | |
| | | 365 | | | | 370 | | | | | 375 | | | | | |
| GAG | GTT | AAA | AAC | ATG | ATG | GAG | CTC | GCC | GAG | ATA | GAC | ACC | ATG | ATT | CCT | 1924 |
| Glu | Val | Lys | Asn | Met | Met | Glu | Leu | Ala | Glu | Ile | Asp | Thr | Met | Ile | Pro | |
| | 380 | | | | | 385 | | | | | 390 | | | | | |
| CTC | AAT | TTG | GAG | AGC | ACC | AAG | AGA | AAC | ACA | ATG | GAC | ATG | TAC | AGA | GTT | 1972 |
| Leu | Asn | Leu | Glu | Ser | Thr | Lys | Arg | Asn | Thr | Met | Asp | Met | Tyr | Arg | Val | |
| 395 | | | | | 400 | | | | | 405 | | | | | 410 | |
| ACT | CTG | AGC | GAC | AGT | GCC | GAT | CTA | TCG | CAA | CCA | ATT | TTG | TGC | TTG | TCA | 2020 |
| Thr | Leu | Ser | Asp | Ser | Ala | Asp | Leu | Ser | Gln | Pro | Ile | Leu | Cys | Leu | Ser | |
| | | | | 415 | | | | | 420 | | | | | 425 | | |
| CTA | TCC | CCA | GCA | TTT | GAT | CCG | CGC | TTG | TCA | CAC | ACC | ATG | CTT | GGG | GAA | 2068 |
| Leu | Ser | Pro | Ala | Phe | Asp | Pro | Arg | Leu | Ser | His | Thr | Met | Leu | Gly | Glu | |
| | | | 430 | | | | 435 | | | | | 440 | | | | |
| GTA | CTG | AAC | TAT | TAT | ACT | CAT | TGG | GCC | GGG | TCC | TTG | AAA | TTT | ACC | TTC | 2116 |
| Val | Leu | Asn | Tyr | Tyr | Thr | His | Trp | Ala | Gly | Ser | Leu | Lys | Phe | Thr | Phe | |
| | | 445 | | | | 450 | | | | | 455 | | | | | |
| CTG | TTC | TGT | GGT | TCA | ATG | ATG | GCT | ACG | GGA | AAA | ATC | CTA | GTG | GCC | TAT | 2164 |
| Leu | Phe | Cys | Gly | Ser | Met | Met | Ala | Thr | Gly | Lys | Ile | Leu | Val | Ala | Tyr | |
| | 460 | | | | | 465 | | | | | 470 | | | | | |
| GCA | CCA | CCA | GGT | GCA | CAA | CCC | CCC | ACC | AGC | CGT | AAG | GAG | GCT | ATG | TTG | 2212 |
| Ala | Pro | Pro | Gly | Ala | Gln | Pro | Pro | Thr | Ser | Arg | Lys | Glu | Ala | Met | Leu | |
| 475 | | | | | 480 | | | | | 485 | | | | | 490 | |
| GGC | ACA | CAT | GTC | ATT | TGG | GAT | CTT | GGC | CTG | CAA | TCA | TCT | TGT | ACT | ATG | 2260 |
| Gly | Thr | His | Val | Ile | Trp | Asp | Leu | Gly | Leu | Gln | Ser | Ser | Cys | Thr | Met | |
| | | | | 495 | | | | | 500 | | | | | 505 | | |
| GTG | GTG | CCG | TGG | ATT | AGT | AAT | GTG | ACA | TAC | AGA | CAG | ACT | ACA | CAA | GAT | 2308 |
| Val | Val | Pro | Trp | Ile | Ser | Asn | Val | Thr | Tyr | Arg | Gln | Thr | Thr | Gln | Asp | |
| | | | 510 | | | | 515 | | | | | 520 | | | | |
| AGT | TTC | ACT | GAG | GGC | GGA | TAT | ATC | AGC | ATG | TTC | TAC | CAA | ACA | AGA | ATT | 2356 |
| Ser | Phe | Thr | Glu | Gly | Gly | Tyr | Ile | Ser | Met | Phe | Tyr | Gln | Thr | Arg | Ile | |
| | | 525 | | | | 530 | | | | | 535 | | | | | |
| GTG | GTG | CCA | CTG | TCC | ACC | CCT | AAG | AGT | ATG | AGC | ATG | CTG | GGG | TTT | GTG | 2404 |
| Val | Val | Pro | Leu | Ser | Thr | Pro | Lys | Ser | Met | Ser | Met | Leu | Gly | Phe | Val | |
| | 540 | | | | | 545 | | | | | 550 | | | | | |
| TCA | GCC | TGT | AAT | GAT | TTC | AGT | GTG | CGA | TTG | CTG | CGA | GAC | ACC | ACT | CAC | 2452 |
| Ser | Ala | Cys | Asn | Asp | Phe | Ser | Val | Arg | Leu | Leu | Arg | Asp | Thr | Thr | His | |
| 555 | | | | | 560 | | | | | 565 | | | | | 570 | |
| ATT | TCA | CAA | TCT | GCG | CTT | CCA | CAG | GGT | ATT | GAA | GAT | TTG | ACT | TCT | GAA | 2500 |
| Ile | Ser | Gln | Ser | Ala | Leu | Pro | Gln | Gly | Ile | Glu | Asp | Leu | Thr | Ser | Glu | |
| | | | | 575 | | | | | 580 | | | | | 585 | | |
| GTT | GCA | CAG | GGC | GCC | CTA | ACT | TTG | TCA | CTC | CCG | AAG | CAA | CAG | GAT | AGC | 2548 |
| Val | Ala | Gln | Gly | Ala | Leu | Thr | Leu | Ser | Leu | Pro | Lys | Gln | Gln | Asp | Ser | |
| | | | 590 | | | | 595 | | | | | 600 | | | | |
| TTA | CCT | GAT | ACT | AAG | GCC | AGT | GGC | CCG | GCG | CAT | TCC | AAG | GAG | GTA | CCT | 2596 |
| Leu | Pro | Asp | Thr | Lys | Ala | Ser | Gly | Pro | Ala | His | Ser | Lys | Glu | Val | Pro | |
| | | 605 | | | | 610 | | | | | 615 | | | | | |

| | | | | | | | | | | | | | | | | |
|---|---|---|---|---|---|---|---|---|---|---|---|---|---|---|---|---|
| GCA | CTC | ACT | GCA | GTC | GAG | ACT | GGA | GCC | ACC | AAT | CCT | CTG | GCA | CCA | TCC | 2644 |
| Ala | Leu | Thr | Ala | Val | Glu | Thr | Gly | Ala | Thr | Asn | Pro | Leu | Ala | Pro | Ser | |
| | 620 | | | | 625 | | | | | 630 | | | | | | |
| GAC | ACA | GTT | CAA | ACG | CGC | CAC | GTA | GTC | CAA | CGA | CGC | AGC | AGG | TCA | GAG | 2692 |
| Asp | Thr | Val | Gln | Thr | Arg | His | Val | Val | Gln | Arg | Arg | Ser | Arg | Ser | Glu | |
| 635 | | | | 640 | | | | | 645 | | | | | | 650 | |
| TCC | ACA | ATA | GAA | TCA | TTC | TTC | GCA | CGC | GGG | GCG | TGC | GTC | GCT | ATT | ATT | 2740 |
| Ser | Thr | Ile | Glu | Ser | Phe | Phe | Ala | Arg | Gly | Ala | Cys | Val | Ala | Ile | Ile | |
| | | | | 655 | | | | | 660 | | | | | 665 | | |
| GAG | GTG | GAC | AAT | GAA | CAA | CCA | ACC | ACC | CGG | GCA | CAG | AAA | CTA | TTT | GCC | 2788 |
| Glu | Val | Asp | Asn | Glu | Gln | Pro | Thr | Thr | Arg | Ala | Gln | Lys | Leu | Phe | Ala | |
| | | | 670 | | | | | 675 | | | | | 680 | | | |
| ATG | TGG | CGC | ATT | ACA | TAC | AAA | GAT | ACA | GTG | CAG | TTG | CGC | CGT | AAG | TTG | 2836 |
| Met | Trp | Arg | Ile | Thr | Tyr | Lys | Asp | Thr | Val | Gln | Leu | Arg | Arg | Lys | Leu | |
| | | 685 | | | | | 690 | | | | | 695 | | | | |
| GAG | TTT | TTC | ACA | TAC | TCT | CGT | TTT | GAC | ATG | GAA | TTC | ACC | TTC | GTG | GTA | 2884 |
| Glu | Phe | Phe | Thr | Tyr | Ser | Arg | Phe | Asp | Met | Glu | Phe | Thr | Phe | Val | Val | |
| | 700 | | | | | 705 | | | | | 710 | | | | | |
| ACC | GCC | AAC | TTC | ACC | AAC | GCT | AAT | AAT | GGG | CAT | GCA | CTC | AAC | CAG | GTG | 2932 |
| Thr | Ala | Asn | Phe | Thr | Asn | Ala | Asn | Asn | Gly | His | Ala | Leu | Asn | Gln | Val | |
| 715 | | | | | 720 | | | | | 725 | | | | | 730 | |
| TAC | CAG | ATA | ATG | TAC | ATC | CCC | CCA | GGG | GCA | CCC | ACA | CCA | AAG | TCA | TGG | 2980 |
| Tyr | Gln | Ile | Met | Tyr | Ile | Pro | Pro | Gly | Ala | Pro | Thr | Pro | Lys | Ser | Trp | |
| | | | | 735 | | | | | 740 | | | | | 745 | | |
| GAC | GAC | TAC | ACT | TGG | CAA | ACA | TCT | TCC | AAC | CCG | TCC | ATA | TTT | TAC | ACC | 3028 |
| Asp | Asp | Tyr | Thr | Trp | Gln | Thr | Ser | Ser | Asn | Pro | Ser | Ile | Phe | Tyr | Thr | |
| | | | 750 | | | | | 755 | | | | | 760 | | | |
| TAT | GGG | GCT | GCC | CCG | GCG | CGA | ATC | TCA | GTG | CCA | TAC | GTG | GGG | TTA | GCC | 3076 |
| Tyr | Gly | Ala | Ala | Pro | Ala | Arg | Ile | Ser | Val | Pro | Tyr | Val | Gly | Leu | Ala | |
| | | 765 | | | | | 770 | | | | | 775 | | | | |
| AAT | GCT | TAC | TCG | CAC | TTT | TAC | GAC | GGC | TTC | GCC | AAG | GTG | CCA | TTG | AAG | 3124 |
| Asn | Ala | Tyr | Ser | His | Phe | Tyr | Asp | Gly | Phe | Ala | Lys | Val | Pro | Leu | Lys | |
| | 780 | | | | | 785 | | | | | 790 | | | | | |
| ACA | GAT | GCC | AAT | GAC | CAG | ATT | GGT | GAT | TCC | TTG | TAC | AGC | GCC | ATG | ACA | 3172 |
| Thr | Asp | Ala | Asn | Asp | Gln | Ile | Gly | Asp | Ser | Leu | Tyr | Ser | Ala | Met | Thr | |
| 795 | | | | | 800 | | | | | 805 | | | | | 810 | |
| GTT | GAT | GAC | TTT | GGT | GTA | TTG | GCA | GTT | CGT | GTT | GTC | AAT | GAT | CAC | AAC | 3220 |
| Val | Asp | Asp | Phe | Gly | Val | Leu | Ala | Val | Arg | Val | Val | Asn | Asp | His | Asn | |
| | | | | 815 | | | | | 820 | | | | | 825 | | |
| CCC | ACT | AAA | GTA | ACC | TCC | AAA | GTC | CGC | ATT | TAC | ATG | AAA | CCC | AAA | CAC | 3268 |
| Pro | Thr | Lys | Val | Thr | Ser | Lys | Val | Arg | Ile | Tyr | Met | Lys | Pro | Lys | His | |
| | | | 830 | | | | | 835 | | | | | 840 | | | |
| GTA | CGT | GTC | TGG | TGC | CCT | AGA | CCG | CCG | CGC | GCG | GTA | CCT | TAT | TAT | GGA | 3316 |
| Val | Arg | Val | Trp | Cys | Pro | Arg | Pro | Pro | Arg | Ala | Val | Pro | Tyr | Tyr | Gly | |
| | | 845 | | | | | 850 | | | | | 855 | | | | |
| CCA | GGG | GTG | GAC | TAT | AGG | AAC | AAC | TTG | GAC | CCC | TTA | TCT | GAG | AAA | GGT | 3364 |
| Pro | Gly | Val | Asp | Tyr | Arg | Asn | Asn | Leu | Asp | Pro | Leu | Ser | Glu | Lys | Gly | |
| | 860 | | | | | 865 | | | | | 870 | | | | | |
| TTG | ACC | ACA | TAT | GGC | TTT | GGG | CAT | CAG | AAT | AAA | GCT | GTG | TAC | ACT | GCT | 3412 |
| Leu | Thr | Thr | Tyr | Gly | Phe | Gly | His | Gln | Asn | Lys | Ala | Val | Tyr | Thr | Ala | |
| 875 | | | | | 880 | | | | | 885 | | | | | 890 | |
| GGT | TAC | AAG | ATC | TGC | AAC | TAC | CAT | CTC | GCC | ACT | AAG | GAG | GAT | TTA | CAA | 3460 |
| Gly | Tyr | Lys | Ile | Cys | Asn | Tyr | His | Leu | Ala | Thr | Lys | Glu | Asp | Leu | Gln | |
| | | | | 895 | | | | | 900 | | | | | 905 | | |
| AAT | GCT | GTA | AGC | ATC | ATG | TGG | AAT | AGA | GAC | CTC | TTG | GTT | GTT | GAA | TCA | 3508 |
| Asn | Ala | Val | Ser | Ile | Met | Trp | Asn | Arg | Asp | Leu | Leu | Val | Val | Glu | Ser | |
| | | | 910 | | | | | 915 | | | | | 920 | | | |
| AAA | GCT | CAA | GGT | ACC | GAC | TCA | ATA | GCA | AGG | TGC | AAT | TGC | AAT | GCA | GGG | 3556 |
| Lys | Ala | Gln | Gly | Thr | Asp | Ser | Ile | Ala | Arg | Cys | Asn | Cys | Asn | Ala | Gly | |
| | | 925 | | | | | 930 | | | | | 935 | | | | |

```
GTG  TAC  TAT  TGT  GAG  TCC  AGA  AGG  AAA  TAC  TAC  CCT  GTG  TCG  TTT  GTG      3604
Val  Tyr  Tyr  Cys  Glu  Ser  Arg  Arg  Lys  Tyr  Tyr  Pro  Val  Ser  Phe  Val
940                      945                     950

GGA  CCC  ACC  TTC  CAA  TAC  ATG  GAG  GCT  AAT  GAC  TAC  TAC  CCA  GCT  AGA      3652
Gly  Pro  Thr  Phe  Gln  Tyr  Met  Glu  Ala  Asn  Asp  Tyr  Tyr  Pro  Ala  Arg
955                      960                     965                      970

TAC  CAA  TCC  CAC  ATG  TTA  ATC  GGG  CAC  GGC  TTT  GCC  TCA  CCA  GGT  GAC      3700
Tyr  Gln  Ser  His  Met  Leu  Ile  Gly  His  Gly  Phe  Ala  Ser  Pro  Gly  Asp
                         975                     980                      985

TGT  GGT  GGT  ATC  CTT  AGG  TGT  CAA  CAT  GGC  GTC  ATC  GGA  ATC  GTG  ACA      3748
Cys  Gly  Gly  Ile  Leu  Arg  Cys  Gln  His  Gly  Val  Ile  Gly  Ile  Val  Thr
               990                      995                     1000

GCT  GGT  GGA  GAG  GGA  TTA  GTC  GCA  TTC  TCT  GAC  ATA  AGG  GAC  TTG  TAT      3796
Ala  Gly  Gly  Glu  Gly  Leu  Val  Ala  Phe  Ser  Asp  Ile  Arg  Asp  Leu  Tyr
1005                     1010                    1015

GCT  TAC  GAG  GAA  GAG  GCC  ATG  GAG  CAG  GGC  ATT  TCA  AAC  TAT  ATT  GAG      3844
Ala  Tyr  Glu  Glu  Glu  Ala  Met  Glu  Gln  Gly  Ile  Ser  Asn  Tyr  Ile  Glu
1020                     1025                    1030

TCA  CTC  GGT  GCT  GCG  TTC  GGT  AGT  GGG  TTC  ACT  CAG  CAA  ATA  GGG  GAT      3892
Ser  Leu  Gly  Ala  Ala  Phe  Gly  Ser  Gly  Phe  Thr  Gln  Gln  Ile  Gly  Asp
1035                     1040                    1045                     1050

AAG  ATA  TCA  GAA  CTA  ACC  AGC  ATG  GTG  ACC  AGC  ACG  ATT  ACA  GAG  AAG      3940
Lys  Ile  Ser  Glu  Leu  Thr  Ser  Met  Val  Thr  Ser  Thr  Ile  Thr  Glu  Lys
                         1055                    1060                     1065

CTA  CTT  AAA  AAC  CTA  ATC  AAA  ATT  ATT  TCA  TCT  CTG  GTG  ATT  ATC  ACT      3988
Leu  Leu  Lys  Asn  Leu  Ile  Lys  Ile  Ile  Ser  Ser  Leu  Val  Ile  Ile  Thr
               1070                     1075                    1080

AGA  AAT  TAC  GAA  GAT  ACC  ACC  ACA  GTG  CTC  GCC  ACT  CTA  GCT  CTT  CTT      4036
Arg  Asn  Tyr  Glu  Asp  Thr  Thr  Thr  Val  Leu  Ala  Thr  Leu  Ala  Leu  Leu
1085                     1090                    1095

GGG  TGT  GAT  GTT  TCA  CCG  TGG  CAA  TGG  CTG  AAG  AAG  AAA  GCA  TGT  GAC      4084
Gly  Cys  Asp  Val  Ser  Pro  Trp  Gln  Trp  Leu  Lys  Lys  Lys  Ala  Cys  Asp
1100                     1105                    1110

ACT  TTG  GAG  ATT  CCC  TAT  GTT  ATT  AGA  CAG  GGT  GAT  AGT  TGG  TTG  AAA      4132
Thr  Leu  Glu  Ile  Pro  Tyr  Val  Ile  Arg  Gln  Gly  Asp  Ser  Trp  Leu  Lys
1115                     1120                    1125                     1130

AAA  TTT  ACT  GAG  GCG  TGC  AAC  GCA  GCT  AAG  GGG  TTG  GAA  TGG  GTG  TCC      4180
Lys  Phe  Thr  Glu  Ala  Cys  Asn  Ala  Ala  Lys  Gly  Leu  Glu  Trp  Val  Ser
                         1135                    1140                     1145

AAC  AAA  ATC  TCA  AAA  TTT  ATT  GAC  TGG  TTG  AGA  GAA  AGA  ATC  ATC  CCA      4228
Asn  Lys  Ile  Ser  Lys  Phe  Ile  Asp  Trp  Leu  Arg  Glu  Arg  Ile  Ile  Pro
               1150                     1155                    1160

CAA  GCC  AGG  GAC  AAG  CTT  GAG  TTT  GTA  ACC  AAA  TTG  AAA  CAG  TTG  GAA      4276
Gln  Ala  Arg  Asp  Lys  Leu  Glu  Phe  Val  Thr  Lys  Leu  Lys  Gln  Leu  Glu
1165                     1170                    1175

ATG  CTA  GAG  AAT  CAG  ATA  TCC  ACA  ATA  CAC  CAA  TCT  TGT  CCA  AGT  CAG      4324
Met  Leu  Glu  Asn  Gln  Ile  Ser  Thr  Ile  His  Gln  Ser  Cys  Pro  Ser  Gln
1180                     1185                    1190

GAA  CAC  CAG  GAA  ATT  TTG  TTC  AAC  AAT  GTA  CGC  TGG  TTG  TCC  ATT  CAA      4372
Glu  His  Gln  Glu  Ile  Leu  Phe  Asn  Asn  Val  Arg  Trp  Leu  Ser  Ile  Gln
1195                     1200                    1205                     1210

TCC  AAG  AGA  TTC  GCT  CCA  TTG  TAC  GCA  CTT  GAG  GCC  AAG  AGA  ATA  CAA      4420
Ser  Lys  Arg  Phe  Ala  Pro  Leu  Tyr  Ala  Leu  Glu  Ala  Lys  Arg  Ile  Gln
               1215                     1220                    1225

AAG  TTG  GAA  CAC  ACC  ATT  AAT  AAT  TAC  ATA  CAG  TTC  AAG  AGC  AAA  CAC      4468
Lys  Leu  Glu  His  Thr  Ile  Asn  Asn  Tyr  Ile  Gln  Phe  Lys  Ser  Lys  His
                         1230                    1235                     1240

CGT  ATT  GAG  CCA  GTA  TGT  TTG  TTA  GTG  CAT  GGG  AGC  CCA  GGT  ACA  GGA      4516
Arg  Ile  Glu  Pro  Val  Cys  Leu  Leu  Val  His  Gly  Ser  Pro  Gly  Thr  Gly
1245                     1250                    1255
```

```
AAA TCA GTT GCG ACT AAC CTA ATT GCT AGA GCC ATA GCT GAG AAA GAG     4564
Lys Ser Val Ala Thr Asn Leu Ile Ala Arg Ala Ile Ala Glu Lys Glu
    1260                1265                1270

AAC ACC TCC ACC TAC TCG CTA CCA CCG GAC CCG TCT CAC TTT GAT GGA     4612
Asn Thr Ser Thr Tyr Ser Leu Pro Pro Asp Pro Ser His Phe Asp Gly
1275                1280                1285                1290

TAC AAA CAA CAA GGT GTG GTT ATC ATG GAC GAC CTA AAC CAA AAC CCG     4660
Tyr Lys Gln Gln Gly Val Val Ile Met Asp Asp Leu Asn Gln Asn Pro
                1295                1300                1305

GAT GGG GCA GAT ATG AAG CTC TTT TGT CAA ATG GTG TCC ACT GTG GAG     4708
Asp Gly Ala Asp Met Lys Leu Phe Cys Gln Met Val Ser Thr Val Glu
                    1310                1315                1320

TTT ATC CCA CCT ATG GCC TCG CTG GAA GAG AAA GGC ATT CTG TTC ACA     4756
Phe Ile Pro Pro Met Ala Ser Leu Glu Glu Lys Gly Ile Leu Phe Thr
            1325                1330                1335

TCC AAC TAT GTT TTA GCC TCC ACC AAC TCC AGT CGC ATC ACA CCA CCT     4804
Ser Asn Tyr Val Leu Ala Ser Thr Asn Ser Ser Arg Ile Thr Pro Pro
        1340                1345                1350

ACA GTA GCC CAC AGT GAC GCT CTG GCC AGG AGG TTC GCT TTC GAT ATG     4852
Thr Val Ala His Ser Asp Ala Leu Ala Arg Arg Phe Ala Phe Asp Met
1355                1360                1365                1370

GAT ATT CAA GTG ATG GGC GAG TAC TCC AGA GAT GGT AAA CTC AAC ATG     4900
Asp Ile Gln Val Met Gly Glu Tyr Ser Arg Asp Gly Lys Leu Asn Met
                    1375                1380                1385

GCA ATG GCT ACT GAG ACG TGC AAG GAC TGC CAC CAA CCA GCA AAC TTC     4948
Ala Met Ala Thr Glu Thr Cys Lys Asp Cys His Gln Pro Ala Asn Phe
            1390                1395                1400

AAA AGA TGC TGT CCT TTA GTG TGT GGT AAG GCA ATT CAG TTA ATG GAC     4996
Lys Arg Cys Cys Pro Leu Val Cys Gly Lys Ala Ile Gln Leu Met Asp
        1405                1410                1415

AAA TCT TCC AGA GTT AGG TAC AGT GTT GAC CAG ATT ACT ACA ATG ATT     5044
Lys Ser Ser Arg Val Arg Tyr Ser Val Asp Gln Ile Thr Thr Met Ile
1420                1425                1430

ATC AAC GAG AGA AAC AGA AGA TCT AAC ATT GGC AAT TGC ATG GAG GCT     5092
Ile Asn Glu Arg Asn Arg Arg Ser Asn Ile Gly Asn Cys Met Glu Ala
1435                1440                1445                1450

TTG TTC CAA GGA CCA CTC CAG TAC AAA GAC CTG AAA ATT GAC ATC AAG     5140
Leu Phe Gln Gly Pro Leu Gln Tyr Lys Asp Leu Lys Ile Asp Ile Lys
                    1455                1460                1465

ACG AGG CCC CCC CCT GAA TGC ATC AAT GAT CTG CTT CAA GCA GTT GAC     5188
Thr Arg Pro Pro Pro Glu Cys Ile Asn Asp Leu Leu Gln Ala Val Asp
            1470                1475                1480

TCC CAG GAA GTG AGG GAT TAT TGT GAA AAG AAA GGA TGG ATC GTC AAC     5236
Ser Gln Glu Val Arg Asp Tyr Cys Glu Lys Lys Gly Trp Ile Val Asn
        1485                1490                1495

ATC ACT AGC CAA GTT CAA ACA GAG AGA AAC ATT AAC CGA GCA ATG ACC     5284
Ile Thr Ser Gln Val Gln Thr Glu Arg Asn Ile Asn Arg Ala Met Thr
    1500                1505                1510

ATT TTG CAG GCA GTG ACA ACT TTC GCC GCA GTG GCT GGT GTC GTG TAC     5332
Ile Leu Gln Ala Val Thr Thr Phe Ala Ala Val Ala Gly Val Val Tyr
1515                1520                1525                1530

GTC ATG TAC AAG TTA TTC GCT GGA CAC CAG GGA GCA TAC ACT GGT CTG     5380
Val Met Tyr Lys Leu Phe Ala Gly His Gln Gly Ala Tyr Thr Gly Leu
                    1535                1540                1545

CCA AAC AAA AGA CCC AAT GTG CCC ACC ATT AGA GCA GCA AAA GTG CAA     5428
Pro Asn Lys Arg Pro Asn Val Pro Thr Ile Arg Ala Ala Lys Val Gln
            1550                1555                1560

GGG CCT GGG TTT GAC TAT GCA GTG GCT ATG GCT AAA AGA AAC ATT GTT     5476
Gly Pro Gly Phe Asp Tyr Ala Val Ala Met Ala Lys Arg Asn Ile Val
        1565                1570                1575
```

| | | | | | | | | | | | | | | | | |
|---|---|---|---|---|---|---|---|---|---|---|---|---|---|---|---|---|
| ACA | GCA | ACT | ACT | AGC | AAA | GGG | GAG | TTC | ACA | ATG | CTA | GGA | GTC | CAC | GAC | 5524 |
| Thr | Ala | Thr | Thr | Ser | Lys | Gly | Glu | Phe | Thr | Met | Leu | Gly | Val | His | Asp | |
| | | | 1580 | | | 1585 | | | | 1590 | | | | | | |
| AAC | GTG | GCC | ATT | TTA | CCA | ACT | CAT | GCC | TCA | CCT | GGT | GAG | AGT | ATT | GTA | 5572 |
| Asn | Val | Ala | Ile | Leu | Pro | Thr | His | Ala | Ser | Pro | Gly | Glu | Ser | Ile | Val | |
| 1595 | | | | 1600 | | | | 1605 | | | | | 1610 | | | |
| ATT | GAT | GGC | AAA | GAG | GTT | GAA | ATC | CTA | GAC | GCT | AAA | GCC | CTC | GAA | GAT | 5620 |
| Ile | Asp | Gly | Lys | Glu | Val | Glu | Ile | Leu | Asp | Ala | Lys | Ala | Leu | Glu | Asp | |
| | | | | 1615 | | | | 1620 | | | | | 1625 | | | |
| CAG | GCA | GGC | ACT | AAT | CTG | GAA | ATC | ACC | ATA | ATA | ACC | CTC | AAA | AGA | AAT | 5668 |
| Gln | Ala | Gly | Thr | Asn | Leu | Glu | Ile | Thr | Ile | Ile | Thr | Leu | Lys | Arg | Asn | |
| | | | 1630 | | | | 1635 | | | | | 1640 | | | | |
| GAA | AAG | TTC | AGA | GAT | ATC | AGA | CAA | CAC | ATA | CCC | ACT | CAA | ATC | ACC | GAG | 5716 |
| Glu | Lys | Phe | Arg | Asp | Ile | Arg | Gln | His | Ile | Pro | Thr | Gln | Ile | Thr | Glu | |
| | | 1645 | | | | | 1650 | | | | | 1655 | | | | |
| ACG | AAT | GAT | GGA | GTT | CTG | ATT | GTG | AAC | ACT | AGT | AAG | TAC | CCC | AAC | ATG | 5764 |
| Thr | Asn | Asp | Gly | Val | Leu | Ile | Val | Asn | Thr | Ser | Lys | Tyr | Pro | Asn | Met | |
| 1660 | | | | | 1665 | | | | | 1670 | | | | | | |
| TAT | GTT | CCT | GTC | GGT | GCT | GTG | ACT | GAG | CAG | GGA | TAC | CTA | AAT | CTC | GGT | 5812 |
| Tyr | Val | Pro | Val | Gly | Ala | Val | Thr | Glu | Gln | Gly | Tyr | Leu | Asn | Leu | Gly | |
| 1675 | | | | 1680 | | | | | 1685 | | | | | 1690 | | |
| GGG | CGC | CAG | ACT | GCT | CGT | ATT | CTA | ATG | TAC | AAC | TTT | CCA | ACC | AGA | GCT | 5860 |
| Gly | Arg | Gln | Thr | Ala | Arg | Ile | Leu | Met | Tyr | Asn | Phe | Pro | Thr | Arg | Ala | |
| | | | | 1695 | | | | | 1700 | | | | | 1705 | | |
| GGT | CAG | TGT | GGT | GGA | GTC | ATC | ACA | TGC | ACT | GGG | AAA | GTC | ATC | GGG | ATG | 5908 |
| Gly | Gln | Cys | Gly | Gly | Val | Ile | Thr | Cys | Thr | Gly | Lys | Val | Ile | Gly | Met | |
| | | | | 1710 | | | | | 1715 | | | | | 1720 | | |
| CAC | GTT | GGT | GGG | AAT | GGT | TCA | CAT | GGG | TTT | GCA | GCG | GCC | CTG | AAG | CGG | 5956 |
| His | Val | Gly | Gly | Asn | Gly | Ser | His | Gly | Phe | Ala | Ala | Ala | Leu | Lys | Arg | |
| | | | 1725 | | | | 1730 | | | | | 1735 | | | | |
| TCA | TAC | TTC | ACT | CAG | AGC | CAA | GGT | GAA | ATC | CAG | TGG | ATG | AGA | CCA | TCA | 6004 |
| Ser | Tyr | Phe | Thr | Gln | Ser | Gln | Gly | Glu | Ile | Gln | Trp | Met | Arg | Pro | Ser | |
| | | 1740 | | | | | 1745 | | | | | 1750 | | | | |
| AAG | GAG | GCA | GGG | TAT | CCA | ATT | ATA | AAC | GCC | CCA | ACC | AAG | ACC | AAG | CTC | 6052 |
| Lys | Glu | Ala | Gly | Tyr | Pro | Ile | Ile | Asn | Ala | Pro | Thr | Lys | Thr | Lys | Leu | |
| 1755 | | | | | 1760 | | | | | 1765 | | | | | 1770 | |
| GAG | CCC | AGT | GCT | TTC | CAC | TAT | GTG | TTT | GAA | GGA | GTA | AAG | GAA | CCA | GCA | 6100 |
| Glu | Pro | Ser | Ala | Phe | His | Tyr | Val | Phe | Glu | Gly | Val | Lys | Glu | Pro | Ala | |
| | | | | 1775 | | | | | 1780 | | | | | 1785 | | |
| GTC | CTC | ACA | AAG | AAT | GAT | CCC | AGA | CTC | AAA | ACA | GAC | TTT | GAA | GAA | GCA | 6148 |
| Val | Leu | Thr | Lys | Asn | Asp | Pro | Arg | Leu | Lys | Thr | Asp | Phe | Glu | Glu | Ala | |
| | | | 1790 | | | | | 1795 | | | | | 1800 | | | |
| ATC | TTC | TCT | AAG | TAT | GTA | GGG | AAC | AAG | ATC | ACT | GAG | GTG | GAT | GAG | TAC | 6196 |
| Ile | Phe | Ser | Lys | Tyr | Val | Gly | Asn | Lys | Ile | Thr | Glu | Val | Asp | Glu | Tyr | |
| | | | 1805 | | | | | 1810 | | | | | 1815 | | | |
| ATG | AAA | GAG | GCA | GTG | GAC | CAT | TAT | GCT | GGA | CAA | CTT | ATG | TCG | CTG | GAT | 6244 |
| Met | Lys | Glu | Ala | Val | Asp | His | Tyr | Ala | Gly | Gln | Leu | Met | Ser | Leu | Asp | |
| | 1820 | | | | | 1825 | | | | | 1830 | | | | | |
| ATC | AGC | ACA | GAG | CAA | ATG | TGT | CTA | GAA | GAC | GCC | ATG | TAT | GGT | ACT | GAT | 6292 |
| Ile | Ser | Thr | Glu | Gln | Met | Cys | Leu | Glu | Asp | Ala | Met | Tyr | Gly | Thr | Asp | |
| 1835 | | | | | 1840 | | | | | 1845 | | | | | 1850 | |
| GGT | CTG | GAG | GCG | CTA | GAT | CTG | TCT | ACC | AGT | GCC | GGG | TAC | CCC | TAC | GTG | 6340 |
| Gly | Leu | Glu | Ala | Leu | Asp | Leu | Ser | Thr | Ser | Ala | Gly | Tyr | Pro | Tyr | Val | |
| | | | | 1855 | | | | | 1860 | | | | | 1865 | | |
| GCA | ATG | GGG | AAG | AAG | AAG | AGA | GAT | ATC | CTA | AAC | AAG | CAA | ACC | AGA | GAC | 6388 |
| Ala | Met | Gly | Lys | Lys | Lys | Arg | Asp | Ile | Leu | Asn | Lys | Gln | Thr | Arg | Asp | |
| | | | 1870 | | | | | 1875 | | | | | 1880 | | | |
| ACC | AAA | GAA | ATG | CAA | AGA | CTT | TTG | GAC | GCT | TAC | GGA | ATC | AAC | CTA | CCA | 6436 |
| Thr | Lys | Glu | Met | Gln | Arg | Leu | Leu | Asp | Ala | Tyr | Gly | Ile | Asn | Leu | Pro | |
| | 1885 | | | | | 1890 | | | | | 1895 | | | | | |

```
TTA GTG ACA TAT GTC AAG GAC GAG CTG AGG TCC AAA ACA AAA GTG GAA        6484
Leu Val Thr Tyr Val Lys Asp Glu Leu Arg Ser Lys Thr Lys Val Glu
        1900            1905                1910

CAG GGA AAA TCC AGA CTG ATT GAA GCT TCC AGT CTA AAT GAC TCA GTG        6532
Gln Gly Lys Ser Arg Leu Ile Glu Ala Ser Ser Leu Asn Asp Ser Val
1915            1920                1925                    1930

GCC ATG AGA ATG GCA TTT GGA AAC CTT TAT GCA GCA TTC CAC AGG AAT        6580
Ala Met Arg Met Ala Phe Gly Asn Leu Tyr Ala Ala Phe His Arg Asn
                1935                1940                1945

CCA GGG GTC GTC ACT GGT AGT GCA GTT GGA TGC GAT CCA GAC CTA TTC        6628
Pro Gly Val Val Thr Gly Ser Ala Val Gly Cys Asp Pro Asp Leu Phe
            1950                1955                1960

TGG AGC AAG ATC CCA GTG TTG ATG GAA GAA AAG CTA TTT GCC TTT GAT        6676
Trp Ser Lys Ile Pro Val Leu Met Glu Glu Lys Leu Phe Ala Phe Asp
        1965                1970                1975

TAC ACA GGA TAC GAC GCA TCA CTT AGC CCA GCT TGG TTT GAG GCA CTC        6724
Tyr Thr Gly Tyr Asp Ala Ser Leu Ser Pro Ala Trp Phe Glu Ala Leu
    1980                1985                1990

AAG ATG GTG TTA GAG AAA ATT GGT TTT GGA GAT AGA GTG GAT TAC ATA        6772
Lys Met Val Leu Glu Lys Ile Gly Phe Gly Asp Arg Val Asp Tyr Ile
1995                2000                2005                2010

GAC TAC CTT AAC CAT TCA CAC CAC TTG TAC AAA AAC AAG ATA TAT TGT        6820
Asp Tyr Leu Asn His Ser His His Leu Tyr Lys Asn Lys Ile Tyr Cys
            2015                2020                2025

GTT AAG GGC GGC ATG CCA TCT GGC TGC TCC GGC ACT TCA ATT TTT AAT        6868
Val Lys Gly Gly Met Pro Ser Gly Cys Ser Gly Thr Ser Ile Phe Asn
        2030                2035                2040

TCA ATG ATT AAC AAT TTG ATC ATT AGG ACG CTT TTA CTG AAA ACC TAC        6916
Ser Met Ile Asn Asn Leu Ile Ile Arg Thr Leu Leu Leu Lys Thr Tyr
    2045                2050                2055

AAG GGC ATA GAT TTG GAC CAC TTA AAA ATG ATT GCC TAT GGT GAC GAT        6964
Lys Gly Ile Asp Leu Asp His Leu Lys Met Ile Ala Tyr Gly Asp Asp
2060                2065                2070

GTA ATA GCT TCC TAT CCC CAT GAG GTT GAC GCT AGT CTC CTA GCC CAA        7012
Val Ile Ala Ser Tyr Pro His Glu Val Asp Ala Ser Leu Leu Ala Gln
2075            2080                2085                    2090

TCA GGA AAA GAC TAT GGA CTA ACC ATG ACT CCG GCA GAT AAA TCT GCC        7060
Ser Gly Lys Asp Tyr Gly Leu Thr Met Thr Pro Ala Asp Lys Ser Ala
            2095                2100                2105

ACT TTT GAG ACA GTC ACA TGG GAG AAT GTA ACT TTC TTG AAA AGA TTC        7108
Thr Phe Glu Thr Val Thr Trp Glu Asn Val Thr Phe Leu Lys Arg Phe
                2110                2115                2120

TTC AGA GCA GAT GAG AAA TAC CCC TTC CTC ATA CAT CCA GTA ATG CCA        7156
Phe Arg Ala Asp Glu Lys Tyr Pro Phe Leu Ile His Pro Val Met Pro
            2125                2130                2135

ATG AAG GAA ATT CAT GAA TCA ATC AGA TGG ACA AAA GAT CCT CGG AAT        7204
Met Lys Glu Ile His Glu Ser Ile Arg Trp Thr Lys Asp Pro Arg Asn
        2140                2145                2150

ACG CAG GAC CAT GTA CGC TCC TTG TGT CTA TTG GCT TGG CAC AAC GGG        7252
Thr Gln Asp His Val Arg Ser Leu Cys Leu Leu Ala Trp His Asn Gly
2155                2160                2165                2170

GAA GAA GAA TAC AAC AAA TTT TTA GCT AAA ATT AGG AGT GTG CCA ATC        7300
Glu Glu Glu Tyr Asn Lys Phe Leu Ala Lys Ile Arg Ser Val Pro Ile
            2175                2180                2185

GGA AGA GCT TTG TTG CTC CCA GAG TAC TCA ACA TTG TAC CGC CGT TGG        7348
Gly Arg Ala Leu Leu Leu Pro Glu Tyr Ser Thr Leu Tyr Arg Arg Trp
        2190                2195                2200

CTT GAC TCA TTT T AGTAACCCTA CCTCAGTCGA ATTGGATTGG GTCATACTGT          7401
Leu Asp Ser Phe
        2205
```

TGTAGGGGTA AATTTTTCTT TAATTCGGAG G    7432

(2) INFORMATION FOR SEQ ID NO:2:

(i) SEQUENCE CHARACTERISTICS:
        (A) LENGTH: 2206 amino acids
        (B) TYPE: amino acid
        (D) TOPOLOGY: linear (ii) MOLECULE TYPE: protein (xi) SEQUENCE DESCRIPTION: SEQ ID NO:2:

```
Met Gly Ala Gln Val Ser Ser Gln Lys Val Gly Ala His Glu Asn Ser
 1               5                  10                  15

Asn Arg Ala Tyr Gly Gly Ser Thr Ile Asn Tyr Thr Thr Ile Asn Tyr
            20                  25                  30

Tyr Lys Asp Ser Ala Ser Asn Ala Ala Ser Lys Gln Asp Tyr Ser Gln
        35                  40                  45

Asp Pro Ser Lys Phe Thr Glu Pro Leu Lys Asp Val Leu Ile Lys Thr
    50                  55                  60

Ala Pro Ala Leu Asn Ser Pro Asn Val Glu Ala Cys Gly Tyr Ser Asp
65                  70                  75                  80

Arg Val Leu Gln Leu Thr Leu Gly Asn Ser Thr Ile Thr Thr Gln Glu
                85                  90                  95

Ala Ala Asn Ser Val Val Ala Tyr Gly Arg Trp Pro Glu Phe Ile Arg
                100                 105                 110

Asp Asp Glu Ala Asn Pro Val Asp Gln Pro Thr Glu Pro Asp Val Ala
            115                 120                 125

Thr Cys Arg Phe Tyr Thr Leu Asp Thr Val Met Trp Gly Lys Glu Ser
    130                 135                 140

Lys Gly Trp Trp Trp Lys Leu Pro Asp Ala Leu Arg Asp Met Gly Leu
145                 150                 155                 160

Phe Gly Gln Asn Met Tyr Tyr His Tyr Leu Gly Arg Ser Gly Tyr Thr
                165                 170                 175

Val His Val Gln Cys Asn Ala Ser Lys Phe His Gln Gly Ala Leu Gly
                180                 185                 190

Val Phe Ala Ile Pro Glu Tyr Cys Leu Ala Gly Asp Ser Asp Lys Gln
            195                 200                 205

Arg Tyr Thr Ser Tyr Ala Asn Ala Asn Pro Gly Glu Arg Gly Gly Lys
    210                 215                 220

Phe Tyr Ser Gln Phe Asn Lys Asp Asn Ala Val Thr Ser Pro Lys Arg
225                 230                 235                 240

Glu Phe Cys Pro Val Asp Tyr Leu Leu Gly Cys Gly Val Leu Leu Gly
                245                 250                 255

Asn Ala Phe Val Tyr Pro His Gln Ile Ile Asn Leu Arg Thr Asn Asn
                260                 265                 270

Ser Ala Thr Ile Val Leu Pro Tyr Val Asn Ala Leu Ala Ile Asp Ser
            275                 280                 285

Met Val Lys His Asn Asn Trp Gly Ile Ala Ile Leu Pro Leu Ser Pro
    290                 295                 300

Leu Asp Phe Ala Gln Asp Ser Ser Val Glu Ile Pro Ile Thr Val Thr
305                 310                 315                 320

Ile Ala Pro Met Cys Ser Glu Phe Asn Gly Leu Arg Asn Val Thr Ala
                325                 330                 335

Pro Lys Phe Gln Gly Leu Pro Val Leu Asn Thr Pro Gly Ser Asn Gln
                340                 345                 350
```

```
Tyr  Leu  Thr  Ser  Asp  Asn  His  Gln  Ser  Pro  Cys  Ala  Ile  Pro  Glu  Phe
          355                 360                      365

Asp  Val  Thr  Pro  Pro  Ile  Asp  Ile  Pro  Gly  Glu  Val  Lys  Asn  Met  Met
370                      375                 380

Glu  Leu  Ala  Glu  Ile  Asp  Thr  Met  Ile  Pro  Leu  Asn  Leu  Glu  Ser  Thr
385                      390                 395                           400

Lys  Arg  Asn  Thr  Met  Asp  Met  Tyr  Arg  Val  Thr  Leu  Ser  Asp  Ser  Ala
               405                      410                      415

Asp  Leu  Ser  Gln  Pro  Ile  Leu  Cys  Leu  Ser  Leu  Ser  Pro  Ala  Phe  Asp
               420                 425                      430

Pro  Arg  Leu  Ser  His  Thr  Met  Leu  Gly  Glu  Val  Leu  Asn  Tyr  Tyr  Thr
               435                 440                      445

His  Trp  Ala  Gly  Ser  Leu  Lys  Phe  Thr  Phe  Leu  Phe  Cys  Gly  Ser  Met
     450                      455                      460

Met  Ala  Thr  Gly  Lys  Ile  Leu  Val  Ala  Tyr  Ala  Pro  Pro  Gly  Ala  Gln
465                      470                 475                           480

Pro  Pro  Thr  Ser  Arg  Lys  Glu  Ala  Met  Leu  Gly  Thr  His  Val  Ile  Trp
               485                 490                      495

Asp  Leu  Gly  Leu  Gln  Ser  Ser  Cys  Thr  Met  Val  Val  Pro  Trp  Ile  Ser
               500                 505                      510

Asn  Val  Thr  Tyr  Arg  Gln  Thr  Thr  Gln  Asp  Ser  Phe  Thr  Glu  Gly  Gly
               515                 520                      525

Tyr  Ile  Ser  Met  Phe  Tyr  Gln  Thr  Arg  Ile  Val  Val  Pro  Leu  Ser  Thr
     530                      535                      540

Pro  Lys  Ser  Met  Ser  Met  Leu  Gly  Phe  Val  Ser  Ala  Cys  Asn  Asp  Phe
545                      550                 555                           560

Ser  Val  Arg  Leu  Leu  Arg  Asp  Thr  Thr  His  Ile  Ser  Gln  Ser  Ala  Leu
               565                 570                      575

Pro  Gln  Gly  Ile  Glu  Asp  Leu  Thr  Ser  Glu  Val  Ala  Gln  Gly  Ala  Leu
               580                 585                      590

Thr  Leu  Ser  Leu  Pro  Lys  Gln  Gln  Asp  Ser  Leu  Pro  Asp  Thr  Lys  Ala
               595                 600                      605

Ser  Gly  Pro  Ala  His  Ser  Lys  Glu  Val  Pro  Ala  Leu  Thr  Ala  Val  Glu
     610                      615                      620

Thr  Gly  Ala  Thr  Asn  Pro  Leu  Ala  Pro  Ser  Asp  Thr  Val  Gln  Thr  Arg
625                      630                 635                           640

His  Val  Val  Gln  Arg  Arg  Ser  Arg  Ser  Glu  Ser  Thr  Ile  Glu  Ser  Phe
               645                 650                      655

Phe  Ala  Arg  Gly  Ala  Cys  Val  Ala  Ile  Ile  Glu  Val  Asp  Asn  Glu  Gln
               660                 665                      670

Pro  Thr  Thr  Arg  Ala  Gln  Lys  Leu  Phe  Ala  Met  Trp  Arg  Ile  Thr  Tyr
               675                 680                      685

Lys  Asp  Thr  Val  Gln  Leu  Arg  Arg  Lys  Leu  Glu  Phe  Phe  Thr  Tyr  Ser
     690                      695                      700

Arg  Phe  Asp  Met  Glu  Phe  Thr  Phe  Val  Val  Thr  Ala  Asn  Phe  Thr  Asn
705                      710                 715                           720

Ala  Asn  Asn  Gly  His  Ala  Leu  Asn  Gln  Val  Tyr  Gln  Ile  Met  Tyr  Ile
                    725                 730                      735

Pro  Pro  Gly  Ala  Pro  Thr  Pro  Lys  Ser  Trp  Asp  Asp  Tyr  Thr  Trp  Gln
               740                 745                      750

Thr  Ser  Ser  Asn  Pro  Ser  Ile  Phe  Tyr  Thr  Tyr  Gly  Ala  Ala  Pro  Ala
               755                 760                      765

Arg  Ile  Ser  Val  Pro  Tyr  Val  Gly  Leu  Ala  Asn  Ala  Tyr  Ser  His  Phe
     770                      775                      780
```

| | | | | | | | | | | | | | |
|---|---|---|---|---|---|---|---|---|---|---|---|---|---|
| Tyr | Asp | Gly | Phe | Ala | Lys | Val | Pro | Leu | Lys | Thr | Asp | Ala | Asn | Asp | Gln |
| 785 | | | | 790 | | | | 795 | | | | 800 |
| Ile | Gly | Asp | Ser | Leu | Tyr | Ser | Ala | Met | Thr | Val | Asp | Asp | Phe | Gly | Val |
| | | | 805 | | | | 810 | | | | 815 |
| Leu | Ala | Val | Arg | Val | Val | Asn | Asp | His | Asn | Pro | Thr | Lys | Val | Thr | Ser |
| | | | 820 | | | | 825 | | | | 830 |
| Lys | Val | Arg | Ile | Tyr | Met | Lys | Pro | Lys | His | Val | Arg | Val | Trp | Cys | Pro |
| | | 835 | | | | 840 | | | | 845 |
| Arg | Pro | Pro | Arg | Ala | Val | Pro | Tyr | Tyr | Gly | Pro | Gly | Val | Asp | Tyr | Arg |
| 850 | | | | 855 | | | | 860 |
| Asn | Asn | Leu | Asp | Pro | Leu | Ser | Glu | Lys | Gly | Leu | Thr | Thr | Tyr | Gly | Phe |
| 865 | | | | 870 | | | | 875 | | | | 880 |
| Gly | His | Gln | Asn | Lys | Ala | Val | Tyr | Thr | Ala | Gly | Tyr | Lys | Ile | Cys | Asn |
| | | | 885 | | | | 890 | | | | 895 |
| Tyr | His | Leu | Ala | Thr | Lys | Glu | Asp | Leu | Gln | Asn | Ala | Val | Ser | Ile | Met |
| | | | 900 | | | | 905 | | | | 910 |
| Trp | Asn | Arg | Asp | Leu | Leu | Val | Val | Glu | Ser | Lys | Ala | Gln | Gly | Thr | Asp |
| | | 915 | | | | 920 | | | | 925 |
| Ser | Ile | Ala | Arg | Cys | Asn | Cys | Asn | Ala | Gly | Val | Tyr | Tyr | Cys | Glu | Ser |
| 930 | | | | 935 | | | | 940 |
| Arg | Arg | Lys | Tyr | Tyr | Pro | Val | Ser | Phe | Val | Gly | Pro | Thr | Phe | Gln | Tyr |
| 945 | | | | 950 | | | | 955 | | | | 960 |
| Met | Glu | Ala | Asn | Asp | Tyr | Tyr | Pro | Ala | Arg | Tyr | Gln | Ser | His | Met | Leu |
| | | | 965 | | | | 970 | | | | 975 |
| Ile | Gly | His | Gly | Phe | Ala | Ser | Pro | Gly | Asp | Cys | Gly | Gly | Ile | Leu | Arg |
| | | | 980 | | | | 985 | | | | 990 |
| Cys | Gln | His | Gly | Val | Ile | Gly | Ile | Val | Thr | Ala | Gly | Gly | Glu | Gly | Leu |
| | | 995 | | | | 1000 | | | | 1005 |
| Val | Ala | Phe | Ser | Asp | Ile | Arg | Asp | Leu | Tyr | Ala | Tyr | Glu | Glu | Ala |
| | | 1010 | | | | 1015 | | | | 1020 |
| Met | Glu | Gln | Gly | Ile | Ser | Asn | Tyr | Ile | Glu | Ser | Leu | Gly | Ala | Ala | Phe |
| 1025 | | | | 1030 | | | | 1035 | | | | 1040 |
| Gly | Ser | Gly | Phe | Thr | Gln | Gln | Ile | Gly | Asp | Lys | Ile | Ser | Glu | Leu | Thr |
| | | | 1045 | | | | 1050 | | | | 1055 |
| Ser | Met | Val | Thr | Ser | Thr | Ile | Thr | Glu | Lys | Leu | Leu | Lys | Asn | Leu | Ile |
| | | | 1060 | | | | 1065 | | | | 1070 |
| Lys | Ile | Ile | Ser | Ser | Leu | Val | Ile | Ile | Thr | Arg | Asn | Tyr | Glu | Asp | Thr |
| | | | 1075 | | | | 1080 | | | | 1085 |
| Thr | Thr | Val | Leu | Ala | Thr | Leu | Ala | Leu | Leu | Gly | Cys | Asp | Val | Ser | Pro |
| | | | 1090 | | | | 1095 | | | | 1100 |
| Trp | Gln | Trp | Leu | Lys | Lys | Lys | Ala | Cys | Asp | Thr | Leu | Glu | Ile | Pro | Tyr |
| 1105 | | | | 1110 | | | | 1115 | | | | 1120 |
| Val | Ile | Arg | Gln | Gly | Asp | Ser | Trp | Leu | Lys | Lys | Phe | Thr | Glu | Ala | Cys |
| | | | 1125 | | | | 1130 | | | | 1135 |
| Asn | Ala | Ala | Lys | Gly | Leu | Glu | Trp | Val | Ser | Asn | Lys | Ile | Ser | Lys | Phe |
| | | | 1140 | | | | 1145 | | | | 1150 |
| Ile | Asp | Trp | Leu | Arg | Glu | Arg | Ile | Ile | Pro | Gln | Ala | Arg | Asp | Lys | Leu |
| | | | 1155 | | | | 1160 | | | | 1165 |
| Glu | Phe | Val | Thr | Lys | Leu | Lys | Gln | Leu | Glu | Met | Leu | Glu | Asn | Gln | Ile |
| | | | 1170 | | | | 1175 | | | | 1180 |
| Ser | Thr | Ile | His | Gln | Ser | Cys | Pro | Ser | Gln | Glu | His | Gln | Glu | Ile | Leu |
| 1185 | | | | 1190 | | | | 1195 | | | | 1200 |
| Phe | Asn | Asn | Val | Arg | Trp | Leu | Ser | Ile | Gln | Ser | Lys | Arg | Phe | Ala | Pro |

```
                         1205                    1210                    1215
Leu  Tyr  Ala  Leu  Glu  Ala  Lys  Arg  Ile  Gln  Lys  Leu  Glu  His  Thr  Ile
                    1220                    1225                    1230
Asn  Asn  Tyr  Ile  Gln  Phe  Lys  Ser  Lys  His  Arg  Ile  Glu  Pro  Val  Cys
                    1235                    1240                    1245
Leu  Leu  Val  His  Gly  Ser  Pro  Gly  Thr  Gly  Lys  Ser  Val  Ala  Thr  Asn
                    1250                    1255                    1260
Leu  Ile  Ala  Arg  Ala  Ile  Ala  Glu  Lys  Glu  Asn  Thr  Ser  Thr  Tyr  Ser
1265                     1270                    1275                    1280
Leu  Pro  Pro  Asp  Pro  Ser  His  Phe  Asp  Gly  Tyr  Lys  Gln  Gln  Gly  Val
                    1285                    1290                    1295
Val  Ile  Met  Asp  Asp  Leu  Asn  Gln  Asn  Pro  Asp  Gly  Ala  Asp  Met  Lys
                    1300                    1305                    1310
Leu  Phe  Cys  Gln  Met  Val  Ser  Thr  Val  Glu  Phe  Ile  Pro  Pro  Met  Ala
                    1315                    1320                    1325
Ser  Leu  Glu  Glu  Lys  Gly  Ile  Leu  Phe  Thr  Ser  Asn  Tyr  Val  Leu  Ala
                    1330                    1335                    1340
Ser  Thr  Asn  Ser  Ser  Arg  Ile  Thr  Pro  Pro  Thr  Val  Ala  His  Ser  Asp
1345                     1350                    1355                    1360
Ala  Leu  Ala  Arg  Arg  Phe  Ala  Phe  Asp  Met  Asp  Ile  Gln  Val  Met  Gly
                    1365                    1370                    1375
Glu  Tyr  Ser  Arg  Asp  Gly  Lys  Leu  Asn  Met  Ala  Met  Ala  Thr  Glu  Thr
                    1380                    1385                    1390
Cys  Lys  Asp  Cys  His  Gln  Pro  Ala  Asn  Phe  Lys  Arg  Cys  Cys  Pro  Leu
                    1395                    1400                    1405
Val  Cys  Gly  Lys  Ala  Ile  Gln  Leu  Met  Asp  Lys  Ser  Ser  Arg  Val  Arg
                    1410                    1415                    1420
Tyr  Ser  Val  Asp  Gln  Ile  Thr  Thr  Met  Ile  Ile  Asn  Glu  Arg  Asn  Arg
1425                     1430                    1435                    1440
Arg  Ser  Asn  Ile  Gly  Asn  Cys  Met  Glu  Ala  Leu  Phe  Gln  Gly  Pro  Leu
                    1445                    1450                    1455
Gln  Tyr  Lys  Asp  Leu  Lys  Ile  Asp  Ile  Lys  Thr  Arg  Pro  Pro  Pro  Glu
                    1460                    1465                    1470
Cys  Ile  Asn  Asp  Leu  Leu  Gln  Ala  Val  Asp  Ser  Gln  Glu  Val  Arg  Asp
                    1475                    1480                    1485
Tyr  Cys  Glu  Lys  Lys  Gly  Trp  Ile  Val  Asn  Ile  Thr  Ser  Gln  Val  Gln
                    1490                    1495                    1500
Thr  Glu  Arg  Asn  Ile  Asn  Arg  Ala  Met  Thr  Ile  Leu  Gln  Ala  Val  Thr
1505                     1510                    1515                    1520
Thr  Phe  Ala  Ala  Val  Ala  Gly  Val  Val  Tyr  Val  Met  Tyr  Lys  Leu  Phe
                    1525                    1530                    1535
Ala  Gly  His  Gln  Gly  Ala  Tyr  Thr  Gly  Leu  Pro  Asn  Lys  Arg  Pro  Asn
                    1540                    1545                    1550
Val  Pro  Thr  Ile  Arg  Ala  Ala  Lys  Val  Gln  Gly  Pro  Gly  Phe  Asp  Tyr
                    1555                    1560                    1565
Ala  Val  Ala  Met  Ala  Lys  Arg  Asn  Ile  Val  Thr  Ala  Thr  Thr  Ser  Lys
                    1570                    1575                    1580
Gly  Glu  Phe  Thr  Met  Leu  Gly  Val  His  Asp  Asn  Val  Ala  Ile  Leu  Pro
1585                     1590                    1595                    1600
Thr  His  Ala  Ser  Pro  Gly  Glu  Ser  Ile  Val  Ile  Asp  Gly  Lys  Glu  Val
                    1605                    1610                    1615
Glu  Ile  Leu  Asp  Ala  Lys  Ala  Leu  Glu  Asp  Gln  Ala  Gly  Thr  Asn  Leu
                    1620                    1625                    1630
```

-continued

```
Glu  Ile  Thr  Ile  Ile  Thr  Leu  Lys  Arg  Asn  Glu  Lys  Phe  Arg  Asp  Ile
             1635                     1640                     1645

Arg  Gln  His  Ile  Pro  Thr  Gln  Ile  Thr  Glu  Thr  Asn  Asp  Gly  Val  Leu
1650                     1655                     1660

Ile  Val  Asn  Thr  Ser  Lys  Tyr  Pro  Asn  Met  Tyr  Val  Pro  Val  Gly  Ala
1665                     1670                     1675                     1680

Val  Thr  Glu  Gln  Gly  Tyr  Leu  Asn  Leu  Gly  Gly  Arg  Gln  Thr  Ala  Arg
             1685                     1690                     1695

Ile  Leu  Met  Tyr  Asn  Phe  Pro  Thr  Arg  Ala  Gly  Gln  Cys  Gly  Gly  Val
             1700                     1705                     1710

Ile  Thr  Cys  Thr  Gly  Lys  Val  Ile  Gly  Met  His  Val  Gly  Gly  Asn  Gly
             1715                     1720                     1725

Ser  His  Gly  Phe  Ala  Ala  Ala  Leu  Lys  Arg  Ser  Tyr  Phe  Thr  Gln  Ser
             1730                     1735                     1740

Gln  Gly  Glu  Ile  Gln  Trp  Met  Arg  Pro  Ser  Lys  Glu  Ala  Gly  Tyr  Pro
1745                     1750                     1755                     1760

Ile  Ile  Asn  Ala  Pro  Thr  Lys  Thr  Lys  Leu  Glu  Pro  Ser  Ala  Phe  His
             1765                     1770                     1775

Tyr  Val  Phe  Glu  Gly  Val  Lys  Glu  Pro  Ala  Val  Leu  Thr  Lys  Asn  Asp
                  1780                     1785                     1790

Pro  Arg  Leu  Lys  Thr  Asp  Phe  Glu  Glu  Ala  Ile  Phe  Ser  Lys  Tyr  Val
             1795                     1800                     1805

Gly  Asn  Lys  Ile  Thr  Glu  Val  Asp  Glu  Tyr  Met  Lys  Glu  Ala  Val  Asp
1810                     1815                     1820

His  Tyr  Ala  Gly  Gln  Leu  Met  Ser  Leu  Asp  Ile  Ser  Thr  Glu  Gln  Met
1825                     1830                     1835                     1840

Cys  Leu  Glu  Asp  Ala  Met  Tyr  Gly  Thr  Asp  Gly  Leu  Glu  Ala  Leu  Asp
                  1845                     1850                     1855

Leu  Ser  Thr  Ser  Ala  Gly  Tyr  Pro  Tyr  Val  Ala  Met  Gly  Lys  Lys  Lys
                  1860                     1865                     1870

Arg  Asp  Ile  Leu  Asn  Lys  Gln  Thr  Arg  Asp  Thr  Lys  Glu  Met  Gln  Arg
             1875                     1880                     1885

Leu  Leu  Asp  Ala  Tyr  Gly  Ile  Asn  Leu  Pro  Leu  Val  Thr  Tyr  Val  Lys
             1890                     1895                     1900

Asp  Glu  Leu  Arg  Ser  Lys  Thr  Lys  Val  Glu  Gln  Gly  Lys  Ser  Arg  Leu
1905                     1910                     1915                     1920

Ile  Glu  Ala  Ser  Ser  Leu  Asn  Asp  Ser  Val  Ala  Met  Arg  Met  Ala  Phe
                  1925                     1930                     1935

Gly  Asn  Leu  Tyr  Ala  Ala  Phe  His  Arg  Asn  Pro  Gly  Val  Val  Thr  Gly
                  1940                     1945                     1950

Ser  Ala  Val  Gly  Cys  Asp  Pro  Asp  Leu  Phe  Trp  Ser  Lys  Ile  Pro  Val
                  1955                     1960                     1965

Leu  Met  Glu  Glu  Lys  Leu  Phe  Ala  Phe  Asp  Tyr  Thr  Gly  Tyr  Asp  Ala
             1970                     1975                     1980

Ser  Leu  Ser  Pro  Ala  Trp  Phe  Glu  Ala  Leu  Lys  Met  Val  Leu  Glu  Lys
             1985                     1990                     1995                     2000

Ile  Gly  Phe  Gly  Asp  Arg  Val  Asp  Tyr  Ile  Asp  Tyr  Leu  Asn  His  Ser
                  2005                     2010                     2015

His  His  Leu  Tyr  Lys  Asn  Lys  Ile  Tyr  Cys  Val  Lys  Gly  Gly  Met  Pro
             2020                     2025                     2030

Ser  Gly  Cys  Ser  Gly  Thr  Ser  Ile  Phe  Asn  Ser  Met  Ile  Asn  Asn  Leu
             2035                     2040                     2045

Ile  Ile  Arg  Thr  Leu  Leu  Leu  Lys  Thr  Tyr  Lys  Gly  Ile  Asp  Leu  Asp
             2050                     2055                     2060
```

| | | | | | | | | | | | | | | |
|---|---|---|---|---|---|---|---|---|---|---|---|---|---|---|
| His | Leu | Lys | Met | Ile | Ala | Tyr | Gly | Asp | Asp | Val | Ile | Ala | Ser | Tyr | Pro |
| 2065 | | | | | 2070 | | | | 2075 | | | | | | 2080 |
| His | Glu | Val | Asp | Ala | Ser | Leu | Leu | Ala | Gln | Ser | Gly | Lys | Asp | Tyr | Gly |
| | | | | 2085 | | | | | 2090 | | | | | 2095 | |
| Leu | Thr | Met | Thr | Pro | Ala | Asp | Lys | Ser | Ala | Thr | Phe | Glu | Thr | Val | Thr |
| | | | 2100 | | | | | 2105 | | | | | 2110 | | |
| Trp | Glu | Asn | Val | Thr | Phe | Leu | Lys | Arg | Phe | Phe | Arg | Ala | Asp | Glu | Lys |
| | | 2115 | | | | | 2120 | | | | | 2125 | | | |
| Tyr | Pro | Phe | Leu | Ile | His | Pro | Val | Met | Pro | Met | Lys | Glu | Ile | His | Glu |
| | | 2130 | | | | 2135 | | | | | 2140 | | | | |
| Ser | Ile | Arg | Trp | Thr | Lys | Asp | Pro | Arg | Asn | Thr | Gln | Asp | His | Val | Arg |
| 2145 | | | | | 2150 | | | | | 2155 | | | | | 2160 |
| Ser | Leu | Cys | Leu | Leu | Ala | Trp | His | Asn | Gly | Glu | Glu | Glu | Tyr | Asn | Lys |
| | | | | 2165 | | | | | 2170 | | | | | 2175 | |
| Phe | Leu | Ala | Lys | Ile | Arg | Ser | Val | Pro | Ile | Gly | Arg | Ala | Leu | Leu | Leu |
| | | | 2180 | | | | | 2185 | | | | | 2190 | | |
| Pro | Glu | Tyr | Ser | Thr | Leu | Tyr | Arg | Arg | Trp | Leu | Asp | Ser | Phe | | |
| | | | 2195 | | | | 2200 | | | | | 2205 | | | |

( 2 ) INFORMATION FOR SEQ ID NO:3:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:3:

CGCCTCAGTA AATTTTTTCA ACCAACTATC                30

( 2 ) INFORMATION FOR SEQ ID NO:4:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:4:

GGCGTATCTG ACAAGGG                17

( 2 ) INFORMATION FOR SEQ ID NO:5:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:5:

CTGCAGTAAT ACGACTCACT ATAGGTTAAA ACAGCTCTGG GGTTG                              45

( 2 ) INFORMATION FOR SEQ ID NO:6:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:6:

GAATCATGGT GTCTATCTC                                                           19

( 2 ) INFORMATION FOR SEQ ID NO:7:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:7:

CTCGTTTGTG GCATAAC                                                             17

( 2 ) INFORMATION FOR SEQ ID NO:8:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:8:

CCCATGGGGA TGCACCG                                                             17

( 2 ) INFORMATION FOR SEQ ID NO:9:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( i i ) MOLECULE TYPE: DNA (genomic)

-continued (iii) HYPOTHETICAL: NO (iv) ANTI-SENSE: NO (xi) SEQUENCE DESCRIPTION: SEQ ID NO:9:

CTGCAGTAAT ACGACTCACT ATAGGTTAAA ACAGCTCTGG GGTTTG    46